US008524651B2

(12) United States Patent
Ashdown

(10) Patent No.: US 8,524,651 B2
(45) Date of Patent: Sep. 3, 2013

(54) METHOD OF THERAPY

(75) Inventor: Martin Leonard Ashdown, Victoria (AU)

(73) Assignee: ImmunAid Pty Ltd. (AU)

( * ) Notice: Subject to any disclaimer, the term of this patent is extended or adjusted under 35 U.S.C. 154(b) by 0 days.

(21) Appl. No.: 13/396,254

(22) Filed: Feb. 14, 2012

(65) Prior Publication Data

US 2012/0156225 A1 Jun. 21, 2012

Related U.S. Application Data

(63) Continuation of application No. 10/576,981, filed as application No. PCT/AU2004/001456 on Oct. 22, 2004.

(30) Foreign Application Priority Data

Oct. 24, 2003 (AU) ................................ 2003905858

(51) Int. Cl.
*A01N 61/00* (2006.01)
(52) U.S. Cl.
USPC ............................................... 514/1; 435/7.1
(58) Field of Classification Search
None
See application file for complete search history.

(56) References Cited

U.S. PATENT DOCUMENTS

| | | | |
|---|---|---|---|
| 5,057,423 A | 10/1991 | Hiserodt et al. | |
| 5,141,867 A | 8/1992 | Ivanoff et al. | |
| 5,308,626 A | 5/1994 | Landucci et al. | |
| 5,814,639 A | 9/1998 | Liotta et al. | |
| 5,939,400 A | 8/1999 | Steinmann et al. | |
| 6,090,392 A | 7/2000 | Berman | |
| 6,107,020 A | 8/2000 | Skowron | |
| 6,110,898 A | 8/2000 | Malone et al. | |
| 2002/0094542 A1 | 7/2002 | Leskovar | |
| 2003/0228320 A1 | 12/2003 | Ashdown | |
| 2004/0180357 A1 | 9/2004 | Reich et al. | |
| 2004/0192629 A1 | 9/2004 | Xu et al. | |
| 2004/0203024 A1 | 10/2004 | Baker et al. | |
| 2005/0002929 A1 | 1/2005 | Sanchez-Madrid et al. | |
| 2005/0180971 A1 | 8/2005 | Ashdown | |
| 2006/0134713 A1 | 6/2006 | Rylat et al. | |
| 2007/0202119 A1 | 8/2007 | Ashdown | |
| 2008/0248022 A1 | 10/2008 | Ashdown | |
| 2009/0041760 A1 | 2/2009 | Ashdown | |
| 2012/0220640 A1 | 8/2012 | Ashdown et al. | |

FOREIGN PATENT DOCUMENTS

| | | |
|---|---|---|
| DE | 4120296 | 3/1992 |
| EP | 0239400 | 9/1987 |
| EP | 0358154 | 3/1990 |
| EP | 0374207 | 6/1990 |
| EP | 0656778 | 6/1995 |
| EP | 0736533 | 10/1996 |
| EP | 0945727 | 9/1999 |
| WO | WO 89/09620 | 10/1989 |
| WO | WO 90/07119 | 6/1990 |
| WO | WO 91/09872 | 7/1991 |
| WO | WO 92/22654 | 12/1992 |
| WO | WO 93/19183 | 9/1993 |
| WO | WO 94/07921 | 4/1994 |
| WO | WO 95/20660 | 8/1995 |
| WO | WO 96/30025 | 10/1996 |
| WO | WO 98/44001 | 10/1998 |
| WO | WO 01/08702 | 2/2001 |
| WO | WO 02/13828 | 2/2002 |
| WO | WO 02/45735 | 6/2002 |
| WO | WO 03/068257 | 8/2003 |
| WO | WO 03/070270 | 8/2003 |
| WO | WO 2005/034995 | 4/2005 |
| WO | WO 2005/040816 | 5/2005 |
| WO | WO 2005/070090 | 8/2005 |
| WO | WO 2005/072777 | 8/2005 |
| WO | WO 2006/026821 | 3/2006 |

OTHER PUBLICATIONS

Bach, Nature Rev, Immunol, 2003, 3:189-198.*
Osterlund et al., Br J Cancer, 2002, 87:591-599.*
Ataxia telangiectasia, Wikipedia, found at http://en.wikipedia.org/wiki/Ataxia_telangiectasia, last modified Jun. 11, 2011, 8 pages.
Cockayne syndrome, Wikipedia, found at http://en.wikipedia.org/wiki/Cockayne_syndrome, last updated Jun. 11, 2011, 3 pages.
ABC Online, "AM—Cells Switched off for tumour treatment", Mar. 12, 2009, http://www.abc.net.au/am/content/2008/s2513799.htm, accessed Apr. 5, 2009.
Adachi, Susumu, et al., "A Pilot Study of Paclitaxel and Carboplatin for Recurrent Ovarian Cancer" Oncology Reports 8: 285-288, 2001.
Agelaki, S., et al., "Second-line treatment with vinorelbine and carboplatin in patients with advanced non-small cell lung cancer. A multicenter phase 11study." Lung Cancer. Dec. 2001; 34 Suppl 4:S77-80.
Ahlers, J. et al., "A Push-pull Approach to Maximize Vaccine Efficacy: Abrogating Suppression with an IL-13 Inhibitor While Augmenting Help with Granulocyte/Macrophage Colony-Stimulating Factor and CD40L", Proceedings of the National Academy of Sciences of the United States of America. Oct. 2002. vol. 99, No. 20.
Ahmad, s. A., et al., "Extraosseous osteosarcoma: response to treatment and long-term outcome" J Clin Oncol. Jan. 15, 2002;20(2):521-7.
Aitini, E., et al., Epirubiciin, cicplatin and continuous infusion 5-ftuorouracil (ECF) in locally advanced or metastatic gastric cancer: a single institution experience Tumori. Jan.-Feb. 2001; 87(1):20-4.
Amadori, D., et al., Ovarian cancer: natural history and metastatic pattern. Front Biosci. Jan. 1, 1997;2:g8-10.
Anderson, et al., "The Effects of Cyclophosphamide and Irradiation Singly and in Combination Upon Sal Growth in A/J Mice," American Journal of Pathology, May 1987, vol. 127, No. 2, pp. 373-379.

(Continued)

*Primary Examiner* — Mark Halvorson
(74) *Attorney, Agent, or Firm* — Sheridan Ross P.C.

(57) ABSTRACT

Numerous diseases have been linked to the production of regulator cells. The present invention relates to the observation that the immune system is cycling in these diseases. Based on these observations, the present invention provides methods for treating diseases such as cancer and a HIV infection. The present invention also relates to methods of determining when a therapy to treat a disease characterized by the production of regulator cells should be administered to a patient.

9 Claims, 13 Drawing Sheets

(56) References Cited

OTHER PUBLICATIONS

Figure 1A:
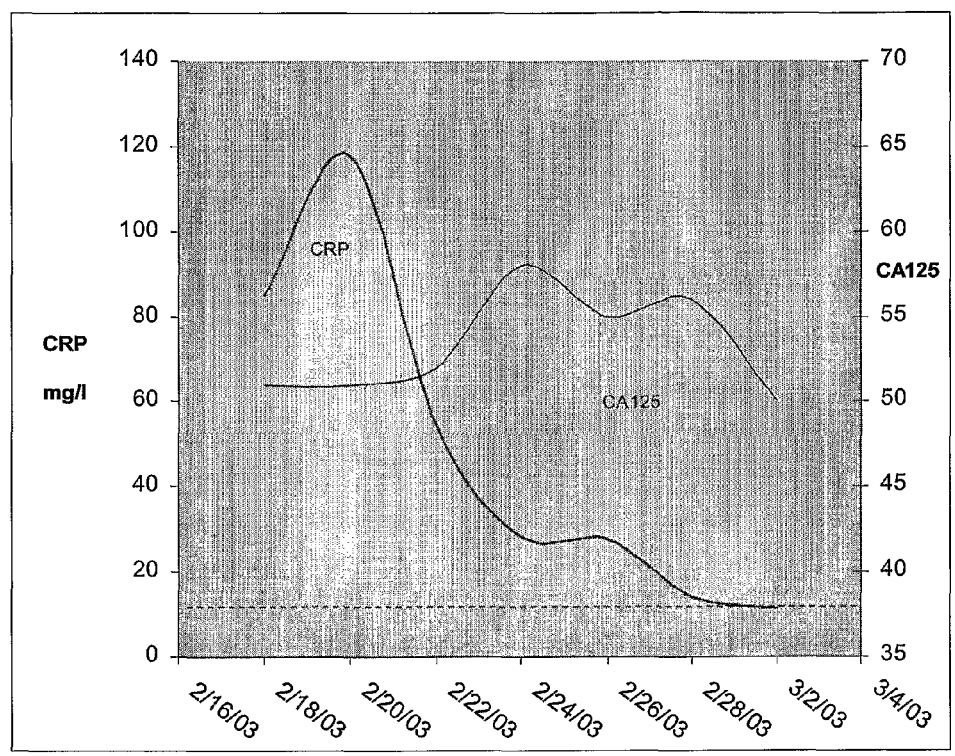

Annunziato, et al., "Phenotype, Localization, and Mechanism of Suppression of CD4+ CD25+ Human Thymocytes," The Journal of Experimental Medicine, vol. 196, No. 3, pp. 379-387, Aug. 5, 2002.
Ashamalla, H.. et al., Hyperfractionated radiotherapy and paclitaxel for locally advanced/unresectable pancreatic cancer. Int J Radiat Oncol Bioi Phys. Mar. 1, 2003; 55(3):679-87.
Atkins MB, et al .. "A phase II pilot trial of concurrent biochemotherapy with cisplatin, vinblastine, temozolomide. interleukin 2, and IFN-alpha 2B in patients with metastatic melanoma." Clin. Cancer Res. Oct. 2002;8(10):3075-81.
Aziz, Mehar, M.D., et al., "Evaluation of Cell-Mediated Immunity and Circulating Immune Complexes as Prognostic Indicators in Cancer Patients" Cancer Detection and Prevention, 22(2):87-99 (1998).
Babbe, et al., "Clonal Expansions of CD8+ T Cells Dominate the T Cell Infiltrate in Active Multiple Sclerosis Lesions as Shown by Micromanipulation and Single Cell Polymerase Chain Reaction," The Journal of Experimental Medicine, vol. 192, No. 3, pp. 393-404, Aug. 7, 2000.
Bafaloukos D., et al., "Docetaxel in combination with dacarbazine in patients with advanced melanoma." Oncology. 2002;63(4):333-7.
Bafaloukos D., et al., "Temozolomide in combination with docetaxel in patients with advanced melanoma: a phase II study of the Hellenic Cooperative Oncology Group." J Clin Oncol. Jan. 15, 2002;20(2):420-5.
Balint, et al., "Immune complexes with antiglobulin activity in sera of Moloney sarcoma-bearing rats," Clin. Exp. Immunol., 1982, vol. 48, pp. 70-78.
Bar Sela, G.. et al. Etoposide. doxorubicin and cisplatin alternating with 5-fluorouracil. doxorubicin and high-dose methotrexate in patients with advanced adenocarcinoma of the stomach or the gastroesophageal junction. J Chemother. Dec. 2002;14(61:623-6).
Barin. F. et al.; Virus Envelope Protein of HTL V-III Represents Major Target Antigen for Antibodies in AIDS 54 Patients; May 31,1985; pp. 1094-1096; V. 228; Science; Gale Group Information Integrity.
Barrett, et al., "Undulations in the Time-Response Curve for Tumor Immunity after Primary Immunization with Washed Erythrocytes," Journal of National Cancer Institute, vol. 18, No. 1, Jan. 1957, pp. 57-63.
Bataille. R.. et at, -Cytokines and lymphoplasmocytic proliferations: essential role or interleukin 6. xp. 002351766. Feb. 1. 1993. La Revue du practicien. vol. 43. No. 3. pp. 275-278.
Beck TM. et al. Treatment of metastatic colorectal carcinoma with 5-FU. mitomycin, vincristine and methotrexate. Cancer Treat Rep. Apr. 1984;68(4):647-50.
Bedikian AY. et al., "Phase II trial of docetaxel in patients with advanced cutaneous malignant melanoma previously untreated with chemotherapy" J Clin Oncol. Dec. 1995;13(12):2865-B.
Beerblock. K. et al., Bimonthly high dose leucovorin and 5-fluorouracil 48-hour continuous infusion in patients with advanced colorectal carcinoma. Groupe d'Etude et de Recherche sur les Cancers de l'Ovaire et Digestifs (GERCODI. Cancer. Mar. 15, 1997; 79(61: 1100-5.) (Abstract only).
Beilharz et al., "Timed ablation of regulatory CD4+ T cells can prevent murine AIDS progression" J Immunol 2004, 172:4917-4925.
Beilharz et al., "Prevention of Murine AIDS by timed immune regulator cell ablation", Journal of Interferon and Cytokine Research, vol. 22, No. suppl. 1, Oct. 2002, pp. S-171.
Belkaid et al., "Natural regulatory T cells in infectious disease" Nature Immunol 2005, 6(4):353-360.
Belli, Filiberto, et al., Vaccination of Metastatic Melanoma Patients with Autologous Tumor-Dejived Heat Shock Protein gp96-Peptide Complexes: Clinical and Immunologic Findings Journal of clinical Oncology, vol. 20, No. 20 (Oct. 15), 2002: pp. 4169-4180.
Berd et al., "Treatment of Metastatic Melanoma with Autologous, Hapten-Modified Melanoma Vaccine: Regression of Pulmonary Metastases", Int. J. Cancer: 94, 531-539 (2001).
Berd. D "Effect of Low Dose Cyclophosphamide on the Immune System of Cancer Patients: Reduction of T•Suppressor Function without Depletion of the C08+ Subset." XP-002351767 Cancer Research. vol. 47. Issue 12, Jun. 15, 1987.
Berd. David. et at, Effect of Low Dose Cyclophosphamide on the Immune System of Cancer Patients: 6 Depletion of CD4+. 2H4+ Suppressor-inducer T.cells XP 000900007 Cancer Research 48. 1671-1675. Mar. 15, 1988.
Beyer et al., "Regulatory T cells in cancer" Blood 2006, 108(3)804-811.
Blanke CD, et al, "Phase II study of trimetrexate, fluorouracil, and leucovorin for advanced colorectal cancer" J Clin Oncol, Mar. 1997; 15(3):915-20 retrieved from the Internet Dec. 19, 2006.
Bon G., et al., "Fluctuations in CA 125 and CA 15-3 Serum Concentrations During Spontaneous Ovulatory Cycles", Human Reoroduction, Feb. 1999, vol. 14, No. 2, pp. 566-570.
Borjabad A, Brooks AI, Volsky DJ. "Gene expression profiles of HIV-1-infected glia and brain: toward better understanding of the role of astrocytes in HIV-1-associated neurocognitive disorders." J Neuroimmune Pharmacol. Mar. 2010;5(1 ):44-62. Epub Aug. 21, 2009. Review.
Brandi et al., "Effect of antiviral treatments on the bone marrow in murine AIDS" Blood Cells, Molecules and Diseases 1995, 21 (12)109-118.
Brennan et al., "Chimeric Plant Virus Particles Administered Nasally or Orally Induce Systemic and Mucosal Immune Responses in mice," Journal of Virology, Feb. 1999, vol. 73, No. 2, pp. 930-938.
Bretz, et al., "Inflammatory Cytokine Regulation of Fas-mediated Apoptosis in Thyroid Follicular Cells," The Journal of Biological Chemistry, vol. 274, No. 36, pp. 25433-25438, Sep. 3, 1999.
Bruzzone, et al., "Temporal Patterns of C-Reactive Proteins and Other Acute Phase Proteins After Kidney Transplantation," Transplantation Proceedings, vol. XIX, No. 5, pp. 3727-3730, Oct. 1987.
Buzaid A.C., et al., "Phase II study of neoadjuvant concurrent biochemotherapy in melanoma patients with local-regional metastases." Melanoma Res. 1998 De;8(6):549-56 abstract only.
Calvo, E., et al., Irinotecan, oxaliplatin, and 5-fluorouracil/leucovorin combination chemotherapy in advanced colorectal carcinoma: a phase II study. Clin Colorectal Cancer. Aug. 2002;2(2):104-10, abstract only.
Carcelain G. et al. "Reconstitution of CD4+ T lymphocytes in HIV-infected individuals following antiretroviral therapy". Curr Opin Immunol. Aug. 2001; 13(4 ):483-8.
Cardoso et al., "Immunization with Plasmid DNA Encoding for the Measles Virus Hemagglutinin and Nucleoprotein Leads to Humoral and Cell-Mediated Immunity," Virology 225, 293-299 (1996), Article No. 0603.
Carini et al. (1994) AIDS Res. Hum. Retroviruses 10:121-130.
Carr, B.I., et al., "Phase II study of Spherex (degradable starch microspheres) injected into the hepatic artery in conjunction with doxorubicin and cisplatin in the treatment of advanced-stage hepatocellular carcinoma: interim analysis." Semin Oncol. Apr. 1997;24(2 Suppl 6):S6-97-S6-99, abstract only.
Cascinu, S., et al. "A phase II study of Tomudex alternated with methotrexate, 5-fluorouracil, leucovorin in first-line chemotherapy of metastatic colorectal cancer." Ann Oncol. 199 August; 10(8):985-7 (abstract only).
Cassinello, J. et al., "Phase 11study of weekly irinotecan (CPT-II) as second-line treatment of patients with advanced colorectal cancer" Med Oncol. 2003; 20(1): 37-43.
Cassinello, J., et al., "Activity and safety of oxaliplatin with weekly 5-fluorouracil bolus and low-dose leucovorin as fist-line treatment for advanced colorectal cancer." Clin Colorectal Cancer. Aug. 2003; 3(2): 108-12 (abstract only).
Chahinian, A. P., et al., "Randomized phase 11trial of cisplatin with mitomycin or doxorubicin for malignant mesothelioma by the Cancer and Leukemia Group B" J Clin Oncol, Aug. 1993; 11(8):1559-65.
Chan EY, et al. "Quantitative analysis of human immunodeficiency virus type 1-infected CD4+ cell proteome: dysregulated cell cycle progression and nuclear transport coincide with robust virus production" J Virol. Jul. 2007;81 (14):7571-83. Epub May 9, 2007.
Chapman. PB, et al., "Clinical results using biochemotherapy as a standard of care in advanced melanoma" Melanoma Res. Aug. 2002; 12(4):381-7.

Chattopadhyay, Sisir K. et al.; Structure of Endogenous Murine Leukemia Virus DNA in Mouse Genomes; Oct. 1980. pp. 5774-5778; V. 77. No. 10; Proc. Natl. Acad. Sci. USA; Biochemistry.

Child et al., "Serum beta 2 microglobulin and C-reactive protein in the monitoring of lymphomas findings in a multicenter study and experience in selected patients," vol. 45 No. 2, pp. 318-326 (Jan. 1980).

Chino "Diagnosis of malignant melanoma in the nasal cavity with touch-fluorescence method and detection of 5-S-cysteinyldopa," Jibi Inkioka Tokeibu Geka, 1994, vol. 66, No. 4, pp. 313-318 (Abstract Only).

Cho EK, et al., "Epirubicin, cisplatin, and protracted venous infusion of 5-fluorouracil for advanced gastric carcinoma" J Korean Med Sci, Jun. 2002; 17(3):348-52.

Cho, et al., "Identification of Serum Amyloid A Protein As a Potentially Useful Biomarker to Monitor Relapse of Nasopharyngeal Cancer by Serum Proteomic Profiling," Clinical Cancer Research, vol. 10, pp. 43-52, Jan. 1, 2004.

Choi TK, et al., "Chemotherapy for advanced hepatocellular carcinoma. Adriamycin versus quadruple chemotherapy" Cancer, Feb. 1, 1984; 53(3): 401-5.

Colic. M. et al., "Thymic Response to Thermal Injury in Mice: I. Alterations of Thymocyte Subsets Studied by Flow Cytometry and Immunohistochemistry", Burns: Journal of the International Society for Burn Iniuries, Jun. 1989. vol. 15, No. 3, pp. 155-161.

Coll, J. et al.; Antibodies to Human Immunodeficiency Virus (HIV-1) in Autoimmune Diseases: Primary Sjogren's Syndrome. Systemic Lupus Erythematosus, Rheumatoid Arthritis and Autoimmune Thyroid Diseases; Dec. 21, 1995; DD. 451-457; V. 14. No. 4; Clinical Rheumatology.

Comella P., et al., Biweekly irinotecan or raltitrexed plus 5S-leucovorin and bolus s-nucrcoract in advanced colorectal carcinoma: a Southern Italy Cooperative Oncology Group phase 11-111 randomized trial, Ann Oncol. Oct. 2000; 11(10):1323-33.

Conry et al., "Immune Response to a Carcinoembryonic Antigen Polynucleotide Vaccine," Cancer Research 54, 1164-1168, Mar. 1, 1994.

Constenia, M., et al., Docetaxel, 5-fluorouracil, and leucovorin as treatment for advanced gastric cancer: results of a phase 11study, Gastric Cancer. 2002; 5(3):142-7.

Coulie et al., "A Monoclonal Cytolytic T-Lymphocyte Response Observed in a Melanoma Patient Vaccinated with Tumor-Specific Antigenic Peptide Encoded by Gene MAGE-3," PNAS, vol. 98, No. 18, 10290-10295, Aug. 28, 2001.

Covens, A., et al., "Phase 11study of mitomycin C and 5 fluorouracil in platinum resistant ovarian cancer" Eur J Gynaecol Oncol., 1992; 13(2):125-30.

Coventry, et al., "CRP identifies homeostatic immune oscillations in cancer patients: a potential treatment targeting tool?" Journal of Translational Medicine, Nov. 30, 2009, 7:102.

Cox et al., "Bovine Herpesvirus 1: Immune Responses in Mice and Cattle Injected with Plasmid DNAn," Journal of Virology, vol. 67, No. 9, Sep. 1993, pp. 5664-5667.

Cunnigham RK et al. "Murine AIDS: a model for the human disease or a distinct entity?" Immunol Res. vol. 13(1994), pp. 21-28.

Daar E., et al., "Acute HIV Syndrome After Discontinuation of Antiretroviral Therapy in a Patient Treated Before Seroconversion", Annals of Internal Medicine, May 15. 1998, vol. 128. No. 10.

Database Biosis [online], Biosciences Information Service, Philadelphia, PA. 1994, Chino Kazuo, "Diagnosis of Malignant Melanoma in the Nasal Cavity with Touch Fluorescence Method and Detection of 5-S-Cysteinyldopa", database accession No. PREV1999497330363, abstract.

Database Medline [online], US National Library of Medicine, Bethesda, MD, Oct. 1985, Jibiki et al., "Tumor Markers in Testicular Tumors", database accession No. NLM3841165, abstract.

Davis et al., "DNA-Based Immunization Induces Continuous Secretion of Hepatitis B Surface Antigen and High Levels of Circulating Antibody," Human Molecular Genetics, 1993, vol. 2, No. 11, 1847-1851.

Davis et al., "Establishment of a Murine Model of Malignant Mesothelioman," Int. J. Cancer: 52,881-886 (1992).

Denham, et al., "The Occurrence of Two Types of Cytotoxic Lymphoid Cells in Mice Immunised with Allogeneic Tumour Cells," Transplantation, 1970, vol. 9, No. 4, pp. 366-382.

Dennehy. Penelope H; Active Immunization in the United States: Developments over the Past Decade. Clinical Microbiology Reviews; Oct. 2001; pp. 872-908; V. 14. No. 4; American Society for Microbiology.

Dias et al., "Animal models used for the evaluation of antiretroviral therapies" in Current HIV Research 2006, 4(4):431-446, Abstract only. On the world wide web at http://www.bentham.org/chivr/contabs/chiv4-4.htm.

Dieras V., et al., Multicentre phase llstudy of oxaliplatin as a single-agent in cisplatin/carboplatin +/- taxane-pretreated ovarian cancer patients. Ann Oncol. Feb. 2002; 13(2):258-66.

DiPaola, R.S., et al., Gemcitabine combined with sequential paclitaxel and carboplatin in patients with urothelial cancers and other advanced malignancies. Med Sci Monit. Feb. 2003; 9(2):PI5-11.

Dittmer et al., "Functional impairment of CD8+ T cells by regulatory T cells during persistent retroviral infection" Immunity 2004, 20:293-303.

Eda et al., "Development of a New Microparticle-Enhanced Turbidimetric Assay for C-Reactive Protein With Superior Features in Analytical Sensitivity and Dynamic Rangen," Journal of Clinical Laboratory IAnalysis, 12:137-144 (1998).

Einzig, A. I., "A phase II study of taxol in patients with malignant melanoma" Invest New Drugs. Feb. 1991;9(1 )59-64.

Einzig, A. I., "Review of phase" trials of Taxol (paclitaxel) in patients with advanced ovarian cancer. Ann Oncol. 1994;5 Suppl 6:S29-32.

Einzig, AI., et al., "Phase II trial of docetaxel (Taxotere) in patients with metastatic melanoma previously untreated with cytotoxic chemotherapy" Med oncol. Jun. 1996;13(2): 111-7.

Eisenbraun et al., "Examination of Parameters Affecting the Elicitation of Humoral Immune Responses by Particle Bombardment-Mediated Genetic Immunlzation," DNA and Cell Biology, vol. 12, No. 9, 1993, pp. 791-797.

Elliott, et al., "Suppression of Fever and the Acute-Phase Response in a Patient with Juvenile Chronic Arthritis Treated with Monoclonal Antibody to Tumour Necrosis Factor-x (cA2)," British Journal of Rheumatology, vol. 36, No. 5, pp. 0 589-593, 1997.

Errante D. et al. "Hodgkin's disease in 35 patients with HIV infection: an experience with epirubicin, bleomycin, vinblastine and prednisone chemotherapy in combination with antiretroviral therapy and primary use of G-CSF". Ann Oncol. Feb. 1999; 10(2): 189-95.

Estes et al., "Simian Immunodeficiency Virus-Induced Lymphatic Tissue Fibrosis is Mediated by Transforming Growth Factor B1-Positive Regulatory T-Cells and Begins in Early Infection," Journal of Infectious Diseases, 2007:195, (Feb. 15) pp. 551-561.

Faivre, S., "Phase I-II and pharmacokinetic study of gemcitabine combined with oxaliplatin in patients with advanced non-small-cell lung cancer and ovarian carcinoma" Ann On col. Sep. 2002;13(9):1479-89.

Falcone, A., et al., "5-flluorouracil administered as a 48-hour chronomodulated infusion in combination with leucovorin and cisplatin: a rendomized phase II study in metastatic colorectal cancer." Oncology. 2001 ;61 (1):28-35.

Fisson, et al., "Continuous Activation of Autoreactive CD4+ CD25+ Regulatory T Cells in the Steady State," The Journal of Experimental Medicine, vol. 198, No. 5, pp. 737-746, Sep. 1, 2003.

Forastiere, A.A., et al., "Cisplatin, vinblastine, and mitoguazone chemotherapy for epidermoid and adenocarcinoma of the esophagus." J. Clin Oncol. Aug. 1987;5(8): 1143-9.

Fountzilas, G., et al. "Radiation and concomitant weekly administration of paclitaxel in patients with glioblastoma multiforme. A phase II Study." J. Neurooncol. 1999;45(2):159-65.

Frasci, G., et al., "A phase I-II study on a gemcitabine-cyclophosphamide-fluorouracil/folinic acid triplet combination in anthracycline- and taxane-refractory breast cancer patients." Oncology. 2002;62(1 ):25-32.

Fraternale et al., "Repeated cycles of alternate administration of fludarabine and zidovudine plus didanosine inhibits murine AIDS and reduces proviral DNA content in lymph nodes to undetectable levels" Virolgy 2002, 302:354-362.

Freed, et al., "Early Detection of Renal Allograft Rejection by Serial Monitoring of Serum C-Reactive Protein," Transplantation, vol. 37, No. 2, pp. 215-218, Feb. 1984.

Freyer, G., et al .. "Phase II study of oral vinorelbine in first-line advnced breast cancer chemotherapy" J. Clin. Oncol. Jan. 1, 2003;21 (1):35-40. Epub Jan. 1, 2003.

Fu, et al., "CD4+ CD62+ T-Regulatory Cell Subset Has Optimal Suppressive and Proliferative Potential," American Journal of Transplantation, vol. 4, No. 1, pp. 65-78, Jan. 2004.

Fujita et al., "The Value of Acute-Phase Protein Measurements After Curative Gastric Cancer Surgery", Arch. Surg. 1999, 134: 73-75.

Fumoleau, P., et al., "Phase II trial of weekly intravenous vinorelbine in first-line advanced breast cancer chemotherapy." J. Clin Oncol. Jul. 1993;11(7):1245-52.

Fynan et al., "DNA Vaccines: Protective Immunizations by Parenteral, Mucosal, and Gene-Gun Inoculations," Proc. Nat!. Acad. Sci.,, USA, vol. 90, pp. 11478-11482, Dec. 1993.

Gamelin, E, et al., "Long-term weekly treatment of colorector metastic cancer with Fluorouracil andl.leucovorin: results of a multicentric prospective trial of fluoouracil dosage optimization by pharmacokinetic monitoring in 152 patients" J. Clin Oncol., Apr. 1998; 16(4): 1470-8, abstract only, retrieved from the Internet Dec. 19, 2006.

Gaur et al., "Role of a cytotoxic-T-lymphocyte epitope-defined, alternative gag open reading frame in the pathogenesis of a murine retrovirus-induced immunodeficiency syndrome" J Virol 2005, 79(7):4308-4315.

Gavin, Marc A. et al., Homeostasis and Anergy of CD4+CD25+ Suppressor T Cells in Vivo; Dec. 10, 2001; pp. 33-41; V. 3, No. 1; Howard Hughes Medical Institute, University of WaShington; Nature Publishing Group http://immunol.nature.com.

Gebbia V., et al., Paclitaxel and epidoxorubicin or doxorubicin versus cyclophosphamide and epidoxorubicin as first-line chemotherapy for metastatic breast carcinoma: a randomised phase II study, Anticancer Res. Jan.-Feb. 2003; 23(1B): 765-71 retrieved from the Internet Dec. 19, 2006.

Gelinas, et al., "Immunotherapy for Alzheimer's disease," Proceedings of the National Academy of Sciences of the United States of America, vol. 101, No. 2, pp. 14657-14662, Oct. 5, 2004.

George et al., "Immunokinetics of Autoreactive CD4 T Cells in Blood: A Reporter for the "Hit-and-Run" Autoimmune Attack on Pancreas and Diabetes Progression", Journal of Autoimmunity vol. 23 (2004) pp. 151-160.

Ghyka G et al . An Experimental Model Comparing the Antineoplastic and the Immunosuppressive Effects of some Cytostatics. XP-02351730 Archives roumaines de pathologie experimentales et de microbiologie. Romania Jan.-Mar. 1989.

Gibbs, P., et al., "A phase II study of biochemotherapy for the treatment of metastatic malignant melanoma" Melanoma Res. Apr. 2000; 10(2):171-9 retrieved from the Internet Dec. 9, 2006.

Ginopoulos, P., et al., A phase II study with vinorelbine, gemcitabine and cisplatin in the treatment of patients with stage IIIb-IV non-small cell lung cancer (NSCLC). Lung Cancer, Jan. 1999; 23(1):31-7 retrieved ftom the Internet 1219/2006.

Glimelius, B., et al., "Irinotecan combined with bolus 5-f1uorouracil and folinic acid Nordic schedule' as first-line therapy in advanced colorectal cancer" Ann Oncol. Dec. 2002; 13(12):1868-73 retrieved from the Internet Dec. 9, 2006.

Gomez-Bernal, A, et al., "Biweekly docetaxel and vinorelbine in anthracycline-resistant metastatic,~reast cancer: a multicenter phase II study" Am J Clin Oncol., Apr. 2003; 26(2):127-31 retrieved from the Inernet Dec. 19, 2006.

Goorin AM, et al., Phase II/III trial of etoposide and high-dose ifosfamide in newly diagnosed metastatic osteosarcoma: a pediatric oncology group trial. J Clin Oncol. Jan. 15, 2002;20(2):426-33. retrieved from the Internet Dec. 19, 2006.

Gordon. A . et al., Cisplatin Vinblastine and Bleomycin Combination Therapy in Resistant Gestational IB.F./ 4 Trophoblastic Disease, XP-002351699 Cancer. vol. 56. No. 7. 1986 pp. 1407-1410.

Goverman, Tolerance and autoimmunity in TCR transgenic mice specific for myelin basic protein: Immunological Reviews, vol. 169, No. 1, pp. 147-159, Jun. 1999.

Grem, J. L., et al. "Phase II study of fluorouracil, leucovorin, and interferon alfa-2a in metastatic colorectal carcinoma" J. Clin Oncol. Sep. 1993; 11(9): 1737-45.

Guastalla, J. P., et al. "Phase II trial for intraperitoneal cisplatin plus intravenous sodium thisulhate in advanced ovarian carcinoma patients with minimal residual disease after cisplatin-based chemotherapy—a phase II study of the EORTC Gynaecological Cancer Cooperative Grouo" Eur J Cancer. 1994;30AI1\:45-9.

Gundersen S, et al., "interferon in combination with vinblastine in advanced malignant melanoma. A phase I-II study." Cancer. Oct. 15, 1989;64(8):1617-9.

Hamajima et al. (1997) Clin. Immunol. Immunopathol. 83:179-184.

Hartley, Janet W. et al.; Retrovirus-Induced Murine Acquired Immunodeficiency Syndrome: Natural History of Infection and Differing Susceptibility of Inbred Mouse Strains; Mar. 1989; pp. 1223-1231; vol. 63, No. 3; Joumal of Virology; American Society for Microbiology.

Henss, H., et al., "Phase-II study with the combination of cisplatin and doxorubicin in advanced malignant mesothelioma of the pleura." Onkologie. Jun. 1988;11(3):118-20.

Herniou et al., "Retroviral diversity and distribution in vertebrates" J Virol 1998, 72(7):5955-5966.

Hill, et al., "Total Body Irradiation and Acute Graft-Versus-Host Disease: The Role of Gastrointestinal Damage and Inflammatory Cytokines," Blood, vol. 90, No. 8, pp. 3204-3213, Oct. 15, 1997.

Hiroaki Mitsuya et al.; Targeted Therapy of Human Immunodeficiency Virus-Related Disease; Jul.. 1991; 52 pp. 2369-2381; V. 5; The FASEB Journal.

Hiura, et al., "Both Regulatory T Cells and Antitumor Effector T Cells are primed in the same draining lymph nodes during tumor progression", Journal of Immunology, 2005, pp. 5058-5066.

Hofheinz R. D., et al., "High-dose 5-fluorouracil/folinic acid in combination with three-weekly mitomycin C in the treatment of advanced gastric cancer. A phase II study." Onkologie, Jun. 2002;25(3):255-60.

Holcombe et al., "The Immunosuppressive Agent 15-Deoxyspergualin Functions by Inhibiting Cell Cycle Progression and Cytokine Production Following Naïve T Cell Activation", Journal of Immunology, vol. 169, No. 9, pp. 4982-4989, 2002.

Hood et al., "Plant-Based Production of Xenogenic Proteins," Current Opinion in Biotechnology 1999, 10:382-386.

Horvath, Mogdolna. et al. "Investigation of circulating Immune Complexes in Patients with Breast Cancer." Oncology 39: 20-22 (1982).

Hosotsubo et al., "Hyperbilirubinaemia After Major Thoracic Surgery: Comparison Between Open-Heart Surgery and Oesophagectomy," Critical Care, vol. 4, No. 3, http://ccforum.comlcontentl4/3/180.

Hryniewicz et al., "CTLA-4 blockage decreases TGF-B, IDO, and viral RNA expression in tissues of SIV mac251-infected macaques", Blood, vol. 108, No. 12, Dec. 1, 2006.

Huber et al., "Cycling of immune responses to a syngeneic murine mammara adenocarcinoma," Cancer Research, vol. 40 No. 10, pp. 3484-3490 (Oct. 1980).

Hudes, GR, et al., "Phase II trial of 96-hour paclitaxel plus oral estramustine phosphate in metastatic hormone-refractory prostate cancer." J. Clin. Oncol. Sep. 1997; 15(( ):3156-63.

Hughes P.. et al., "Dual Labelling of Circulating CD8 Cells in Pateints with Multiple Sclerosis", Journal of Neuroloav, Neurosurqerv and Psychiatry, Jan. 1989. vol. 52, No. 1.

Hurteloup, P., et al. "Phase II clinical evaluation of doxifluridine." Cancer Treat. Rep. Jun. 1986; ZO(6):731-7.

Ibrahim, N. K., et al., "Phase II study of vinorelbine administered by 96-hour infusion in patients with advanced breast carcinoma." Cancer. Oct. 1, 1999;86(7):1251-7.

Imami et al. (1999) Clin. Exp. Immunol. 118: 78-86.

Imami et al., "Development of immunotherapeutic strategies for HIV-1", Expert Opinion, vol. 1, No. 5, Sep. 2001, pp. 803-816.

Iwashiro et al., "Immunosuppression by CD4+ regulatory T cells induced by chronic retroviral infection" PNAS 2001, 98( 16): 9226-9230.

Jarnicki et al., "Supporession of Antitumor Immunity by IL-10 and TGF-B-Producing T Cells Infiltrating the Growing Tumor: Influence of Tumor Environment on the Induction of CD4+ and CD8+ Regulatory T Cells" The Journal of Immunology, 2006, 177:896-904.

Jeen, YT, et al. "Phase" trial of epirubicin, cisplatin, oral uracil and tegafur, and leucovorin in patients with advanced gastric carcinoma. Cancer. Jun. 15, 2001;91 (12):2288-93.

Jeremic, B., et al., "Carboplatin and etoposide in advanced colorectal carcinoma. A phase study." Cancer. May 1, 1993;71 (9):2706-8.

Jibiki et al. "Tumor markers in testicular tumors," Gan No Rinsho. Japan Journal of Cancer Clinics, Oct. 1985, vol. 31, No. 13, pp. 1709-1716 (Abstract Only).

Jin, Oon Chong, et al., "Adriamycin in the Treatment of Resectible and Irresectible Primary Hepatocellular Carcinoma" Annals Academy of Medicine, Apr. 1980, vol. 9, No. 2.

Jin-Hwang Liu, et al., "Tamoxifen and colchicine-modulated vinblastine followed by 5-fluorouracil in advanced renal cell carcinoma: a phase II study" Science Direct-Urology, vol. 57, Issue 4, Apr. 2001, pp. 650-654.

Johnson, D. H., et al. "Cisplatin, vinblastine, and bleomycin in the treatment of metastatic melanoma: a phase II study of the Southeastern Cancer Study Group." Cancer Treat Rep. Jul.-Aug. 1985;69(7-8):821-4.

Jonuleit, et al., "Identification and Functional Characterization of Human CD4+ CD25+ T Cells with Regulatory Properties Isolated from Peripheral Blood," The Journal of Experimental Medicine, vol. 193, No. 11, pp. 1285-1294, Jun. 4, 2001.

Kakolyris, S, et al., "First-line treatment of metastatic breast cancer with mitoxantrone, vlnorelbine, and carboplatin." Am J. Clin Oncol. Dec. 1999;22(6):568-72.

Kakolyris, S., et al., "A dose-escalation study of oxaliplatin and vinorelbine in patients with advanced solid tumors." Onocology. 2002;63(3):213-8.

Kanai et al. (1996) J. Immunol. 157:3681-3687.

Kapustra et al., "A Plant-Derived Edible Vaccine Against Hepatitis B Virus," The FASEB Joumal, vol. 13, Oct. 1999, pp. 1796-1799.

Keimowitz, "Dementia Improvement With Cytotoxic Chemotherapy: A Case of Alzheimer Disease and Multiple Myeloma," Archives of Neurology, vol. 54, No. 4, pp. 485-488, Apr. 1997.

Kelly, W.K, et al., "Paclitaxel, estramustine phosphate, and carboplatin in patients with advanced prostate cancer." J. Clin Oncol. Jan. 1, 2001;19(1):44-53.

Kikuyama, S., et al. "Phase study of mitomycin C, cisplatin and 5-fluorouracil for advanced and recurrent gastric cancer." Anticancer Res. Nov.-Dec. 2002;22(6B):3633-6.

Kilby, J. Michael MD et al.; Recurrence of the Acute HIV Syndrome After Interruption of Antiretroviral Therapy in a Patient with Chronic HIV Infection: A Case Report; Sep. 19, 2000; pp. 435-438; V. 133(6); Annals of Internal Medicine; American College of Physicians.

Kim, T.W., et al. "Phase II study of capecitabine plus cisplatin as first-line chemotherapy in advanced gastric cancer" Ann On col. Dec. 2002:13(12):1893-8.

Kimura, Motohiko, et al., "Significance of Serum Amyloid A on the Prognosis in Patients with Renal Cell Carcinoma" Cancer 2001; 92:2072-5.

Kindler HL, et al., "Edatrexate (10-ethyl-deaza-aminopterin)(NSC #626715) with or without leucovorin rescue for malignant mesothelioma. Sequential phase II trials by the cancer and leukemia group B." Cancer. 199 Nov. 15;86(10):1985-91.

Kinter et al., "CD25+ CD4+ Regulatory T Cells from the Peripheral Blood of Asymptomatic HIV-infected individuals Regulate CD4+ and CD8+ HIV-specific T Cell Immune Responses in vitro and are associate with favorable clinical markers of disease status", Journal of Experimental Medicine, vol. 200, No. 3, pp. 331-343, Aug. 2, 2004.

Kinter et al., "Suppression of HIV-specific T cell activity by lymph node CD25+ regulatory T cells from HIV-infected individuals", PNAS, vol. 104, No. 9, pp. 3390-3395, Feb. 27, 2007.

Kinter et al., "CD25+ Regulatory T Cells Isolated from IV-Infected Individuals Suppress the Cytolytic and Nonlytic Antibiral Activity of HIV-Specific CD8+ T Cells in Vitro," AIDS Research and Human Retroviruses, vol. 23, No. 3, pp. 438-450, 2007.

Kjorstad, K., et al., "A multicenter phase II study of carboplatin in advanced ovarian carcinoma: final report" Ann Oncol. Mar. 1992;3(3):217-22.

Knoechel et al., "Sequential development of interleukin 2-dependent effector and regulatory T cells in response to endogenous systemic antigen", JEM, vol. 202, Nov. 21, 2005, 12 pages.

Kohm, et al., "CD4+ CD25+ Regulatory T Cells Suppress Antigen-Specific Autoreactive Immune Responses and Central Nervous System Inflammation During Active Experimental Autoimmune Encephalomyelitis," The Journal of Immunology, vol. 169, No. 9, pp. 4712-4716, Nov. 1, 2002.

Kollmannsberger, C., et al. "A phase II study of paclitaxel, weekly, 24-hour continous infusion 5-fluorouracil, folinic acid and cisplatin in patients with advanced gastric cancer." Br. J. Cancer. Aug. 2000;83(4):458-62.

Kornek, G. V., et al. Effective combination chemotherapy with paclitaxel and cisplatin with or without human granulocyte colony-stimulating factor and/or erythropoietin in patients with advanced gastric cancer. Br. J. Cancer. Jun. 17, 2002; 86(12):1858-63.

Kornek, G. V.,et al., "Effective treatment of advanced breast cancer with vinorelbine, 5-ftuorouracil and 1-leucovorin plus human granulocy1e colong-stimulating tactor." Br. J. Cancer. Sep. 1998;78(5):673-8.

Kosmas, C., et al. Phase I-II study of docetaxel and ifosfamide combination in patients with anthracycline pretreated advanced breast cancer. Br J Cancer, Apr. 22, 2003;88(8):1168-74.

Kouroussis, C., et al. Oxaliplatin in combination with infusional 5-ftuorouracil and leucovorin every 2 weeks as first-line treatment in patients with advanced colorectal cancer: a phase II study. Oncology. 2001;61(1):36-41.

Kruse et al., "Analysis of Interleukin 2 and Various Effector Cell Populations in Adoptive Immunotherapy of 9L Rat Gliosarcoma: Allogeneic Cytotoxic T Lymphocytes Prevent Tumor Taken," Proc. Natl. Acad. Sci, USA, vol. 87, pp. 9577-9581, Dec. 1990.

Kukreja, et al., "Autoimmunity and Diabetes," The Journal of Clinical Endocrinology & Metabolism, vol. 84, No. 12, pp. 4371-4378, Dec. 1999.

Lage et al. "New insights on how nucleotide excision repair could remove DNA adducts induced by chemotherapeutic agents and psoralens plus UV-A (PUVA) in *Escherichia coli* cells." Mutation Research/Reviews in Mutation Research, Nov. 2003, vol. 544, No. 2-3, pp. 143-157 (Abstract Only).

Leung, T. W., et al., "Complete pathological remission is possible with systemic combination chemotherapy for inoperable hepatocellular carcinoma" Clin Cancer Res. Jul. 1999; 5(7):1676-81.

Lewis "Oxidative stress: the role of cytochromes P450 in oxygen activation," Journal of Chemical Technology and Biotechnology, Oct. 2002, vol. 77, No. 10, pp. 1095-1100 (Abstract Only).

Li, J. D., et al. "[Phase II clinical study of topotecan hydrochloride in patients with recurrent advanced ovarian cancer]" Ai Zheng. Apr. 2002;21(4):416-20.

Liang et al., "Murine AIDS, a key to understanding retrovirus-induced immunodeficiency" ViralImmunol1996, 9 (4):225-239; Abstract only. PMID: 8978019; PubMed, Indexed for MEDLINE.

Lifson. Jeffrey D. et a/.; Containment of Simian Immunodeficiency Virus Infection: Cellular Immune Responses and Protection from Rechallenge following Transient Postinoculation Antiretroviral Treatment; Mar. 2000; DP. 2584-2593; V. 74. No. 6; Journal of vtrotocv: American Society of Microbiology.

Lim et al., "Cell surface markers of regulatory T cells are not associated with increased forkhead box p3 expression in blood CD4+ T cells from HIV-infected patients responding to antiretroviral therapy", Immunology and Cell Biology, 2006, 84, 530-536.

Lim et al., "Proportions of circulating T cells with a regulatory cells phenotype increase with HIV-associated immune activation and remain high on antiretroviral therapy," AIDS 2007, vol. 21, pp. 1525-1534.

Lissoni, A., et al. "Phase II study of paclitaxel as salvage treatment in advanced endometrial cancer" Ann Oncol., Oct. 1996;7(8):861-3.

Little et al., "Systemic chemotherapy for HIV-associated lymphoma in the era of highly active antiretroviral therapy," Current Opinion in Oncology, Vo 12 No. 5, pp. 438-444 (Sep. 2000).

Liuzzo, et al. The Prognostic Value of C-Reactive Protein and Serum Amyloid A Protein in Servere Unstable Angina, The New England Journal of Medicine, vol. 331(7) Aug 18, 1994.417-424.

Logothetis. Christopher J .. et al., "Cyclic Chemotherapy with Cyclophosphamide. Doxorubicin, and Cisplatin Plus Vinblastine and Bleomycin in Advanced Germinal tumors" Aug. 1986 The American Journal of Medicine. vol. 81. p. 219-227 XP-002351698.

Lori et al., "Hydroxyurea and HIV: 5 years later—from antiviral to immune-modulating effects", AIDS (London, England) Aug. 20, 1999, vol. 13, No. 12, pp. 1433-1442.

Lori et al., "Targeting HIV Reservoirs and reconstituting the immune system", AIDS research and human Retroviruses, vvol. 15, No. 18, 1999, pp. 1597-1617.

Lorusso, P., et al., Low-dose continuous infusion 5-fluorouracil and cisplatin: phase II evaluation in advanced colorectal carcinoma. Am J Clin Oncol. Dec. 1989;12(6):486-90.

Lotem, M., et al., "Interleukin-2 improves tumour response to DNP-modified autologous vaccine for the treatment of metastatic malignant melanoma" British Journal of Cancer (2004) 90, 773-780.

Louvet C., et al. "Phase II study of oxaliplatin, fluorouracil, and folinic acid in locally advanced or metastatic gastric cancer patients" J. Clin Oncol. Dec. 1, 2002;20(23):4543-8.

Lundholm, Peter, "Immune and Autoimmune Responses to HIV-1 in Mucosa and Other Tissues" The Swedish Institute for Infectious Disease Control, Oct. 29, 1999, kl 9.00.

Lutsiak, M. E. Christine, et ai, Inhibition of CD4+25+ T Regulatory Cell Function Implicated in Enhanced Immune Response by Low Dose Cyclophosphamide, Blood 1st Ed paper, pre published online Dec. 19, 2004; DOI 10.1182/blood-2004-06-2410

Mahmoud et al., "The Role of C-Reactive Protein as a Prognostic Indicator in Advanced Cancer," Current Oncology Reports 2002 4:250-255.

Manetta A., et al., "Cyclosporin enhancement of cisplatin chemotherapy in patients with refractory gynecologic cancer. A Gynecologic Oncology Group Study." Cancer. Jan. 1, 1994;73(1):196-9.

Marchand. Marie. at el., "Tumor Regressions Observed in Patients with Metastatic Melanoma Treated with an Antigenic Peptide Encoded by Gene Mage-3 and Presented by HLA•A" XP-002305439 International Journal of Cancer, New York, NY, vol. 80, No. 2, Jan. 19, 1999, pp. 219-230.

Mariotta, S., et al., "Combined treatment in advanced stages (1IIb-IV) of non-small cell lung cancer." Eur Rev Med Pharmacol Sci. Mar.-Jun. 2002 ;6(2-3):49-54.

Mason et al., "Expression of Norwalk Virus Capsid Protein in Transgenic Tobacco and Potato and its Oral Immunogenicity in Mice," Proc. Natl. Acad. Sci. USA, vol. 93, pp. 5335-5340, May 1996.

Maury, et al., "Comparative study of serum amyloid-related protein SAA, C-reactive protein, and B2-microglobulin as markers of renal allograft rejection," Clinical Nephrology, vol. 22, No. 6, pp. 284-292, date unknown.

Mbidde, E.K., et al., "Phase II trial of carboplatin (JM8) in reatment of patients with malignant mesothelioma." Cancer Chemother Pharmacol. 1986; 18(3):284-5.

McClay, E. F., et al., "A Phase II trial of intraperitoneal high-dose carboplatin and etoposide with granulocyte macrophage-colony stimulating factor support in patients with ovarian carcinoma." Am J. Clin Oncol. Feb. 1995;18(1 ):23-6.

McGuirk, Peter et al.; Pathogen-Specific Regulatory T Cells Provoke a Shift in the Th1/Th2 Paradigm in Immunity to Infectious Diseases; Sep. 2002; pp. 450-455; V. 23 No. 9; Trends in Immunology; Elsevier Science Ltd.

McMillan et al. Disease of the Colon & Rectum 1997; 40: 1068-1071.

McMillan et al. The American Journal of Surgery 1995, 170:319-322.

Medline Abstract Accession No. PMID 10228499; Aversa, S.M., et al.; Tumori; Jan.-Feb. 1999,85(1),54-59.

Medline Abstract Accession No. PMID 10950369; Dezube, B.J.; Semin Oneal; Aug. 2000,27(4),424-430.

Medline Abstract Accession No. PMID 8959247; Zanussi, S., et al.; AIDS Res Hum Retroviruses; Dec. 10, 1996; 12(18), 1703-1707.

Medstrand et al., "Characterization of Novel Reverse transcriptase encoding human endogenous retroviral sequences similar to type A and type B retroviruses: Differential transcription in normal human tissues", Journal of Virology, Nov. 1993, vol. 67, No. 11, pp. 6778-6787.

Mehigan et al. Changes in T cell subsets, interleukin-6, and C-reactive protein after laparoscopic and open colorectal resection for malignancy, Surg. Endosc. 2001; 15:1289-1293.

Melchior. J. et al., "Malnutrition and Wasting, Immunodepression, and Chronic Inflammation as Independent Predictors of Survival in HIV-Infected Patients", Nutrition, Nov.-Dec. 1999, vol. 15, No. 11/12, pp. 865-869.

Meropol, N. J., et al. "Phase II study of oral eniluracil, 5-fluorouracil, and leucovorin in patients with advanced colorectal carcinoma." Cancer. Apr. 1, 2001;91(7):1256-63.

Michelotti, A., et al., "Paclitaxel in combination with venorelbine in pretreated advanced breast cancer patients." Semin Oncol. Oct. 1996;23(5 SupplII):38-40.

Miller et al., "Human immunodeficiency virus and AIDS: insights from animal lentiviruses" J Virol 2000, 74 D (16):7187-7195.

Ming, Meng et al., "Studies on Development of Treatment against Retroviruses," Journal of Hebei Occupational Institute of Medical Science, 1997, No. 1, pp. 22-25.

Miyazono et al. "Surgical Maneuvers Enhance Molecular Detection of Circulating Tumor Cells During Gastric Cancer Surgery", Annals of Surgery 2001, 233: 189-194.

Modelska et al., "Immunization Against Rabies With Plant-Derived Antigen," Proc. Nat!. Acad. Sci. USA, vol. 95, pp. 2481-2485, Mar. 1998.

Monnet I., et al., "Intrapleural infusion of activated macrophages and gamma-interferon in malignant pleural mesothelioma: a phase II study." Chest. Jun. 2002;121('):1921-7.

Monsonego, et al., "Immunotherapeutic Approaches to Alzheimer's Disease," Science, vol. 302, pp. 834-838, Oct. 31, 2003.

Montgomery et al., "Heterologous and Homologous Protection Against Influenza A by DNA Vaccination: Optimization of DNA Vectors," DNA and Cell Biology, vol. 12, No. 9, 1993, pp. 777-783.

Moore, John P. et al.; MINIREVIEW Genetic Subtypes. Humoral Immunity. and Human Immunodeficiency Virus Type 1 Vaccine Development; Jul. 2001; pp. 5721-5729; V. 75, No. 13; Journal of Virology; American Society for Microbiology.

Morabito A., etal., "The combination of gemcitabine and vinorelbine is an active regimen as second-line therapy in patients with metastatic breast cancer pretreated with taxanes and or anthracyclines: a phase I-II study." Breast Cancer Res Treat. Mar. 2003; 78(li:29-36.

Morgan, et al., "CD25+ Cell Depletion Hastens the Onset of Severe Disease in Collagen-Induced Arthritis," Arthritis & Rheumatism, vol. 48, No. 5, pp. 1452-1460, May 2000.

Morris, M., et al., "Phase II study of vinorelbine in advanced and recurrent squamous cell carcinoma of the cervix" J. Clin Oncol. Mar. 1998;16(3):1094-8.

Morse et al., "Retrovirus-induced immunodeficiency in the mouse: MAIDS as a model for AIDS", AIDS, 1992, vol. 6, pp. 607-621.

Mortensen, "C-Reactive Protein, Inflammation, and Innate Immunity", Immunologic Research, 2001, vol. 24, No. 2, pp. 163-176.

Murad, A.M., "Phase II trial of the use of gemcitabine and 5-fluorouracil in the treatment of advanced pancreatic and biliary tract cancer." Am J Clin Oncol. Apr. 2003;26(2):151-4.

Murad, A.M., et al., "Phase II trial of the combination of paclitaxel and 5-fluorouracil in the treatment of advanced gastric cancer: a novel, safe, and effective regimen." Am J Clin Oncol. Dec. 1999;22(6):580-6.

Murphy, et al., "New strategies for preventing graft-versus-host disease," Current Opinion in Immunology, vol. 11, No. 5, pp. 509-515, Oct. 1, 1999.

Musk et al., "Conventional Treatment and its Effect on Survival of Malignant Pleural Mesothelioma in Western Australia," Aust. N.Z. J. Med. (1982) 12, pp. 229-232.

Nasti et al. "A risk and benefit assessment of treatment for AIDS-related Kaposi's sarcoma" Drug Safety, May 1999; 20(5):403-425.

Nathan F. E., et al., "Paclitaxel and tamoxifen: An active regimen for patients with metastatic melanoma" Cancer Jan. 1, 2000;88(1):79-87.

Neri B., "Results of leucovorin and doxibluridine oral regimen in the treatment of metastatic colorectal cancer" Anticancer Drugs. Aug. 1998;9(7):599-602.

Neri, B., et al. "Raltitrexed plus oxaliplatin as first-line chemotherapy in metastatic colorectal carcinoma: a multicentric phase II trial." Anticancer Drugs. Aug. 2002;13(7):719-24.

Nilsson, Jakob, et al., "HIV-1-driven regulatory T-cell accumulation in lymphoid tissues is associated with disease progression in HIV/AIDS" Blood, Dec. 1, 2006, vol. 108, No. 12 pp. 3808-3817.

North, Robert J., "The Murine Antitumor Immune Response and Its Therapeutic Manipulation," Advances in Immunology, 1984, vol. 35, pp. 89-155.

North, et al., "Generation and Decay of the Immune Response to a Progressive Fibrosarcoma," J. Exp. Med., May 1984, vol. 159, pp. 1295-1311.

North, R.J. and Awward, A. (1990) Elimination of cycling CD4 suppressor T cells with an anti-mitotic drug releases non-cycling CD8 T cells to cause regression of an advanced lymphoma. Immunology 71:90-95.

Nystrom, M.I. et al. "Low-dose continuous chemotherapy for metastatic melanoma: a phase II trial" Melanoma Res. Apr. 2003;13(2):197-9.

O'Brien et al. "Changes in Plasma HIV-1 RNA and CD4+ Lymphocyte Counts and the Risk of Progression to AIDS." The New England Journal of Medicine, Feb. 15, 1996, vol. 334, No. 7, pp. 426-431.

O'Hanlon, Deirdre M. et al., "The Acute Phase Response in breast Carcinoma" Anticancer Research 22:1289-1294 (2002).

O'Hara, Rosemary, et al., "Acute-phase serum amyloid A production by rheumatoid arthritis synovial tissue" Arthritis Res 2000,2:142-144.

Okuno, S.H., et al., "Phase II study of methotrexate, vinblastine, doxorubicin, and cisplatin in patients with squamous cell carcinoma of the upper respiratory or alimentary passages of the head and neck" Cancer Apr. 15, 2002;94(8):2224-31.

Onizuka et al. "Tumor Rejection by in Vivo Administration of Anti-CD25 (Interleukin-2 Receptor a) Monoclonal Antibody", Cancer Research 1999; 59:3128-3133.

Orenstein R "Looking beyond highly active antiretroviral therapy: drug-related hepatotoxicity in patients with human immunodeficiency virus infection" Pharmacotherapy vol. 22(2002) pp. 1468-1478.

Ortiz, Gabriel M. et al.; HIV-1-Specific Immune Responses in Subjects Who Temporarily Contain Virus Replication After Discontinuation of Highly Active Antiretroviral Therapy, Aug. 16, 1999; V. 0, No. 1999; J. Clin Invest.; American Society for Clinical Investigation.

Ozols, RF., et al., "Phase II trial of 5-FU administered Ip to patients with refractory ovarian cancer." Cancer Treat Rep. Oct. 1984;68(10):1229-32.

Paccagnella, A., et al. "Mitomycin C., vinblastine, and carboplatin regimen in patients with nonsmall cell lung cancer. A phase II trial." Cancer. Oct. 15, 1996; 78(8):1701-7.

Patt, Y. Z., et al. "Phase II trial of systemic continosus fluorouracil and subcutaneous recombinant interferon Alfa-2b for treatment of hepatocellular carcinoma" J. Clin Oncol. Feb. 1, 2003; 21 (3):421-7.

Payelle B.. et al., "Role of T Suppressor Cells in the Cycling of the Immune Response Against a Murine Fibrosarcoma", International Journal of Cancer. Jul. 15, 1984, vol. 34, No. 1, pp. 95-100.

Pectasides, D., et al. "First line cominbation chemotherapy with docetaxel and vinorelbine in advanced breast cancer. A phase II study." Anticancer Res. Sep.-Oct. 2001;21(5):3575-80.

Pepys, et al., "C-reactive protein: a critical update," The Journal of Clinical Invesigation, vol. 111, No. 12, pp. 1805-1812, Jun. 2003.

Perng, R P., et al. "A phase II trial of vinorelbine and cisplatin in previously untreated inoperable non-small-cell lung cancer." Am J Clin Oncol. Feb. 2000;23(1):60-4.

Peterson, Karin E., et al., "Novel Role of CD8+ T Cells and Major Histocompatibility Complex Class I Genes in the Generation of Protective CD4+ Th1 Responses during Retrovirus Infection in Mice" Journal of Virology, Aug. 2002, vol. 76, No. 16, O. 7942-7948.

Petrelli, NJ, et al. "Combination chemotherapy of cisplatin and 5-fluorouracil for advanced colorectal adenocarcinoma" Cancer Chemother Pharmacol. 1989;23(1):57-60.

Picus J., et al., "Docetaxel (Taxotere) as monotherapy in the treatment of hormone-refractory prostate cancer: preliminary results" Semin Oncol. Oct. 1999;26(5 Suppl17):14-8.

Pinto C., et al., "Combination chemotherapy with mitoxantrone, methotrexate, and mitomycin (MMM regimen) in malignant pleural mesothelioma: a phase II study." Am J Clin Oncol. Apr. 2001; 24(2):143-7.

Plana, M. et al. (2000) Immunological benefits of antiretroviral therapy in very early stages of asymptomatic chronic HIV-1 infection. AIDS 14:1921-1933. See abstract, Introduction 1st paragraph, Materials and Methods and last paragraph of the Discussion.

Planner R. S., et al., "Paclitaxel (Taxol) as salvage therapy for relapsed ovarian cancer" Aust N. Z. J. Obstet Gynaecol. May 1996; 36(2):168-70.

Planting A.S., et al., "Phase II study of a short course of weekly high-dose cisplatin combined with long-term oral etoposide in pleural mesothelioma" Ann Oncol. Jul. 1995:6(6): 613-5.

Pohl, J., et al., "Systemic chemotherapy with epirubicin for treatment of advanced or multifocal hepatocellular carcinoma" Chemotherapy. Sep.-Oct. 2001; 47(5)359-65.

Porta C., et al., "5-Fluorouracil and d,l-leucovorin calcium are active to treat unresectable hepatocellular carcinoma patients: preliminary results of a phase II study." Oncology, Nov.-Dec. 1995;52(6):487-91.

Posner, M., et al., "A phase II trial of continuous infusion cisplatin and 5-fluorouracil with oral calcium leucovorin in colorectal carcinoma" Am J. Clin Oncol. Jun. 1992; 15(3):239-41.

Price et al., "Development and Validation of a Particle-Enhanced Turbidimetric Immunoassay for C-reactive Protein," Journal of Immunological Methods, 99 (1987) 205-211.

Pyrhonen SO, et al., "Phase II study of epirubicin sequential methotrexate and 5-fluorouracil for advanced colorectal cancer" Eur J Cancer 1992;28A(II):1828-32.

Quevedo, et al., "Possible therapeutic reversal of immune suppression in patients with metastatic melanoma by timed delivery of temozolomide chemotherapy: A pilot study," Journal of Clinical Oncology, 2009, vol. 27, No. 155 (May 20 supplement), e20013.

Racke et al., "Intravenous Antigen Administration as a Therapy for Autimmune Demyelinating Disease", Annals of Neurology, vol. 39, No. 1, pp. 46-56, 1996.

Raghavan D, et al., "Phase II trial of carboplatin in the management of malignant mesothelioma" J Clin On col. Jan. 1990;8(1):151-4.

Rakowicz-Szulczynska, Eva M. et al.; Human Immunodeficiency Virus Type 1-Like DNA Sequences and Immunoreactive Viral Particles with Unique Association with Breast Cancer; Sep. 1998; pp. 645-653; V. 5, No. 5; Clinical and Diaanostic Laboratory Immunoloav; American Society for Microbioloav.

Rakowicz-Szulczynska, Eva M.; Relevance of the Viral RAK Alpha Gene in Diagnosis of Malignant Versus Nonmalignant Tumors of the Ovary and Uterus; May 2000; pp. 360-365; V. 7, No. 3; Clinical and Diagnostic Laboratory Immunology; American Society for Microbiology.

Read et al., "CD4+ regulatory T cells" Curr Opin Immunol 2001, 13:644-649.

Read, Simon, et al., "Cytotoxic T Lymphocyte-associated Antigen 4 Plays an Essential role in the Function of CD25+CD4+ Regulatory Cells that control Intestinal Inflammation," J. Exp. Med. The Rockefeller University Press vol. 192, No. 2, Jul. 17, 2000 295-302.

Recchia F, et at "Gemcitabine, ifosfamide and vinorelbine in advanced non-small cell lung cancer: a hase II study" Anticancer Res. Mar.-Apr. 2002;22(2B):1321-8.

Reina JJ, et al., "A multicenter phase II study of irinotecan (CPT-II) alternated with 5-fluorouracil and leucovorin as first-line treatment of patients with metastatic colorectal cancer" cancer chemother Pharmacol. Oct. 2003;52141:339-45. Eoub Jul. 8, 2003.

Retsas S, et al, "Taxol and venorelbine: a new active combination for disseminated malignant melanoma" Anticancer Drugs, Feb. 1996; 7(2):161-5.

Rodriguez-Galindo C, et al., "Treatment of refractory osteosarcoma with fractionated cyclophosphamide and etoposide" J Pediatr Hematol Oncol. May 2002;24(4):250-5.

Romero A 0, "Double modulation of 5-fluorouracil by methotrexate and high-dose L-leucovorin in advanced colorectal cancer" Am J Clin Oncol. Feb. 1998;21(1):94-8.

Romero A, et al., Vinorelbine as first-line chemotherapy for metastatic breast carcinoma J Clin Oncol, Feb. 1994;12(2):336-41.

Rose PG, et at, "A phase II study of docetaxel in paclitaxel-resistant ovarian and peritoneal carcinoma: a Gynecologic Oncology Group study" Gynecol Oncql. Feb. 2003;88(2):130-5.

Rosenthal MA, et al., "Phase II study of combination taxol and estramustine phosphate in the treatment of recurrent glioblastoma multiforme" J Neurooncol. Mar. 2000;47(1):59-63.

Rossi et al., "Inhibition of murine AIDS by a heterodinucleotide of azidothymidine and 9-(R)-2-(phosphonomethoxypropyl)adenine" J Antimicrobial Chemo 2002,50:639.

Rouse et al., "Regulatory T Cells in virus infections" Immunol Rev 2006, 212:272-286.

Safran H, et al., "Gemcitabine, paclitaxel, and radiation for locally advanced pancreatic cancer: a Phase II trial." Int J Radiat Oncol Biol Phys. Sep. 1, 2002;54(1):137-41.

Sahni et al., "Hiv Vaccine Strategies—an Update," Armed Forces Medical College, vol. 60, No. 2, 2004, pp. 157-164.

Sakaguchi et al., "Regulatory T cells: key controllers of immunologic self-tolerance" Cell 2000, 101:455-458.

Sakaguchi, Shimon, et al., "Immunologic tolerance maintained by CD25+ CD4+ regulatory T cells: their common role in controlling autoimmunity, tumor immunity, and transplantation tolerance" vol. 182, Aug. 2001, pp. 18-32.

Sakata Y, et al. "Late phase II study of novel oral fluoropyrimidine anticancer drug S-1 (1 M tegafU~,O.4 M gimestat-I M otastat potassium) in advanced gastric cancer patients." Eur J Cancer. Oct. 1998;34(11:1715-20.

Salomon et al., "B7/CD28 Costimulation is Essential for the Homeostasis of the CD4+ CD25+ Immunoregulatory T Cells that Control Autoimmune Diabetes," Immunity, vol. 12,431-440, Apr. 2000.

Santamaria, "Effector lymphocytes in autoimmunity," Current Opinion in Immunology, vol. 13, No. 6, pp. 663-669, Dec. 1, 2001.

Savarese 0, et al., "A phase II study of docetaxel (Taxotere), estramustine, and low-dose hydrocortisone in men with hormone-refractory prostate cancer: preliminary results of cancer and leukemia group B Trial 9780" Semin Oncol. Oct. 1999;26(5 Suppl17):39-44.

Savarese OM, et al. Phase II study of docetaxel, estramustine, and low-dose hydrocortisone in men with hormone-refractory prostate cancer: a final report of CALGB 9780. Cancer and Leukemia Group B. J Clin Oncol. May 1, 2001;19(9):2509-16.

Sawamura, M., et al., "Cyclic Haemopoiesis at 7- or 8-day Intervals", British Journal of Haematology, 88:215-18 (1994).

Scheithauer, W., et al. "Intermittent weekly high-dose capecitabine in combination with oxaliplatin: a phase 111I study in first-line treatment of patients with advanced colorectal cancer" Ann Oncol. Oct. 2002;13(10):1583-9.

Schornagel JH, et al., "Phase II study of recombinant interferon alpha-2a and vinblastine in advanced renal cell carcinoma" J Urol. Aug. 1989;142(2 Pt 1):253-6.

Sedegah et al., "Protection Against Malaria by Immunization With Plasmid DNA Encoding Circumsporozoite Protein," Proc. Natl. Acad. Sci., vol. 91, pp. 9866-9870, Oct. 1994.

Sehouli, J., et al., "A phase II study of topotecan plus gemcitabine in the treatment of patients with relapsed ovarian cancer ater failure of first-line chemotherapy" Ann Oncol. Nov. 2002;13(11):1749-55.

Senju, Osamu, "Latex Agglutination Photometric Assay (LA-System)" JJCLA vol. 8, No. 1, 1983, p. 161-165.

Zhang et al., "Studies on the Progress in the Development of AIDS Vaccines," Immunological Journal, vol. 16, No. 4, Jul. 2000, S72-74 (Abstract).

Shepherd FA et al. "Combination chemotherapy and a-inteferon in the treatment of Kaposi's sarcoma associated with acquired immune deficiency syndrome" CMAJ 139 (1988):635-639.

Sherman WH, et al., "Combination gemcitabine and docetaxel therapy in advanced adenocarcinoma of the pancreas." Oncology. 2001;60(4):316-21.

Shih et al., "Detection of Multiple, Novel Reverse Transcriptase Coding Sequences in Human Nuclei Acids: Relation to Primate Retroviruses," Journal of Virology, Jan. 1989, vol. 63, No. 1, pp. 64-75.

Shimizu et al., "Stimulation of CD25+ CD4+ Regulatory T Cells Through GITR Breaks Immunological Self-Tolerance," Nature Immunology, vol. 3, No. 2, Feb. 2002, pp. 135-142, http://Immunol.nature.com.

Shimizu J, et al. "Induction of tumor immunity by removing CD25+CD4+ T cells: a common basis between tumor immunity and autoimmunity" J Immunol. Nov. 15, 1999; 163(10):5211-8.

Simpson, et al., "Cell-Mediated Response to Tumour Xenografts in Mice," International Journal of Cancer, Mar. 1972, vol. 9, No. 2, pp. 299-304.

Sinnige, H. A., et al. "Modification of 5-nuorouracil activity by high-dose methotrexate or leucovorin in advanced colorectal carcinoma" Eur J Cancer. 1990;26(5):625-8.

Small EJ, et al., "Docetaxel, estramustine, plus trastuzumab in patients with metastatic androgen-independent prostate cancer" Semin Oncol. Aug. 2001; 28(4 Suppl15):71-6.

Smith, et al., "Use of Two-Dimensional Gel Electrophoresis to Measure Changes in Synovial Fluid Proteins from Patients with Rheumatoid Arthritis Treated with Antibody to CD4," Clinical and Diagnostic Laboratory Immunology, vol. 8, No. 1, pp. 105-111, Jan. 2001.

Smithers, Mark, et al., "Clinical response after intradermal immature dendritic cell vaccination in metastatic melanoma is associated with immune response to particulate antigen" Cancer Immunol Immunother (2003) 52: 41-52.

Sobrero AF, et al., "Schedule-selective biochemical modulation of 5-nuorouracil: a phase II study in advanced colorectal cancer" Clin Cancer Res, Sep. 1995; 1(9):955-60.

Speiser, et al., "TNF Receptor p55 Controls Early Acute Graft-Versus-Host Disease," The Journal of Immunology, vol. 158, No. 11, pp. 5185-5190, Jun. 1, 1997.

Stathopoulos GP, et al., Phase II trial of biweekly administration of vinorelbine and gemcitabine in pretreated advanced breast cancer, J Clin Oncol. 2002.

Stott. J. et al.; Candidate Vaccines Protect Macaques Against Primate Immunodeficiency Viruses; 1998; pp. S-265-S-270; V. 14. Suppl. 3; AIDS Research and Human Retroviruses; Mary Ann Liebert. Inc.

Sugimachi, K., et al., A phase II trial of a new 5-nuorouracil derivative, BOF-A2 (Emitefur), for patients with advanced gastric cancer. Surg Today. 2000; 30(12):1067-72 (abstract only).

Suri-Payer et al., "Differential Cytokine Requirements for Regulation of Autoimmune Gastritis and Colitis by CD4+ CD25+ T Cells," Journal of Autoimmunity (2001) 16, 115-123.

Suri-Payer, et al., "CD4+CD25+ T Cells Inhibit Both the Induction and Effector Function of Autoreactive T Cells and Represent a Unique Lineage of Immunoregulatory Cells," The Journal of Immunology, vol. 160, pp. 1212-1218, D Feb. 1998.

Susumu et al. "Involvement of lipid peroxidation in the alteration of protein kinase c signaling." Acta Histochemica et Cytochemica, 2003, vol. 36, No. 4, pp. 281-285 (Abstract Only).

Sutmuller et al., "Synergism of Cytotoxic T Lymphocyte-associated Antigen 4 Blockade and Depletion of CD25+IB.F 1 Regulatory T Cells in Antitumor Therapy Reveals Alternative Pathways for Suppression of Autoreactive .Cytotoxic T Lymphocyte Responses," J. Exp. Med. vol. 194, No. 6. Sep. 17. 2001. 823-832, http://www.jem.org/cgUcontentlfulll194/6/823.

Sutton GP, et al., A phase II trial of ifosfamide and mesna in patients with advanced or recurrent mixed mesodermal tumors of the ovary previously treated with platinum-based chemotherapy: a Gynecologic Oncology Group study. Gynecol Oncol. Apr. 1994; 5311\:24-6.

Takahashi et al., "Immunologic Self-Tolerance Maintained by CD25+ CD4+ Regulatory T Cells Constitutively Expressing Cytotoxic T Lymphocyte-Associated Antigen 4," J. Exp. Med . vol. 192. No. 2. Jul. 17, 2000.303-309. http://www.jem.org/cgilcurrentifull/192121303.

Takahashi, Takeshi; Immunologic Self-Tolerance Maintained by CD20 CD4' Naturally Anergic and Suppressive T Cells: Induction of Autoimmune Disease by Breaking Their Anergic/Suppressive State; Sep. 10, 1998; DO. 1969-1980; V. 10, No. 12; International Immunology; Japanese Society for Immunology.

Takeuchi S., et al. [A late phase II study of CPT-llon uterine cervical cancer and ovarian cancer. Research Groups of CPT-II in Gynecologic Cancers] Gan to Kagaku Ryoho. Aug. 1991;18(10):1681-9.

Tan et al., "Evaluation of natural products as inhibitors of human immunodeficiency virus type 1 (HIV-1) reverse transcriptase" Journal of Natural Products, vol. 54, No. 1, 1991, pp. 143-154.
Tawa. A. et al., "Rhabdomyosarcoma of the Urinary Bladder. Complete remission induced by Vinblastine. cis-platinum. and Bleomycin" XP.o02351700 Gan to Kagaku Ryoho Japan. Dec. 1982.
Thomas, G.W., et al., 'Vincristine with high-dose etoposide in advanced breat cancer: a phase II trial of the Piedmont Oncology Association. Cancer Chemother Pharmacol. 1994;35(2):165-8.
Toniatti, C., et al., Regulation of the Human C-Reactive Protein Gene A Major Marlier of Inflammation and Cancer. XP-002351697. 1990. Molecular Biology and Medicine. vol. 7. No. 3. 1990. pp. 199-212.
Trefzer, Uwe, et al., "Vaccination with Hybrids of Tumor and Dendritic Cells Induces Tumor-Specific T-Cell and Clinical Responses in Melanoma Stage III and IV Patients" Int. J. Cancer: 110,730-740 (2004).
Trivedi C., et al., Weekly t-hour infusion of paclitaxel .. clinical feasibility and efficacy in patients with hormone-refractory prostate carcinoma. Cancer, Jul. 15, 2000;89(2):431-6.
Trudeau_et al. "Prediction of spontaneous autoimmune diabetes in NOD mice by quantification of autoreactive T cells in peripheral blood," The Journal of Clinical Investigation, Jan. 2003, vol. 111, No. 2, pp. 217-223.
Tsavaris N, et al., Combination chemotherapy with cisplatin and/or doxorubicin in malignant mesothelioma. A aretrospective study [corrected from prospective]. Anticancer Res. Sep.-Oct. 1997;17(5B):3799-802.
Twelves, CJ, et al., A phase II, multicentre, UK study of vinorelbine in advanced breast cancer. Br J Cancer Nov. 1994;70(5):990-3.
Ulmer et al., "Heterologous Protection Against Influenza by Injection of DNA Encoding a Viral Protein", Science. Mar. 19, 1993, vol. 259. No. 5102. pp. 1745 (5 pages).
Vahlenkamp et al., "Feline Immunodeficiency Virus infection phenotypically and functionally activates immunosuppressive CD4+CD25+ T Regulatory Cells", Journal of Immunology, 2003, pp. 4752-4761.
Vahlenkamp et al., "The role of CD4+ CD25+ regulatory T cells in viral infections", Veterinary immunology and Immunopathology, vol. 108, pp. 219-225, 2005.
Valdivieso M., et al., Broadphase II study of vindesine. Cancer Treat Rep. Sep.-Oct. 1981;65(9-1 0):877-9.
Verma, et al., "Role of MHC class I expression and CD8+ T cells in the evolution of iodine-induced thyroiditis in NOD-H2h4 and NOD mice," European Journal of Immunology, vol. 30, pp. 1191-1202, 2000.
Von Herrath Matihias et al., "Antigen-induced Regulatory T Cells in Autoirnrnunity", iNature Reviews. Imrnunoloqv, Mar. 2003, vol. 3, No. 3, pp. 223-232.
Wang et al., "Detection of Mammary Tumor Virus ENV Gene-like Sequences in Human Breast Cancer", Cancer Research 55, 5173-5179, Nov. 15, 1995.
Wang et al., "Gene Inoculation Generates Immune Responses Against Human Immunodeficiency Virus Type 1," Proc. Natl. Acad. Sci. USA. vol. 90. pp. 4156-4160. May 1993.
Weinstein, P. S.. et al., "Acute-Phase Proteins or Tumour Markers: The Role of SAA, SAP, CRP and CEA as Indicators of Metastasis in a Broad Spectrum of Neoplastic Disease" Scand. J. Immunol. 19, 193-198, 1984.
Weiss. Laurence. et al .. "Human immunodeficiency virus—driven expansion of CD4+ CD25+ regulatory T cells. which suppress HIV-specific CD4 T-cell responses in HIV-infected patients" Blood. Nov. 15, 2004. vol. 104. No. 10 pp. 3249-3256.
Wittig. Burghardt. et al., "Therapeutic Vaccination against Metastatic Carcinoma by Expression-Modulated and Immunomodified Autologous Tumor Cells: A First Clinical Phase 1111 Trial" Human Gene Therapy 12:267-278 (Feb. 10, 2001).
Wong et al., "Identification of an MHC class I-restricted autoantigen in type 1 diabetes by screening an organ-specific cdna library," Nature Medicine, vol. 5, No. 9, pp. 1026-1031, Sep. 17, 2002.
Wu, et al., "Tumor necrosis factor-x regulation of CD4+ CD25+ T cell levels in NOD mice," Proceedings of the National Academy of Sciences, vol. 99, No. 19, pp. 12287-12292, Sep. 17, 2002.

Xiang et al., "Vaccination with a Plasmid Vector Carrying the Rabies Virus Glycoprotein Gene Induces Protective Immunity Against Rabies Virus," Virology 199,132-140 (1994).
Yamada, Y, et al., Phase II trial of paclitaxel by three-hour infusion for advanced gastric cancer with short premedication for prophylaxis against paclitaxel-associated hypersensitivity reactions. Ann Oncol. Aug. 12, 2001(18):1133-7.
Yang et al., "Early Studies on DNA-Based Immunizations for Measles Virus," Vaccine. vol. 15. No. 8, pp. 888-892. 1997.
Yogelzang NJ, et al., Dihydro-5-azacytidine in malignant mesothelioma. a phase II trial demonstrating activity accompanied by cardiac toxicity. Cancer and Leukemia Group B. Cancer. Jun. 1, 1997;79(11 ):2237-42.
Yoon, et al., "Cellular and Molecular Pathogenic Mechanisms of Insulin-Dependent Diabetes Mellitus," Health Aging for Functional Longevity:Molecular and Cellular Interactions in Senescence, Annals of the New York Academy of Sciences, vol. 928, pp. 200-211, Apr. 2001.
Zeng IC, et al. Improved long-term survival for unresectable hepatocellular carcinoma (HCC) with a combination of surgery and intrahepatic arterial infllsion of 1311-anti-HCC mAb. Phase 1111 clinical trials. J Cancer Res Clin Oncol. 1998;124(5):275-80.
Zou et al. (1999) J. Acquir. Immune Defic. Syndr. 22:31-38.
Patent Cooperation Treaty, PCT International Search Report, dated Nov. 14, 2005, 4 pages.
International Search Report for International (PCT) Application No. PCT/AU2004/001456, mailed Dec. 8, 2004.
International Preliminary Report on Patentability for International (PCT) Application No. PCT/AU2004/001456, completed Sep. 27, 2005.
Written Opinion for International (PCT) Patent Application No. PCT/AU2004/001456, mailed Dec. 8, 2004.
Supplementary European Search Report for EP 03 70 1355, complete Dec. 5, 2005.
Supplementary Partial European Search Report, European Patent Office, dated Aug. 11, 2008, 8 pages.
Supplementary Partial European Search Report, dated Aug. 8, 2008, 8 pages.
European Examination Report, dated Jul. 9, 2008, 10 pages.
European Supplementary Search Report, dated Aug. 6, 2008, 6 pages.
Chinese Office Action for Patent Application No. 01817380—English Translation referencing Ming, Meng et al., Journal of Hebei Occupational Institute of Medical Science, 1997, No. 1, pp. 22-25.
Official Action for Australia Patent Application No. 2004283322, dated Jan. 13, 2010, 3 pages.
Request to Amend a Complete Specification, dated Jun. 22, 2010, in Australian Application No. 2004283322, 30 pages.
Official Action for Australia Patent Application No. 2004283322, dated Jul. 1, 2010, 3 pages.
Request to Amend a Complete Specification, dated Aug. 27, 2010, in Australian Application No. 2004283322, 27 pages.
Official Action (with English translation) for China Patent Application No. 2004800389993, dated Apr. 24, 2009, 9 pages.
Official Action for European Patent Application No. 04761461.5, dated Dec. 17, 2008, 7 pages.
Official Action for European Patent Application No. 04761461.5, dated Aug. 7, 2009, 8 pages.
Official Action for European Patent Application No. 04761461.5, dated Feb. 24, 2010, 15 pages.
Official Action for European Patent Application No. 04761461.5, dated Jul. 2, 2010, 29 pages.
Response, dated May 12, 2009, in European Application No. 04761461, 17 pages.
Response, dated Dec. 17, 2009, in European Application No. 04761461, 17 pages.
Written submissions, dated Apr. 19, 2010, in European Application No. 04761461, 129 pages.
Official Action (with English translation) for Japanese Patent Application No. 2006-535913, dated Oct. 25, 2010, 10 pages.
Official Action for Mexico Patent Application No. PA/a/2006/004522 dated May 18, 2009, 4 pages.

Official Action for Mexico Patent Application No. PA/a/2006/004522 dated Nov. 9, 2009, 2 pages.
Official Action for Mexico Patent Application No. PA/a/2006/004522 dated Mar. 23, 2010, 3 pages.
Response, dated Oct. 2, 2009, in Mexican Application No. PAa2006004522, 14 pages.
Response, dated Jan. 25, 2010, in Mexican Application No. PAa2006004522, 14 pages.
Response, dated Jul. 28, 2010, in Mexican Application No. PAa2006004522, 5 pages.
Official Action for New Zealand Patent Application No. 546873, dated Dec. 4, 2007, 2 pages.
Official Action for New Zealand Patent Application No. 546873, dated Sep. 30, 2009, 2 pages.
Official Action for New Zealand Patent Application No. 546873, dated Jan. 19, 2010, 2 pages.
Official Action for New Zealand Patent Application No. 546873, dated Jul. 5, 2010, 2 pages.
Response, dated Jun. 3, 2009, in New Zealand Application No. 546873, 43 pages.
Response, dated Jan. 5, 2010, in New Zealand Application No. 546873, 6 pages.
Response, dated Jun. 21, 2010, in New Zealand Application No. 546873, 42 pages.
Response, dated Jul. 28, 2010, in New Zealand Application No. 546873, 43 pages.
Official Action for Australia Patent Application No. 2005282218, dated Nov. 9, 2010, 3 pages.
Official Action for European Patent Application No. 05777835.9, dated Dec. 4, 2008, 1 page.
Response to Dec. 4, 2008 Official Action for European Patent Application No. 05777835.9, dated Sep. 22, 2009, 30 pages.
Official Action for European Patent Application No. 05777835.9, dated Dec. 17, 2009, 12 pages.
Response to Dec. 17, 2009 Official Action for European Patent Application No. 05777835.9, dated Oct. 8, 2010, 11 pages.
English Translation of Official Action for Japan Patent Application No. 2007-530544, mailed Aug. 9, 2011, 4 pages.
Summons to Oral Proceedings for European Patent Application No. 05777835.9, dated Jul. 6, 2011, 14 pages.
Response to Jul. 6, 2011 Summons to Oral Proceedings for European Patent Application No. 05777835.9, dated Oct. 3, 2011, 7 pages.
European Search Report and Search Opinion for European Patent Application No. 10180749, completed Jul. 11, 2011, 14 pages.
Official Action with English translation for Japan Patent Application No. 2006-535913, mailed Sep. 29, 2011, 4 pages.
Official Action for U.S. Appl. No. 10/576,981, mailed May 21, 2008.
Official Action for U.S. Appl. No. 10/576,981, mailed Dec. 9, 2008.
Official Action for U.S. Appl. No. 10/576,981, mailed Dec. 1, 2009.
Official Action for U.S. Appl. No. 10/576,981, mailed Jun. 3, 2010.
Notice of Appeal with English translation for Japan Patent Application No. 2006-535913, dated Dec. 9, 2011, 15 pages.
Official Action for Canada Patent Application No. 2,543,490, dated Dec. 15, 2011, 7 pages.
Response to Dec. 15, 2011 Official Action for Canada Patent Application No. 2,543,490, dated Jun. 15, 2012, 31 pages.
Official Action for Canada Patent Application No. 2,543,490, dated Aug. 15, 2012, 6 pages.
Allan, et al., CD4+ T-regulatory cells: toward therapy for human diseases, Immunological Reviews, 2008, vol. 223, Iss. 1 pp. 391-421.
Awwad, et al., "Cyclophosphamide-induced Immunologically Mediated Regression of a Cyclophosphamide-resistant Murine Tumor: A Consequence of Elimination Precursor L3T4+ Suppressor T-Cells," Cancer Research, 1989, vol. 49, No. 7, pp. 1649-1654.
Belkaid, et al., "Regulatory T Cells in the Control of Host-Microorganism Interactions," Annual Review of Immunology, 2009, vol. 27, 41 pages.
Bottazzo, et al., "In Situ Characterization of Autoimmune Phenomena and Expression of HLA Molecules in the Pancreas in Diabetic Insulitis," The New England Journal of Medicine, 1985, vol. 313, pp. 353-360.
Brusko, et al., "Human regulatory T cells: role in autoimmune disease and therapeutic opportunities," Immunological Reviews, 2008, vol. 223, Iss. 1, pp. 371-390.
Byrd, et al., "A Limited Memory Algorithm for Bound Constrained Optimization," SIAM Journal on Scientific Computing, 1995, vol. 16, No. 5, pp. 1190-1208.
Cao, et al., "Regulatory T Cell Expansion and Immune Activation during Untreated HIV Type 1 Infection are Associated with Disease Progression" AIDS Research and Human Retroviruses, 2009, vol. 25, No. 2, pp. 183-191.
Gajewski, et al., "Emerging strategies in regulatory T-cell immunotherapies," Clinical Advances in Hematology & Oncology, 2009, vol. 7, Iss. 1, 8 pages.
Kim, et al., "Dynamics and Potential Impact of the Immune Response to Chronic Myelogenous Leukemia," PLoS Computational Biology, 2008, vol. 4, Iss. 6, 17 pages.
Melichar, et al., "The Peripheral Blood Leukocyte Phenotype in Patients with Breast Cancer: Effect of Doxorubicin/Paclitaxel Combination Chemotherapy," Immunopharmacology and Immunotoxicology, 2001, vol. 23, No. 2, pp. 163-173.
Vila, et al., "Regulatory T cells and autoimmunity," Current Opinion in Hematology, 2009, vol. 16, Iss. 4, pp. 274-279.
European Search Report and Search Opinion for European Patent Application No. 10779928, dated Oct. 29, 2012, 4 pages.

* cited by examiner

METHOD OF THERAPY

CROSS-REFERENCE TO RELATED APPLICATIONS

This application is a Continuation of U.S. patent application Ser. No. 10/576,981, filed Mar. 2, 2007; which is a 371 National Phase filing of PCT/AU04/01456, filed Oct. 22, 2004; both of which are entitled "METHOD OF THERAPY" and hereby incorporated herein by reference in their entirety.

FIELD OF THE INVENTION

Numerous diseases have been linked to the production of regulator cells. The present invention relates to the observation that the immune system is cycling in these diseases. Based on these observations, the present invention provides methods for treating diseases such as cancer and a HIV infection. The present invention also relates to methods of determining when a therapy to treat a disease characterized by the production of regulator cells should be administered to a patient.

BACKGROUND OF THE INVENTION

In the past, attempts have been made to trigger the immune system to mount an efficient response against malignant cells. Despite significant and promising progress, such a response has yet to be fully attained and many immune based therapies have proved disappointing.

Numerous studies using in vitro cellular assays demonstrate that cytotoxic lymphocytes have the ability to kill tumour cells. Why this immune based destruction does not effectively control tumour growth in vivo is a conundrum. The cancer patient also has increased concentration of circulating immune complexes, indicating the immune system is active, particularly against certain tumour antigens. The level of these immune complexes can increase with disease progression (Horvath et al, 1982; Aziz et al, 1998).

Regulatory cells (also referred to in the art as suppressor cells) have been implicated in a subjects immune response to cancer (North and Awwad, 1990; WO 03/068257). As most cancer antigens are actually produced by the patient they are considered as "self" by the immune system. Upon the presence, and/or increased quantity, of tumour antigen the hosts immune system mounts a response characterized by the production of effector cells which target cells producing the tumour antigen. However, in many instances these effector cells are recognized by the immune system as targeting the hosts own cells, and hence a population of regulator cells are produced to down-regulate the effector cell population. Thus, the production of these regulator cells limits the ability of the immune system to effectively remove cancer cells.

More recently, regulator cells have been shown to be involved in a subjects immune response to a viral infection. WO 02/13828 describes the production of regulator cells during retroviral infection, and methods of treating such infections by down-regulating the regulator cell population whilst maintaining the effector cell population. Furthermore, Peterson et al (2002) observed that a population of CD4+ regulator cells were suppressing the ability of CD8+ effector cells to control Friend murine retrovirus infections in mice.

Measurements of certain acute-phase protein plasma concentrations can be of diagnostic or prognostic value under specific clinical conditions. The best known acute-phase protein is C-reactive protein (CRP). CRP is a plasma protein that rises in the blood with the inflammation from certain conditions. The level of CRP in blood plasma can rise as high as 1000-fold with inflammation. Conditions that commonly lead to marked changes in CRP include bacterial and viral infection, trauma, surgery, burns, inflammatory conditions, coronary and vascular disease and advanced cancer.

Most acute phase proteins are synthesized by hepatocytes, some are produced by other cell types, including monocytes, endothelial cells, fibroblasts and adipocytes. Acute phase proteins include serum amyloid A (SAA), CRP and serum amyloid P component (SAP).

The immediate responsiveness of CRP and SAA to stimuli, together with their wide concentration range and ease of automated measurement, have led to plasma CRP and SAA levels being used to monitor accurately the severity of inflammation and the efficacy of disease management during certain disease conditions.

WO 03/070270 describes the use of acute phase inflammatory markers in regimes for the effective treatment of HIV. These methods rely on at least partially "resetting" the immune system by a treatment such as HAART followed by the analysis of acute phase inflammatory proteins as markers for effector/regulator cell expansion. The emergence of acute phase inflammatory proteins appears to be linked to effector cell expansion, which occurs before regulator cell expansion, and thus the patient can be treated with a suitable agent which allows the effector cell population to be maintained whilst destroying, preventing the production of, or reducing the activity of, regulator cells. In essence, upon withdrawal of HAART treatment it was considered that the patient s immune system would treat the re-emerging HIV particles as a new infection, and hence a new population of effector cells would be produced.

Similar to WO 03/070270, WO 03/068257 relates to at least partially resetting the immune system, however, in this instance in the context of the treatment of cancer. Again, the treatment is focussed on the initial re-emergence of effector cells following a reduction in tumour load through techniques such as surgery or the administration of anti-proliferative drugs.

Neither WO 02/13828, WO 03/070270 or WO 03/068257 appreciate that the immune response is cycling in a cancer or HIV patient regardless of the administration of treatment for these diseases. The present invention is based on the realization of this cycling, and thus provides methods for the treatment of diseases linked to regulator cell production or activity.

SUMMARY OF THE INVENTION

The present inventor has surprisingly found that the immune system is cycling during disease states characterized by the presence of regulator cells. This cycling occurs on a regular basis of approximately 14 to 15 days in humans.

Whilst not wishing to be limited by theory, it appears that effector cell expansion against a target antigen is followed by the expansion of regulator cells directed against the effectors. Upon control of the effector cells by the regulator cells the numbers and/or activity of both types of cells decrease, which in turn is followed by the same cycle due to the continuous presence or incomplete removal of antigen which results in an oscillating persistent, but ineffective, immune response against the, for example, tumour or virus.

Knowledge of this cycle can be used to treat diseases where it is known that the emergence of regulator cells is detrimental to the patient. Examples of such diseases include cancer and persistent infections such as by the human immunodeficiency virus. More specifically, treatment of a patient can be timed such that effector cell numbers against a cellular or viral antigen are maximized whilst regulator cell numbers are reduced or abolished.

In fact, the present inventor has noted that the treatment of a wide variety of cancers with anti-cancer drugs results, on average, in a complete response rate in the range of 6.5 to 7%. This range of 6.5 to 7% is consistent with an about 14 to 15 day cycle of effector cell expansion followed by regulator cell expansion. More specifically, when not taking into consideration the cycling of effector and regulator cells, a medical practitioner has an approximate 1 in 14.5 chance (6.8%) of administering an anti-proliferative drug at a time where effector cells numbers are high but regulator cell numbers have only begun to expand and hence are vulnerable to treatments which target dividing cells. This leaves high numbers of effector cells which target the cancer cells, resulting in a complete response to the therapy.

Accordingly, in a first aspect the present invention provides a method for determining when an agent should be administered to a patient suffering from a disease characterized by the production of regulator cells, the method comprising monitoring the patient, or samples obtained therefrom, for at least one of: a) effector cell numbers and/or activity, b) regulator cell numbers and/or activity, c) a molecule associated with the disease, and/or d) an immune system marker.

In another aspect, the present invention provides a method of treating a disease characterized by the production of regulator cells, the method comprising;

i) monitoring a patient suffering from the disease for at least one of
  a) number and/or activity of regulator cells,
  b) number and/or activity of effector cells,
  c) a molecule associated with the disease, and/or
  d) an immune system marker, and
ii) exposing the patient to an agent to treat the disease, wherein the timing of administration of the agent is selected such that the activity of effector cells is not significantly reduced.

Preferably, the disease characterized by the production of regulator cells is selected from, but not limited to, cancer and an infection.

The infection can be caused by any type of infectious agent such as, but not limited to, a virus, bacteria, protozoa, nematode, prion, or fungus. Preferably, the infectious agent causes chronic persistent infection characterized by the patient immune system not being able to eliminate the infectious agent. Examples of infectious agents which cause chronic persistent infection are viruses such as HIV, the Hepatitis B virus and the Hepatitis C virus.

Whilst not wishing to be limited by theory, it appears that as antigen load, for example from increased tumour growth or viral replication, increases following regulator cell activity the patient s immune system responds in a manner similar to a first time exposure to the antigen. This immune response includes the production of acute phase inflammatory markers such as serum amyloid A and c-reactive protein.

An appropriate time to administer the agent is between when the levels of acute phase inflammatory marker have peaked and before the marker begins to rise in the next cycle. Accordingly, a particularly preferred immune system marker is an acute phase inflammatory marker. More preferably, the acute phase inflammatory marker is selected from, but not limited to, the group consisting of serum amyloid A, serum amyloid P and c-reactive protein.

Preferably, the immune system marker reflects the number and/or activity of regulator cells, and/or the number and/or activity of effector cells.

In one embodiment, the patient is monitored for an increase in the number and/or activity of regulator cells by the analysis of CD4+CD8− T cell levels. With regard to this embodiment, it is preferred that the agent is administered about when CD4+CD8− T cells are detected.

In another embodiment, the patient is monitored for an increase in the number and/or activity of effector cells by the analysis of CD8+CD4− T cell levels. With regard to this embodiment, it is preferred that the agent is administered approximately when CD8+CD4− T cell numbers have peaked.

In another embodiment, the molecule associated with the disease is an antigen produced by a cancer cell or an infectious agent. In this embodiment, the agent is administered approximately when levels of the molecule associated with the disease begin to decrease.

In a further embodiment, the disease is cancer and the patient is monitored for fluctuations in the levels of tumour antigen(s). With regard to this embodiment, it is preferred that the agent is administered approximately when levels of tumour antigen begin to decrease.

In yet a further embodiment, the disease is caused by an infectious agent and the patient is monitored for fluctuations in the levels of antigen(s) produced by the infectious agent. With regard to this embodiment, it is preferred that the agent is administered approximately when levels of antigen, or infectious organisms or viruses (viral load), begin to decrease.

In another embodiment, the immune system marker is body temperature. With respect to this embodiment, it is preferred that the agent is administered when body temperature has peaked and before body temperature begins to rise in the next cycle.

As outlined herein, the present inventor has noted that fluctuations in numerous factors indicate that the immune system is cycling in patients suffering from a disease characterized by the production of regulator cells. These factors include acute phase inflammatory markers, viral antigens, cancer antigens and body temperature. These factors are linked, directly or indirectly, to the general state of the immune system including, but not necessarily limited to, effector cell production and/or activity, regulator cell production and/or activity, and/or B cell production and/or activity.

It will be appreciated by the skilled person that diseases such are cancer and AIDS have a complex effect on the patient. Furthermore, natural variations between individuals linked to factors such as their genotype, nutrition, fitness, previous and current disease status, all influence how a given individual responds to a disease state. Thus, whilst in most cases the cycle will be about 14 to 15 days, in some individuals this may be slightly shorter or longer. In addition, like the menstrual cycle, the length of the cycle may vary slightly within an individual due to natural variation and/or environmental factors. Thus, individual variation may at least be encountered with regard to, for example, i) the length of the cycle, ii) the absolute numbers of effector or regulator cells during the cycle, or iii) the levels of acute phase inflammatory markers during the cycle. Such variation may be exaggerated in patients with advanced cancer or infection, where the patient s immune system has been challenged for a considerable length of time.

As result, it will most likely be desirable to monitor the patient for a sufficient length of time to ensure that the dynamics of the immune system cycling within a particular patient is understood. Preferably, the patient is monitored for a period of at least 7 days, more preferably at least 14 days, more preferably at least 21 days, more preferably at least 28 days, more preferably at least 35 days, more preferably at least 42 days, and even more preferably at least 49 days.

Another complicating factor is that at least the levels of some acute phase inflammatory markers have been found to cycle about every 7 days (about half the length of a "full" immune system cycle). Thus, it appears that relying on these types of markers will improve the chance of successful treatment from about 6.8% (based on random administration of the agent) to about 50% (based on choosing the correct administration time by randomly choosing which of the peaks is linked to the appropriate time to target regulator cells). Whilst this is an improvement on current techniques, it is preferred that such markers are monitored in conjunction with other factors (for example, a molecule associated with the disease, regulator cells and/or effector cells) to optimize the chance of selecting the appropriate time to administer the agent.

Thus, in another embodiment, the patient is monitored for an acute phase inflammatory marker, and a molecule associated with the disease. With regard to this embodiment, the agent is administered between when the levels of the acute phase inflammatory marker have peaked and before the marker begins to rise in the next cycle, and when levels of the molecule associated with the disease begin to decrease or would have been predicted to begin to decrease based upon previous analysis of the molecule.

In general, it is preferred that numerous factors are monitored at the same time. This is because, due to the factors describe above, it is unlikely that each factor will have a perfect cycle profile within a 14/15 day period, particularly over a number of cycles, to routinely provide a clear indication of the appropriate time to administer the agent. Whilst the analysis of numerous factors of a long period may be costly, and may be of at least some inconvenience to the patient, diseases such as cancer and AIDS are life threatening. Hence it is worthwhile understanding as much as possible regarding immune system cycling in a given patient before the patient is treated.

In addition, although the analysis of different factors cycling in some patients may result in complex profiles, given the guidance provided herein it is well within the skill of the medical practitioner to analyse the monitoring data to determine the optimal time to administer the agent. An Example of the careful analysis of multiple factors to determine the appropriate time to effectively treat a disease characterized by the production of regulator cells is provided herein.

A further complicating factor will be if the patient has recently acquired a disease or trauma unrelated to that being treated. For example, a patient being treated for a HIV infection may also contract the common flu virus. The presence of the flu virus will result in, for example, an increase in acute phase inflammatory markers independent of the cycling of these markers which is occurring due to the HIV infection. Other diseases which may cause complications in monitoring effector/regulator cell cycling for use in the methods of the present invention include, rheumatoid arthritis, ulcers and chronic gum disease. Accordingly, it is desirable to monitor the patient for any factors which may result in elevated levels of, for example, acute phase inflammatory markers to ensure that the factor being monitored truly reflects effector/regulator cell cycling resulting from the disease being treated.

Furthermore, it is preferred that the patient is monitored as frequently as possible to ensure immune system cycling within a given patient is suitably characterized. Naturally this will ensure that the agent is administered at the appropriate time and that any small variations in, for example, effector/regulator cell numbers or activity, or markers thereof, is not misinterpreted. Preferably, the patient is monitored at least every 3 days, more preferably at least every 2 days, and most preferably at least every day. Monitoring may occur more frequently, for instance every 12 hours, when the cycling is reaching a stage where it is likely that the timing would be appropriate to administer the agent.

Preferably, the agent inhibits the production of, limits the function of, and/or destroys, regulator cells. More preferably, the agent is selected from the group consisting of anti-cancer drugs such as anti-proliferative drugs, radiation, dsRNA and antibodies which inhibit the production and/or activity of regulator cells. Preferably, the anti-proliferative drug is selected from the group consisting of, but not limited to, taxol, vincristine, vinblastine and anhydro vinblastine.

With regard to cancer, in contrast to typical anti-cancer drug therapy which is administered to target tumour cells, the method of treatment described herein actually targets regulator cells. This leaves suitable numbers of effector cells to produce the desired therapeutic effect.

Examples of preferred antibodies include, but are not limited to, anti-CD4+, anti-CTLA-4 (cytotoxic lymphocyte-associated antigen-4), anti-GITR (glucocorticoid-induced tumour necrosis factor receptor), anti-CD28 and anti-CD25.

Preferably, the patient has not been exposed to a treatment for the disease for at least 14 days, more preferably at least 21 days, and even more preferably at least 28 days.

The present inventor has also determined that treatment for a disease characterized by the production of regulator cells can be enhanced (or the chances of successful treatment can be increased) when the vaccine is administered at the appropriate time. In these instances, the vaccine boosts the innate immune response against the disease. This will most likely be a result of increased numbers and/or activity of effector cells. Although theoretically regulator cells will still ultimately be produced, the boosting of the immune system allows the patient to suitably control the disease before the emergence of the regulator cells. This scenario would explain why previous studies have shown that anti-HIV and anti-tumour vaccines are only successful in a small number of patients. More specifically, there is only a small chance the vaccine will be administered at the same time the innate immune response to the disease is occurring. Other times of administration in the prior art occur when there are high numbers and/or activity of regulators cells, or at times which uncouple the natural cycling of the immune system.

Thus, in another aspect the present invention provides a method for determining when a vaccine should be administered to a patient suffering from a disease characterized by the production of regulator cells, the method comprising monitoring the patient, or samples obtained therefrom, for at least one of a) effector cell numbers and/or activity, b) regulator cell numbers and/or activity, c) a molecule associated with the disease, and/or d) an immune system marker.

In a further aspect, the present invention provides a method of treating a disease characterized by the production of regulator cells, the method comprising;

i) monitoring a patient suffering from the disease for at least one of:
  a) number and/or activity of regulator cells,
  b) number and/or activity of effector cells,
  c) a molecule associated with the disease, and/or
  d) an immune system marker, and ii) exposing the patient to an vaccine to treat the disease, wherein the timing of administration of the vaccine is selected such that the activity of effector cells is not significantly reduced.

In one embodiment, the vaccine is administered about when the levels of effector cells are increasing.

In another embodiment, the vaccine is administered about when the levels of a molecule associated with the disease begin to decrease.

In a further embodiment, the vaccine is administered about when the levels of an acute phase inflammatory marker begin to increase. As outlined above, at least some acute phase inflammatory markers have been found to be cycling over about a seven day period where only every second peak of acute phase inflammatory marker levels is associated with effector cell numbers. Thus, in this embodiment, the monitoring will most likely need to be combined with the analysis of other factors described herein.

The observation that the immune system is cycling during disease states characterized by the presence of regulator cells can also be used as an indicator of the presence of such a disease. These diagnosis procedures would be particularly useful for analysing a patient for the recurrence of the disease state (such as a tumour) following treatment, or for analysing a patient determined to be susceptible to the disease (such as in cases where the subject has previously been identified as possessing a cancer susceptibility gene) for the emergence of the disease.

Thus, in a further aspect the present invention provides a method of diagnosing a disease characterized by the production of regulator cells, the method comprising monitoring the patient, or samples obtained therefrom, for at least one of: a) effector cell numbers and/or activity, b) regulator cell numbers and/or activity, c) a molecule associated with the disease, and/or d) an immune system marker, wherein cycling of any one of a) to d) indicates the disease may be present.

Naturally, as outlined above, the patient will need to be analysed for other disease states, such as minor infections such as influenza etc, to ensure that any cycling observed (especially when analysing acute phase inflammatory markers) is directly linked to a disease characterized by the production of regulator cells.

Whilst ideally the monitoring should continue indefinitely, this will most likely not be practical in a majority of situations. Thus, the diagnosis procedure can be performed on an intermittent basis based on assessed risk of the disease state emerging or re-emerging. As the skilled addressee will appreciate from the discussions herein, the term "intermittent basis" means that the method will require a suitable number of samples be analysed over a period of time to determine if immune cycling is occurring (for example samples obtained at least every 3 days for a period of about 14 days), however, if the test is negative this procedure may not need to be repeated (for example) for another year.

In another aspect, the present invention provides for the use of an assay which detects an immune system marker for determining when an agent or vaccine should be administered to a patient suffering from a disease characterized by the production of regulator cells.

Preferably, the marker is an acute phase inflammatory marker. More preferably, the marker is a positive acute phase inflammatory marker. Even more preferably, the marker is selected from the group consisting of, but not limited to, serum amyloid A and c-reactive protein.

In another aspect, the present invention provides for the use of an assay which detects effector cell numbers and/or activity for determining when an agent or vaccine should be administered to a patient suffering from a disease characterized by the production of regulator cells.

Preferably, the assay detects the number of CD8+CD4− T cells.

In another aspect, the present invention provides for the use of an assay which detects regulator cell numbers and/or activity for determining when an agent or vaccine should be administered to a patient suffering from a disease characterized by the production of regulator cells.

Preferably, the assay detects the number of CD4+CD8− T cells.

In another aspect, the present invention provides for the use of an assay which detects a molecule associated with a disease characterized by the production of regulator cells for determining when an agent or vaccine should be administered to treat the disease.

Preferably, the assay detects an antigen produced by a cancer cell or an infectious agent.

Preferably, the patient has not been exposed to a treatment for the disease for at least 14 days, more preferably at least 21 days, and even more preferably at least 28 days.

In a further aspect, the present invention provides for the use of an agent for the manufacture of a medicament for administering to a patient suffering from a disease characterized by the production of regulator cells, wherein the agent will be administered at a time selected such that the activity of effector cells is not significantly reduced, and wherein the patient has not been exposed to a treatment for the disease for at least 14 days.

Preferably, the agent inhibits the production of, limits the function of, and/or destroys, regulator cells.

As would be readily appreciated by those skilled in the art, the methods of the present invention may be repeated to provide a more complete treatment.

Preferably, the patient is a mammal. More preferably, the mammal is a human.

In a further aspect, the present invention provides a kit for determining when an agent or vaccine should be administered to a patient suffering from a disease characterized by the production of regulator cells, the kit comprising at least one reagent for monitoring the patient, or samples obtained therefrom, for at least one of a) effector cell numbers and/or activity, b) regulator cell numbers and/or activity, c) a molecule associated with the disease, and/or d) an immune system marker.

Preferably, the kit comprises written instructions for performing a method of the invention including reference to the preferred number of samples to be analysed, and the timing between sample analysis.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. A) C-reactive protein and tumour marker CA125 levels over a 14 day period in a patient with ovarian cancer. B) Serum amyloid A levels in the same patient over the same period (C-reactive protein levels from A) duplicated).

Figure 2:
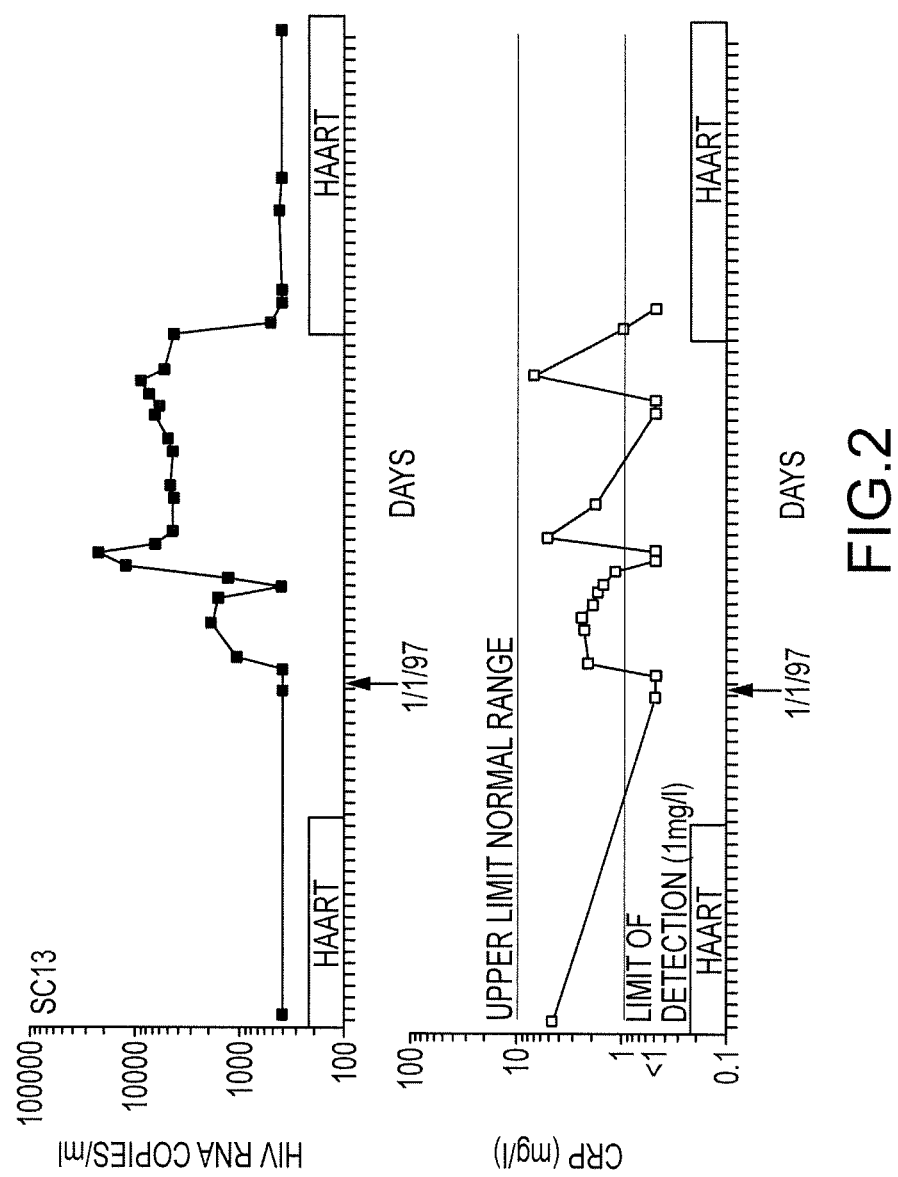

FIG. 2. C-reactive protein levels in response to taking a first human HIV patient off HAART treatment.

Figure 3:
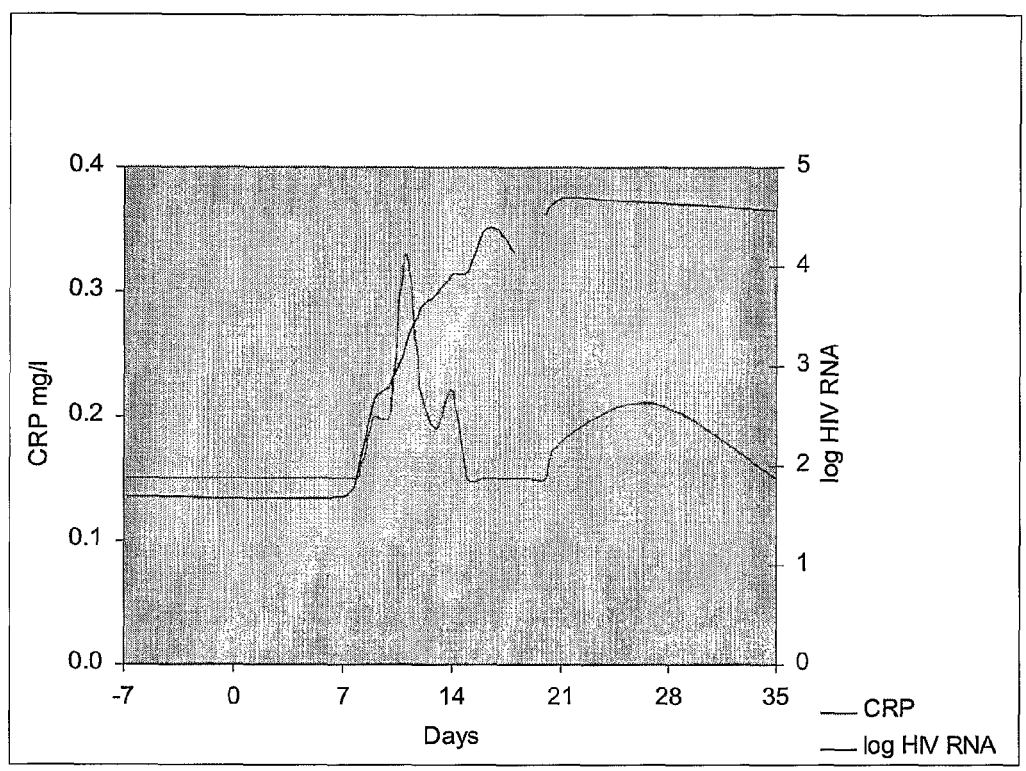

FIG. 3. Viral load and CRP fluctuations in a second HIV patient following the completion of HAART.

Figure 4:
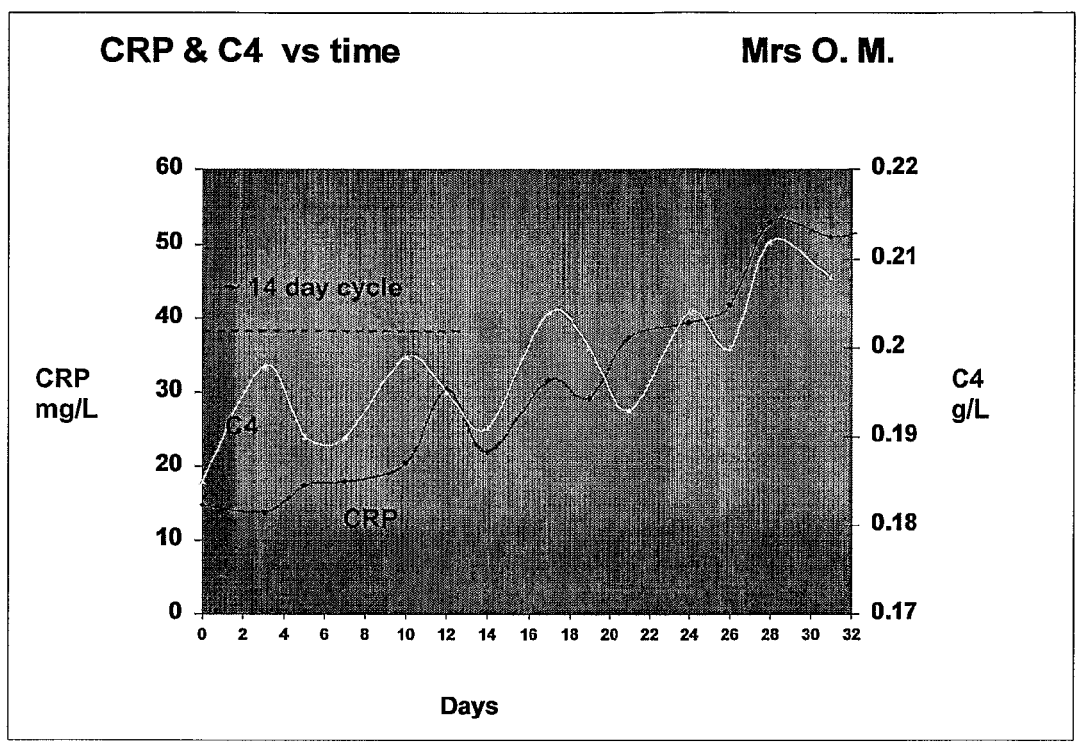

FIG. 4. CRP and C4 fluctuations in Mrs OM over 32 days shows a distinct periodicity with an approximate repeating 7/14 day oscillation. Measurements were taken every Monday, Wednesday and Friday. In this case the C4 oscillation is more regular. Note the rising trend in both parameters over the 32 day period.

Figure 5:
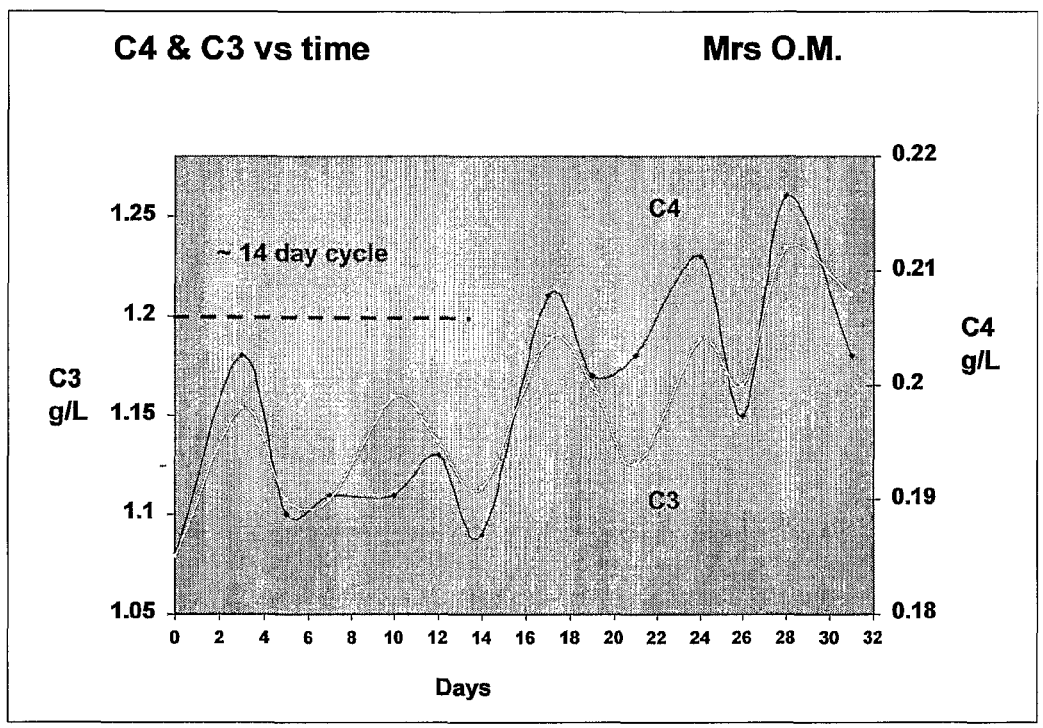

FIG. 5. Serum Complement factors C4 and C3 fluctuations in Mrs OM over 32 days show a near synchronous and regular periodicity of approximately 7/14 days. Note the rising trend in both parameters over the 32 day period.

Figure 6:
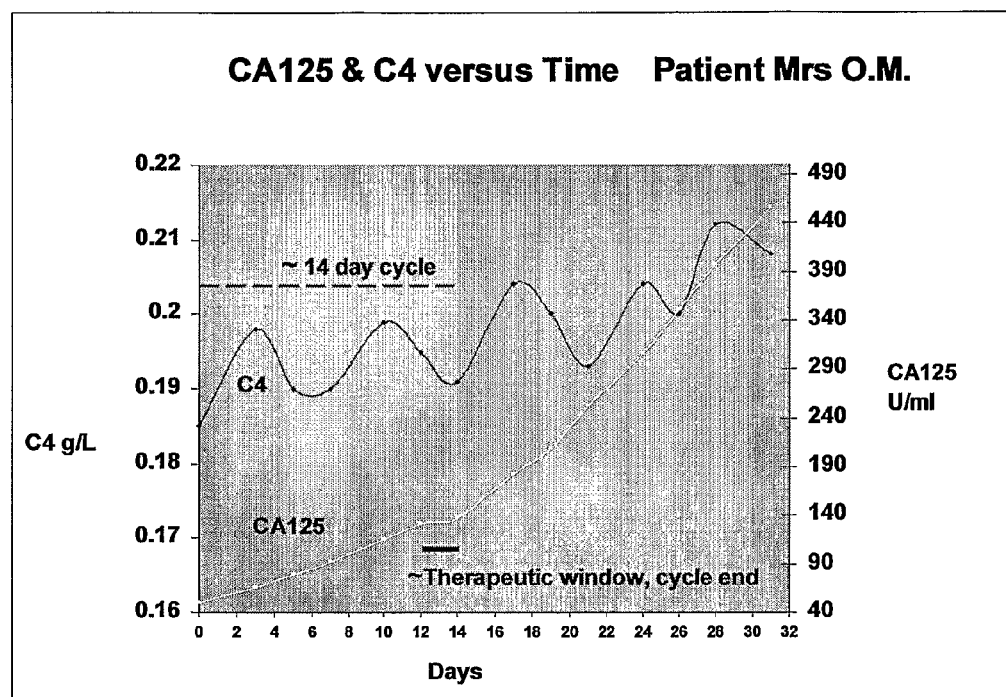

FIG. 6. Serum Complement Factor C4 fluctuations and rising CA125 levels with advancing disease in Mrs OM. Note the rising trend in both parameters over the 32 day period.

Figure 7:
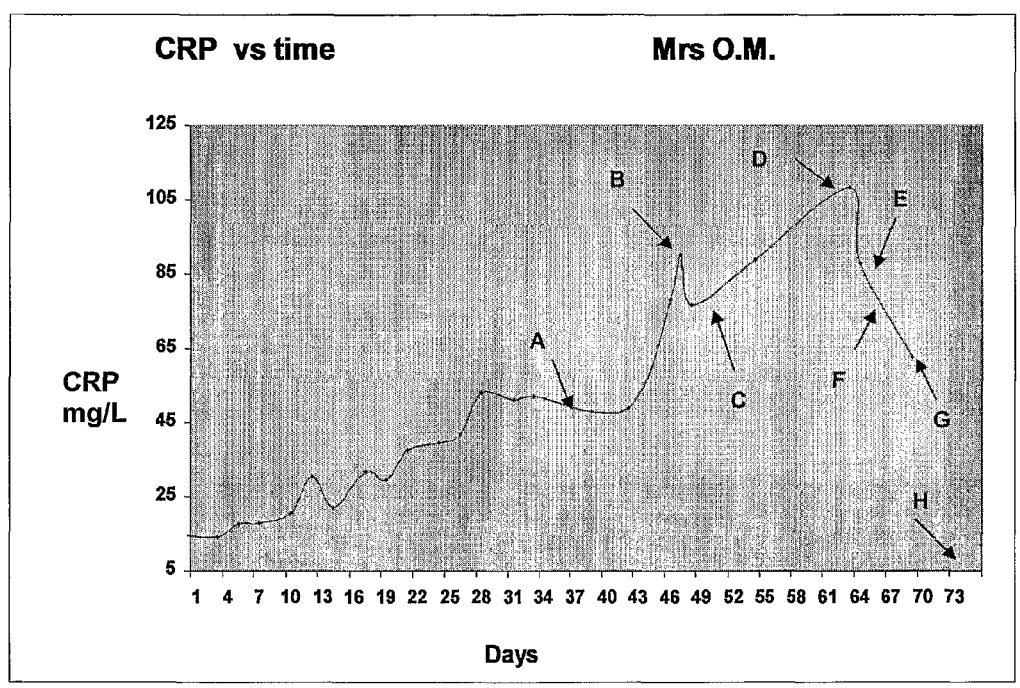

FIG. 7. C—Reactive Protein versus Time in Mrs OM, (days) Monitoring and Therapeutic events, 28 May 2004 (day 1)-9 Aug. 2004 (day 74). CRP monitoring began on the $28^{th}$ of May (day 1) and climbed steadily with advancing disease. The approx 14 day immune response oscillation was derived from the combined interpretation of serum CRP, C4 & CA125 collected data (see also FIG. 4). Key:
A=Radiotherapy begins, day 38, =5 Jul. 2004.
B=Predicted CRP peak, day 46, 47 & 48, =13, 14, 15, Jul. 2004.
C=Timing of first chemotherapy application, day 49, 16 Jul. 2004.
D=Predicted CRP peak, day 63 &64, =28, 29 Jul. 2004. Radiotherapy stops.
E=Timing of $2^{nd}$ chemotherapy application, day 65, =30 Jul. 2004.
F=Fever, day 66, =31 Jul. 2004, Haemorrhage from Tumour, day 67, =1 Aug. 2004.
G=CRP drops to 62.7 mg/l, day 69, =4 Aug. 2004.
H=Endoscopy reporting no evidence of tumour, day 74, =9 Aug. 2004.

Figure 8:
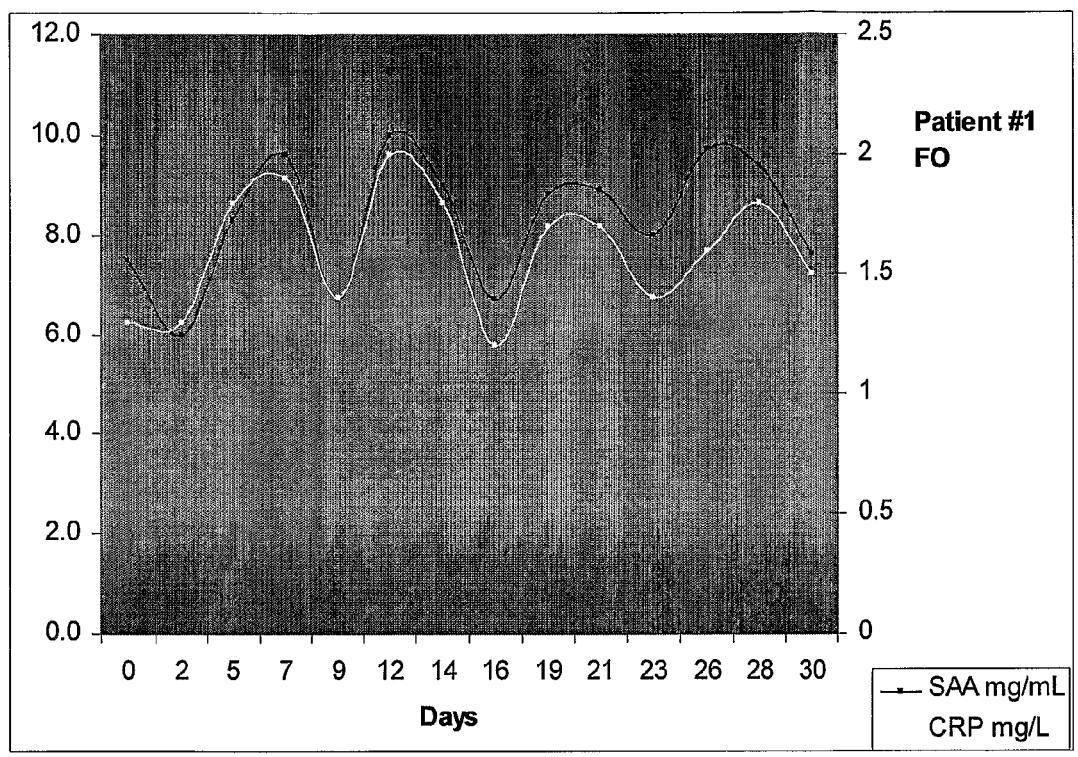

FIG. 8. C—Reactive Protein and Serum Amyloid A versus time in Mrs FO.

Figure 9:
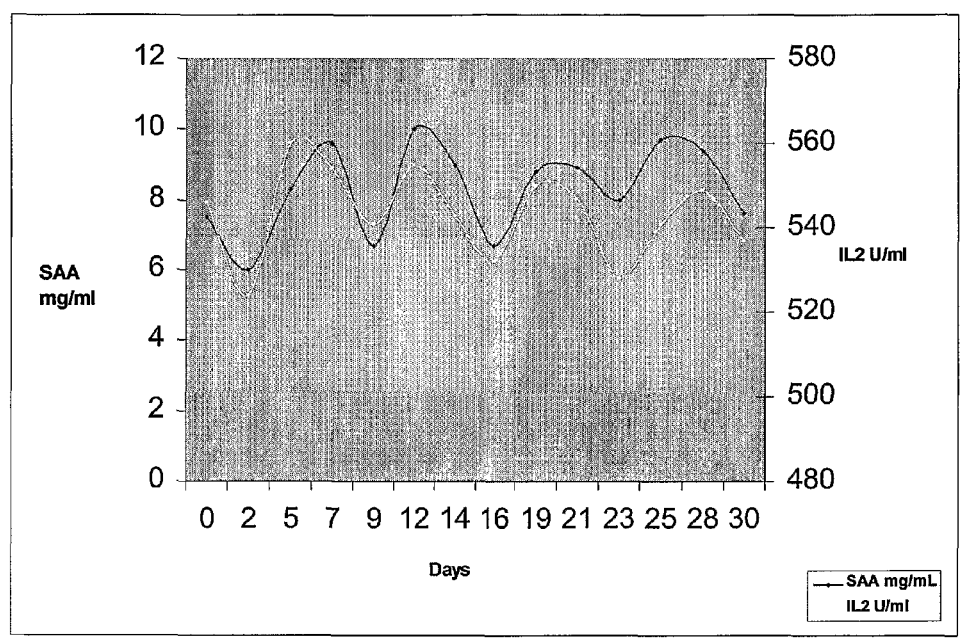

FIG. 9. C—Serum Amyloid A and IL-2 versus time in Mrs FO.

Figure 10:
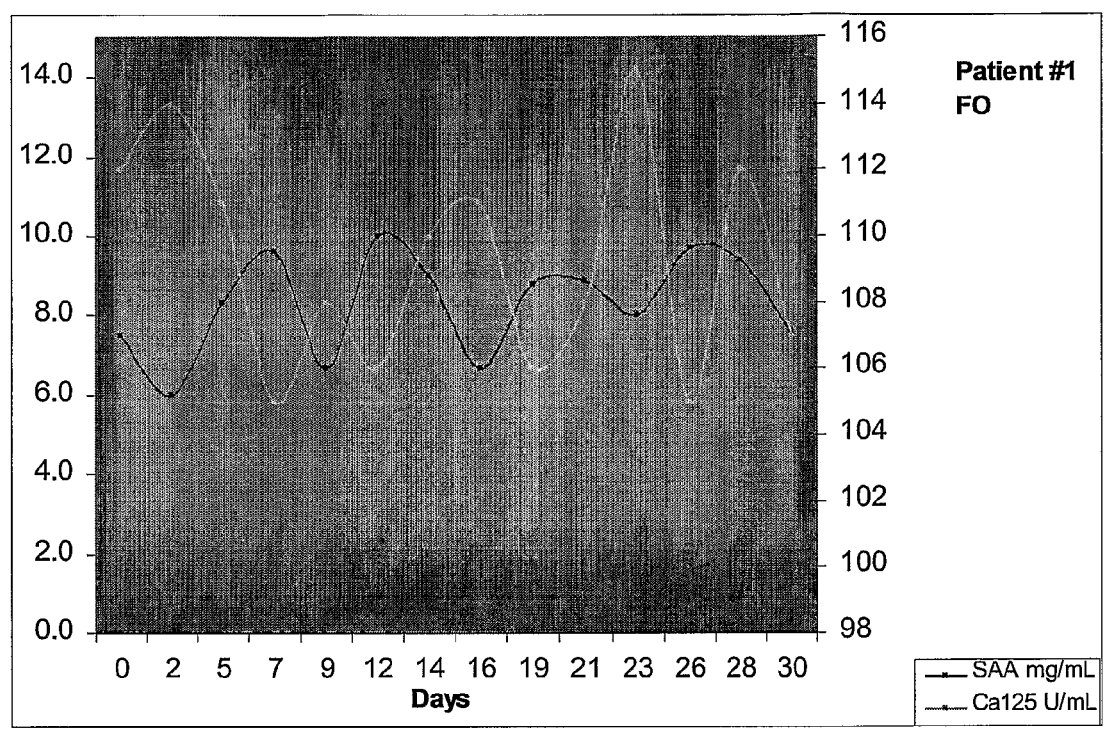

FIG. 10. Serum Amyloid A and cancer marker CA125 versus time in Mrs FO.

Figure 11:
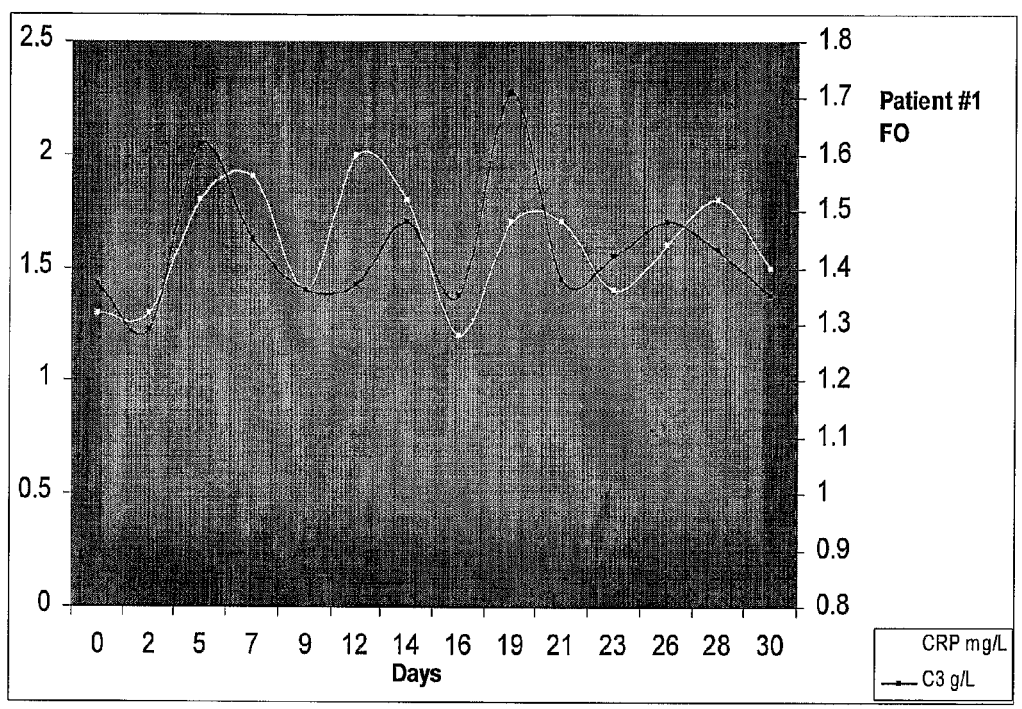

FIG. 11. C—Reactive Protein and C3 versus time in Mrs FO.

Figure 12:
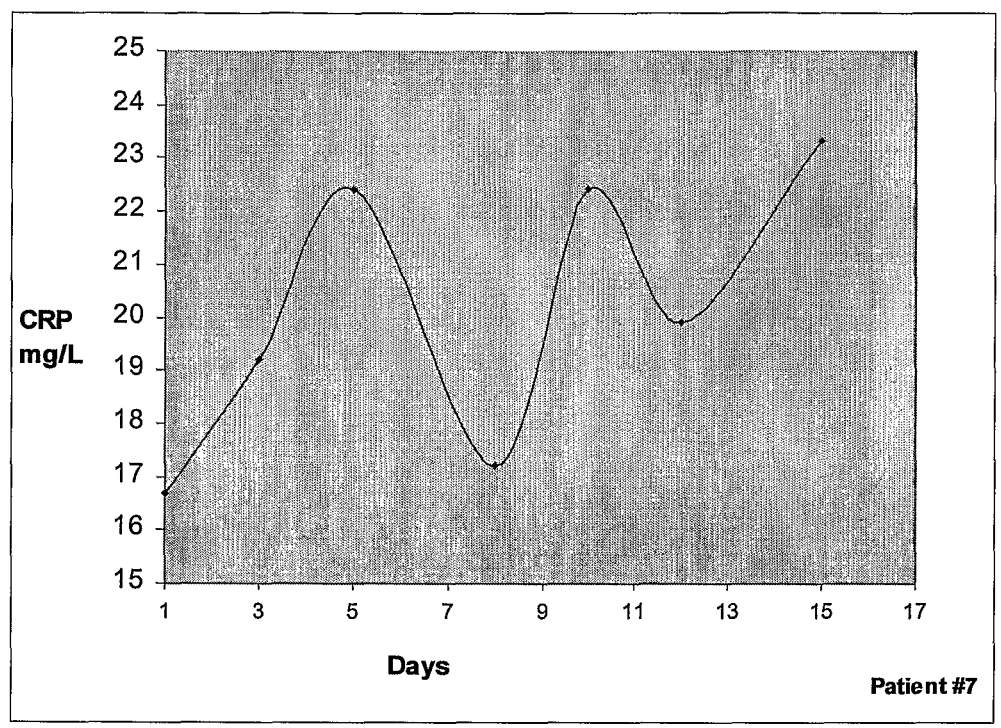

FIG. 12. C—Reactive Protein versus time in Mr GA.

DETAILED DESCRIPTION OF THE INVENTION

Definitions

As used herein the terms "treating", "treat" or "treatment" include administering a therapeutically effective amount of an agent sufficient to reduce or eliminate at least one symptom of the disease.

As used herein, the term "tumour load" generally refers to the number of cancerous cells in a subject at any given time. Measuring the level of tumor antigen in the subject can be considered as an indication of tumour load.

As used herein, the term "viral load" generally refers to the number of viral particles in a subject at any given time. Measuring the level of viral antigen in the subject can be considered as an indication of viral load.

"Regulator cells" include, but are not necessarily limited to, a subpopulation of CD4+ T cells. Such cells may also be referred to in the art as "suppressor cells". Regulator cells may either act directly on effector cells or may assert their affects upon effector cells through other mechanisms.

CD4+ cells express the marker known in the art as CD4. Typically, the term "CD4+ T cells" as used herein does not refer to cells which also express CD8. However, this term can include T cells which also express other antigenic markers such as CD25.

"Effector cells" include, but are not necessarily limited to, the T cell population known as CD8+ cells.

As used herein, the term "limits the function of, and/or destroys" when referring to the exposure of the "regulator cells" to the agent means that the number, and/or activity, of regulator cells is down-regulated by the agent. Most preferably, the number, and/or activity, of regulator cells is completely eradicated by the agent.

As used herein the term "disease characterized by the production of regulator cells" refers to any condition wherein the number or activity of regulator cells plays a role in prolonging the disease state. Examples of such disease include, but are not limited to, cancer and infections.

The term "immune system marker" generally refers to any molecule or factor which provides an indication of the state and/or activity of the immune system. These markers may be directly linked to the activity and/or production of regulator and/or effector cells, and/or may provide a more general indication of the overall response of the immune system to an antigen. Examples of a suitable immune system marker include acute phase inflammatory markers such as c-reactive protein and serum amyloid A. Another example of an immune system marker are indicators of cellular destruction such as, but not limited to, cholesterol and beta-2-microglobulin in serum. Cholesterol and beta-2-microglobulin are integral components of cellular membranes. In particular, beta-2-microglobulin is the accessory molecule to the Major Histocompatabilty Class I or MHC-I receptor. Consequently, with the cycling of the anti-disease immune response together with target cell destruction, the serum levels in cancer patients of these two molecules is often elevated. Thus, oscillations in indicators of cellular destruction, such as cholesterol and beta-2-microglobulin, may also prove useful in determining the beginning or end of the immune response cycle. Naturally, upon the present discovery of the immune system cycling in a disease characterized by the production of regulator cells, the skilled addressee could readily identify further markers useful in the methods of the invention.

As used herein, the term "a molecule associated with the disease" refers to any molecule which is linked to the disease state. In a preferred embodiment, the marker is a protein. Such protein markers are well known in the art. Examples of suitable tumour antigen markers are described herein. Suitable markers for, if not all, infectious diseases are also well known, for example the gag or env proteins of HIV.

As used herein the term "chronic persistent infection" refers to the presence of an infectious agent in the patient which is not readily controlled by the patient s immune system or available therapies. Examples include, but are not limited to, infections with *Mycobacterium tuberculosis* (which causes tuberculosis), HIV, the Hepatitis B virus or the Hepatitis C virus. To be classified as a "chronic persistent infection" it is preferred that the patient has at least had the infection for 3 months, more preferably at least 6 months.

For the purposes of this invention, the term "antibody", unless specified to the contrary, includes fragments of whole antibodies which retain their binding activity for a target analyte. Such fragments include Fv, F(ab') and F(ab')$_2$ fragments, as well as single chain antibodies (scFv). Furthermore, the antibodies and fragments thereof may be humanised antibodies, for example as described in EP-A-239400.

As is known in the art, a cancer is generally considered as uncontrolled cell growth. The methods of the present invention can be used to treat any cancer including, but not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma and peripheral neuroepithelioma.

The "sample" refers to a material suspected of containing regulator cells, effectors cells, immune system markers and/or a molecule associated with the disease. The sample can be used as obtained directly from the source or following at least one step of (partial) purification. The sample can be prepared in any convenient medium which does not interfere with the method of the invention. Typically, the sample is an aqueous solution or biological fluid as described in more detail below. The sample can be derived from any source, such as a physiological fluid, including blood, serum, plasma, saliva, sputum, ocular lens fluid, sweat, faeces, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Preferably, the sample is blood or a fraction thereof. Pretreatment may involve, for example, preparing plasma from blood, diluting viscous fluids, and the like. Methods of treatment can involve filtration, distillation, separation, concentration, inactivation of interfering components, and the addition of reagents. The selection and pretreatment of biological samples prior to testing is well known in the art and need not be described further.

Unless otherwise indicated, the recombinant DNA and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al, Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al (editors) Current Protocols in Immunology, John Wiley & Sons (including all updates until present), and are incorporated herein by reference.

Acute Phase Inflammatory Markers

Some acute phase inflammatory markers initially increase during an immune response (referred to hereinafter as positive acute phase inflammatory markers) whilst others initially decrease during an immune response (referred to hereinafter as negative acute phase inflammatory markers). Acute phase inflammatory markers are also referred to in the art as acute phase reactants or acute phase proteins. The skilled addressee will be aware of the many assays which can be used to monitor acute phase inflammatory markers.

Examples of positive acute phase inflammatory markers include, but are not limited to, c-reactive protein, serum amyloid A, serum amyloid P component, complement proteins such C2, C3, C4, C5, C9, B, C1 inhibitor and C4 binding protein, fibrinogen, von Willebrand factor, $\alpha 1$-antitrypsin, $\alpha 1$-antichymotrypsin, $\alpha 2$-antiplasmin, heparin cofactor II, plasminogen activator inhibitor I, haptoglobin, haemopexin, ceruloplasmin, manganese superoxide dismutase, $\alpha 1$-acid glycoprotein, haeme oxygenase, mannose-binding protein, leukocyte protein I, lipoporotein (a), lipopolysaccharide-binding protein, and interleukins such as IL-1, IL-2, IL-6, IL-10 and receptors thereof.

Example of negative acute phase inflammatory markers include, but are not limited to, albumin, pre-albumin, transferrin, apoAI, apoAII, $\alpha 2$ HS glycoprotein, inter-$\alpha$-trypsin inhibitor, histidine-rich glycoprotein.

Serum amyloid A (SAA) was discovered as a plasma component that shares antigenicity with amyloid AA, the chief fibrillar component in reactive AA amyloid deposits. SAA has been shown to be an acute phase reactant whose level in blood is elevated to 1000-fold or higher as part of the body's responses to various injuries including trauma, infection and inflammation.

SAA levels can be determined as known in the art, see for example Weinstein et al (1984), Liuzzo et al (1994), O'Hara et al (2000), Kimura et al (2001) and O'Hanlon et al (2002).

C-reactive protein (CRP) is an important positive acute phase response protein, and its concentration in serum may increase as much as 1.000-fold during the acute phase response. CRP is a pentamer consisting of five identical subunits, each having a molecular weight of about 23,500.

C-reactive protein levels can be determined using techniques known in the art, these include, but are not limited to, those disclosed in Senju et al (1983), Weinstein et al (1984), Price et al (1987), Liuzzo et al (1994), Eda et al (1998), Kimura et al (2001) and O'Hanlon et al (2002).

The complement proteins are a group of at least 20 immunologically distinct components. They normally circulate in the blood in an inactive form. They are able to interact sequentially with antigen—antibody complexes, with each other and with cell membranes in a complex but adaptable way to destroy viruses and bacteria and pathologically, even the hosts own cells. Abnormal serum levels of complement proteins may be due to either inherited or acquired diseases. At least circulating levels of C3 and C4 reflect a balance between complement consumption due to immune complex formation and increased synthesis due to acute phase response. Methods of measuring complement protein levels are well known in the art.

Levels of different interleukins can also be determined using procedures known in the art such as using the Proteo-Plex™ cytokine assay kit (EMD Biosciences Inc., CA, USA).

Agents

The agent can be any factor or treatment useful in treating a disease characterized by the production of regulator cells. Preferably, the agent selectively or non-selectively results in the destruction, the inhibition of the production, or reduction of activity, of regulator cells. For example, a CD4+ specific antibody could be used to specifically target CD4+ T cells. However, in some instances a non-selective agent could be used, such as an anti-proliferative drug or radiation, both of which destroy dividing cells. In particular, as with other cell types, regulator cells are particularly vulnerable to destruction by anti-mitotic (anti-proliferative) drugs or spindle poisons (e.g. Vinblastine or paclitaxel) when dividing and specifically in mitosis.

The term "anti-proliferative drug" is a term well understood in the art and refers to any compound that destroys dividing cells or inhibits them from undergoing further proliferation. Anti-proliferative drugs include, but are not limited to, mechlorethamine, cyclophosphamide, ifosfamide, melphalan, chlorambucil, hexamethyl-melamine, thiotepa, busulfan, carmustine, lomustine, semustine, streptozocin, dacarbazine, methotrexate, fluorouracil, floxuridine, cytarabine, mercaptopurine, thioguanine, pentostatin, vinblastine, anhydro vinblastine, vincristine, etoposide, teniposide, dactinomycin, daunorubicin, doxorubicin, bleomycin, plicamycin, mitomycin, L-asparaginase, cisplatin, mitoxantrone, hydroxyurea, procarbazine, mitotane, aminoglutethimide, prednisone, hydroxyprogesterone caproate, medroprogesterone acetate, megestrol acetate, diethylstilbestrol, ethinyl estradiol, tamoxifen, testosterone propionate, radioactive isotopes, ricin A chain, taxol, diphtheria toxin, colchicine and pseudomonas exotoxin A.

The agents are usually administered in the dosage forms that are readily available to the skilled clinician, and are generally administered in their normally prescribed amounts (as for example, the amounts described in the Physician's Desk Reference, 55th Edition, 2001, or the amounts described in the manufacture's literature for the use of the agent).

In one embodiment, the agent is administered as a single bolus injection. In another embodiment, the agent is administered by infusion. The period of infusion can be, for example, at least 3 hours, at least 12 hours or at least 24 hours.

Recent studies have suggested that CD4+CD25+ T cells play an important role in regulating immune cells directed against self antigens (Salomon et al, 2000; Suri-Payer and Cantor, 2001). Furthermore, targeting CD4+CD25+ T cells has been shown to enhance the ability of an animal to control tumour growth (Onizuka et al, 1999; Shimizu et al, 1999; Sutmuller et al, 2001). Accordingly, CD4+CD25+ T cells could be acting as regulator cells as used herein. The activity of CD4+CD25+ T cells can be downregulated by anti-GITR, anti-CD28 and/or anti-CTLA-4 (Read et al, 2000; Takahashi et al, 2000; Shimizu et al, 2002). Thus, these antibodies may be useful as agents for use in the methods of the present invention.

Another example of an agent which can be administered in a method of the invention is dsRNA. dsRNA is used in RNA interference (RNAi) which is a phenomenon where upon introduction into a cell, mRNA homologous to the dsRNA is specifically degraded so that synthesis of gene products is suppressed. Examples of such an agent causing RNAi include, but are not limited to, a sequence having at least about 70% homology to the nucleic acid sequence of a target gene or a sequence hybridizable under stringent conditions, RNA containing a double-stranded portion having a length of at least 10 nucleotides or variants thereof. Examples of target genes include, but are not limited to, a gene required for replication of a regulator cell, a gene required for survival of a cancer cell, or a gene required for growth and/or replication of an infectious agent.

dsRNA having a length of about 20 bases (e.g., representatively about 21 to 23 bases) or less than about 20 bases, which is called siRNA in the art, can be used. Expression of siRNA in cells can suppress expression of a gene targeted by the siRNA. In another embodiment, an agent capable of causing RNAi may have a short hairpin structure having a sticky portion at the 3' terminus (shRNA; short hairpin RNA). As used herein, the term "shRNA" refers to a molecule of about 20 or more base pairs in which a single-standed RNA partially contains a palindromic base sequence and forms a double-strand structure therein (i.e., a hairpin structure). shRNA can be artificially chemically synthesized. Alternatively, shRNA can be produced by linking sense and antisense strands of a DNA sequence in reverse directions and synthesizing RNA in vitro with T7 RNA polymerase using the DNA as a template. The length of the double-stranded portion is not particularly limited, but is preferably about 10 or more nucleotides, and more preferably about 20 or more nucleotides. The 3' protruding end may be preferably DNA, more preferably DNA of at least 2 nucleotides in length, and even more preferably DNA of 2-4 nucleotides in length.

An agent capable of causing RNAi useful for the invention may be artificially synthesized (chemically or biochemically) or naturally occurring. There is substantially no difference therebetween in terms of the effect of the present invention. A chemically synthesized agent is preferably purified by liquid chromatography or the like.

An agent capable of causing RNAi used in the present invention can also be produced in vitro. In this synthesis system, T7 RNA polymerase and T7 promoter can be used to synthesize antisense and sense RNAs from template DNA. These RNAs are annealed and thereafter are introduced into a cell.

dsRNA can be delivered to the patient using any means known in the art. Examples of methods of delivering dsRNA to a patient are described in, for example, US 20040180357, US 20040203024 and 20040192629.

Timing of Exposing the Subject to the Agent

For the investigator who randomly applies a single treatment of anti-proliferative chemotherapy to a cancer patient there is an approximate 1 in 14, to 1 in 15, chance of getting the timing right. A one in fourteen chance equates to a 7% probability of applying the therapy on the correct day, when the regulator cells are vulnerable to inactivation. If this is done, the tumour should regress mediated by immune destruction. More specifically, it is our hypothesis that once the regulators cells have been removed by therapeutic intervention, the immune response against the tumour or virus can proceed unimpeded, ultimately leading to control of the disease.

Whilst not wishing to be limited by theory, it is believed that the relative number of effector cells expands in response to an antigen before the regulator cells. Accordingly, as used herein, the term "the activity of the effector cells is not significantly reduced" means that the timing of the administration of the agent is such that the agent exerts a proportionally greater effect against the regulator cells than the effector cells. It is clearly preferred that the agent is administered at a time when the ratio of effect against the regulator cells to the effect against effector cells is greatest.

As outlined above, the present invention relies on the phenomenon that the immune system is cycling over an approximate 14 to 15 day period in a patient suffering from a disease characterized by the production of regulator cells. In most instances, the time point that the agent is to be administered will need to be empirically determined in subjects at different stages of disease as their immune response kinetics may vary. Other factors such as the general health of the subject and/or the genetic makeup of the subject will also impact upon when is the appropriate time to administer the agent.

As will be appreciated by the skilled addressee, conditions such as cancer and chronic persistent infectious are serious, often life threatening, diseases. Due to many factors, not the least of which is natural variations between individuals, it will be typically be required that a patient be monitored for a reasonable length of time to appreciate the nature of immune cycling in the individual, and for monitoring to analyse a number of factors (such as a combination of acute phase markers and disease antigens), to ultimately determine the most appropriate time to administer the agent to optimise the chances of an effective treatment.

Techniques known in the art can be used to monitor the growing population of effector and/or regulator cells during the "cycle".

Serial blood samples can be collected and quantitatively screened for all CD4+ subsets by FACS analysis. This FACS monitoring will need to be maintained until the regulator cells begin clonally expanding in response to the disease state, whether produced by the tumour or administered to the subject. Other possible assays for monitoring the growing population of regulator cells include lymphocyte proliferation/activation assays and various cytokine level assays (for example an assay for IL-4, IL-6 or IL-10).

Also, serial blood samples can be collected and quantitatively screened for all effector cell activity such as but not limited to CD8+, CRP, SAA and various cytokines. Such effector cell markers will precede the regulator cell markers.

When the disease is cancer another avenue of determining the time point for administering the agent is to monitor the tumour load. It is envisaged that the tumour load decreases due to the activity of the effector cells, however, the subsequent increase in regulator cells would down-regulate the effector cells resulting in a slowing of the tumour load decrease. Accordingly, the agent could be administered approximately prior to the slowing of the decrease in tumour load. Techniques known in the art, for example RT-PCR or antibody detection, of markers expressed by the tumour, could be used to measure tumour load in these circumstances. Examples of suitable tumour antigen marker assays include, but are not limited to, for AFP (marker for hepatocellular carcinoma and germ-cell tumours), CA 15-3 (marker for numerous cancers including breast cancer), CA 19-9 (marker for numerous cancers including pancreatic cancer and biliary tract tumours), CA 125 (marker for various cancers including ovarian cancer), calcitonin (marker for various tumours including thyroid medullary carcinoma), catecholamines and metabolites (phaeochromoctoma), CEA (marker for various cancers including colorectal cancers and other gastrointestinal cancers), hCG/beta hCG (marker for various cancers including germ-cell tumours and choriocarcinomas), 5HIAA in urine (carcinoid syndrome), PSA (prostate cancer), sertonin (carcinoid syndrome) and thyroglobulin (thyroid carcinoma).

Monitoring may need to be very frequent, for example as often as every few hours, to ensure the correct time point is selected for administration of the agent. Preferably, the monitoring is conducted at least every 48 hours. More preferably, the monitoring is conducted at least every 24 hours.

Optimally, the monitoring is continued to determine the affect of the agent. Insufficient down-regulation, re-emergence of the regulator cells or increases in, for example, tumour load will mean that the method of the present invention should be repeated. Such repeated cycles of treatment may generate immunological memory. It is therefore possible that the present invention, used in repetitive mode, may provide some prophylactic protective effect.

Vaccines

As outlined above, the inventor has also noted after a survey of the literature that the treatment of a variety of cancers with therapeutic vaccines, on average yielded a complete response rate of approximately 10% (see, for example, Trefzer et al, 2004; Lotem et al., 2004; Smithers et al., 2003; Belli et al., 2002; Berd et al., 2001; Wittig et al., 2001). This implies a window of opportunity of therapeutic application of 1.5 days every 14 days (10%). This is similar and well within the realms of probability of the complete response rates of approximately 7% (1 day in 14) seen in cancer chemotherapy reported herein. Thus a similar mechanism is operating in the vaccine situation whereby the innoculation of a cancer vaccine into the patient at the correct time is sufficient to disturb the regulatory mechanisms/cells allowing the effectors to kill the tumour resulting in a complete response.

Naturally, vaccines used in the present invention will result in an immune against a disease characterized by the production of regulator cells. Such vaccine will comprise at least one antigen, or a polynucleotide encoding said antigen. The vaccine can be provided as any form known in the art such as, but not limited to, a DNA vaccine, ingestion of a transgenic organism expressing the antigen, or composition comprising the antigen.

As used herein, an "antigen" is any polypeptide sequence that contains an epitope which is capable of producing an immune response against the disease.

Antigens which are capable of raising an immune response against a cancer cell are well known in the art. Certain tumour antigens can be recognized and targeted by the immune system. This property may be due to overexpression by the tumour tissue. Some of these antigens can be detected in normal tissue. The tumour antigens targeted by T cells are generally proteins that are processed intracellularly and presented as short peptide fragments bound in the groove of the tumour MHC class I molecule to be recognized by $CD8^+$ cytotoxic T lymphocytes. The mere presence of a tumour antigen is not always sufficient to trigger an immune response. Co-stimulatory molecules such as B7.1 are sometimes required. Once antigen-specific T cells are stimulated, they are capable of recognizing and destroying the tumour. The conditions needed for the activation of antigen-specific T cells are stringent, but are open to genetic manipulation of target tumour cells and T cells.

Antigens which can be used to treat infections, such as HIV, are also well known in the art.

The antigen can be provided in any manner known in the art which leads to an immune response. An antigen can be, for example, native, recombinant or synthetic. Native antigens can be prepared, for example, by providing cell lysates of a tumour cell.

Vaccines may be prepared from one or more antigens. The preparation of vaccines which contain an antigen is known to one skilled in the art. Typically, such vaccines are prepared as injectables, or orals, either as liquid solutions or suspensions; solid forms suitable for solution in, or suspension in, liquid prior to injection or oral consumption may also be prepared. The preparation may also be emulsified, or the protein encapsulated in liposomes. The antigen is often mixed with carriers/excipients which are pharmaceutically acceptable and compatible with the active ingredient. Suitable carriers/excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine.

Typically, vaccines comprise an adjuvant. As used herein, the term "adjuvant" means a substance that non-specifically enhances the immune response to an antigen. Examples of adjuvants which may be effective include but are not limited to: N-acetyl-muramyl-L-threonyl-D-isoglutamine (thr- MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1-2-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. Further examples of adjuvants include aluminum hydroxide, aluminum phosphate, aluminum potassium sulfate (alum), bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAF-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

The proportion of antigen and adjuvant can be varied over a broad range so long as both are present in effective amounts. For example, aluminium hydroxide can be present in an amount of about 0.5% of the vaccine mixture ($Al_2O_3$ basis). Conveniently, the vaccines are formulated to contain a final concentration of antigenic polypeptide in the range of from 0.2 to 200 µg/ml, preferably 5 to 50 µg/ml, most preferably 15 µg/ml.

After formulation, the vaccine may be incorporated into a sterile container which is then sealed and stored at a low temperature, for example 4° C., or it may be freeze-dried. Lyophilisation permits long-term storage in a stabilised form.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

DNA vaccination involves the direct in vivo introduction of DNA encoding an antigen into tissues of a subject for expression of the antigen by the cells of the subject's tissue. Such vaccines are termed herein "DNA vaccines" or "nucleic acid-based vaccines". DNA vaccines are described in U.S. Pat. Nos. 5,939,400, 6,110,898, WO 95/20660 and WO 93/19183, the disclosures of which are hereby incorporated by reference in their entireties.

To date, most DNA vaccines in mammalian systems have relied upon viral promoters derived from cytomegalovirus (CMV). These have had good efficiency in both muscle and skin inoculation in a number of mammalian species. A factor known to affect the immune response elicited by DNA immunization is the method of DNA delivery, for example, parenteral routes can yield low rates of gene transfer and produce considerable variability of gene expression. High-velocity inoculation of plasmids, using a gene-gun, enhanced the immune responses of mice, presumably because of a greater efficiency of DNA transfection and more effective antigen presentation by dendritic cells. Vectors containing the nucleic acid-based vaccine of the invention may also be introduced into the desired host by other methods known in the art, e.g., transfection, electroporation, microinjection, transduction, cell fusion, DEAE dextran, calcium phosphate precipitation, lipofection (lysosome fusion), or a DNA vector transporter.

Transgenic plants producing a antigenic polypeptide can be constructed using procedures well known in the art. A number of plant-derived edible vaccines are currently being developed for both animal and human pathogens. Immune responses have also resulted from oral immunization with transgenic plants producing virus-like particles (VLPs), or chimeric plant viruses displaying antigenic epitopes. It has been suggested that the particulate form of these VLPs or chimeric viruses may result in greater stability of the antigen in the stomach, effectively increasing the amount of antigen available for uptake in the gut.

EXAMPLES

Example 1

Provided below are examples of typical assays used to monitor some acute phase inflammatory markers, as well as the ovarian cancer marker CA125.

C-Reactive Protein

C-Reactive Protein was measured using a DADE Behring Dimension RxL Chemistry Analyser, with reagents and calibrators supplied by Dade Behring Diagnostics (Sydney, Australia) (reagent-Cat No. DF-34; calibrators Cat. No. DC-34).

The CRP method is based on a particle enhanced turbidimetric immunoassay technique. Latex particles coated with antibody to C-Reactive Protein aggregate in the presence of C-Reactive Protein in the sample. The increase in turbidity which accompanies aggregation is proportional to the C-Reactive Protein concentration.

| INTRA-ASSAY PRECISION | | | INTER-ASSAY PRECISION | | |
|---|---|---|---|---|---|
| MEAN mg/L | CV | N | MEAN mg/L | CV | N |
| 3.4 | 4.3% | 20 | 4.6 | 5.6% | 64 |
| 57.5 | 2.3% | 20 | 37.0 | 3.0% | 64 |
| 225.8 | 2.0% | 20 | | | |

REFERENCE RANGE: 0-5 mg/L
ANALYTICAL RANGE: 0.5-500 mg/L

Cancer Antigen 125 (CA125)

AxSym CA 125 was based on Microparticle Enzyme Immunoassay (MEIA) technology carried out on an Abbott Diagnostics AxSym with reagents and calibrators supplied by Abbott Diagnostics (AxSym Reagent pack-Cat No. 3B41-22; calibrators-Cat No. 9C22-01).

Sample, Anti CA 125 coated microparticles and specimen diluent are pipetted in one well of the reaction vessel. The CA 125 binds to the Anti-CA 125 coated microparticles forming an Ab-Ag complex. An aliquot of the reaction mixture containing the Ab-Ag complex bound to the microparticles bind irreversibly to the glass fiber matrix. The matrix cell is washed with the wash buffer to remove the unbound materials. The anti-CA 125 subunit specific ALP conjugate is dispersed onto the matrix cell and binds with the Ab-Ag complex. The matrix cell is washed to remove unbound material. The substrate, 4-methyl umbelliferyl phosphate, is added to the matrix cell and the fluorescent product is measured by the MEIA optical assembly.

Dilutions are made with Abbott CA 125 specimen diluent (No. 3B41-50).

The coefficient of Variation as assessed from routine quality control sera at two levels (Abbott Tumour Marker Control (9C22-10 levels 1, 2 & 3) is as follows:

|  | MEAN | SD | CV % | N |
|---|---|---|---|---|
| LEVEL 1 U/mL | 27 | 2.5 | 9.4 | 64 |
| LEVEL 2 U/mL | 78 | 5.5 | 7.1 | 64 |
| LEVEL 3 U/mL | 211 | 21.4 | 10.2 | 54 |

REFERENCE RANGES: 0-35 U/mL
ANALYTICAL RANGE: 2-600 U/mL

Interleukin 2 Receptor (IL2R)

The receptor of the cytokine interleukin 2 (IL2R) was measured by a commercial automated chemiluminescent Enzyme Immuno Assay (EIA) using an Immulite Analyser from Diagnostic Products Corporation (Los Angeles, Calif., USA).

This is a competitive immunoassay using Alkaline Phosphatase labelled IL2R as tracer and adamantyl dioxetane as luminescent substrate for ALP enzyme.

All reagents and calibrators are supplied in kit form by DPC-Cat No. LKIPZ.

Analytical performance:

|  | MEAN | SD | CV % |
|---|---|---|---|
| LEVEL 1 | 213 U/mL | 13 | 6.1 |
| LEVEL 2 | 752 U/mL | 49 | 6.5 |
| LEVEL 3 | 2463 U/mL | 189 | 7.7 |

ANALYTICAL RANGE: 5-7,500 U/mL
REFERENCE RANGE: 223-710 U/mL*
*Study performed on 87 apparently healthy adults.

Interleukin 6

The cytokine interleukin 6 was measured by a commercial automated chemiluminescent Enzyme Immuno Assay (EIA) using an Immulite Analyser from Diagnostic Products Corporation (Los Angeles, Calif., USA).

This is a competitive immunoassay using Alkaline Phosphatase labelled IL-6 as tracer and adamantyl dioxetane as luminescent substrate for ALP enzyme.

All reagents and calibrators are supplied in kit form by DPC-Cat No. LK6PZ.

Analytical performance:

|  | MEAN | SD | CV % |
|---|---|---|---|
| LEVEL 1 | 88 pg/mL | 4.5 | 5.1 |
| LEVEL 2 | 230 pg/mL | 12.2 | 5.3 |
| LEVEL 3 | 638 pg/mL | 46.6 | 7.3 |

ANALYTICAL RANGE: 2-1000 pg/mL
REFERENCE RANGE: <4.1 pg/mL*
*Study performed on 60 apparently healthy laboratory volunteers.

Interleukin 10

The cytokine interleukin 10 was measured by a commercial automated chemiluminescent Enzyme Immuno Assay (EIA) using an Immulite Analyser from Diagnostic Products Corporation, Los Angeles, Calif. USA.

This is a competitive immunoassay using Alkaline Phosphatase labelled IL-10 as tracer and adamantyl dioxetane as luminescent substrate for ALP enzyme.

All reagents and calibrators are supplied in kit form by DPC-Cat No. LKXPZ.

Analytical performance:

|  | MEAN | SD | CV % |
|---|---|---|---|
| LEVEL 1 | 18.2 pg/mL | 1.8 | 9.9 |
| LEVEL 2 | 46.0 pg/mL | 2.2 | 4.8 |
| LEVEL 3 | 177 pg/mL | 8.0 | 4.5 |

ANALYTICAL RANGE: 5-1000 pg/mL
REFERENCE RANGE: <9.1 pg/mL*
*Study performed on 55 apparently healthy adults.

Serum Amyloid A

Polystyrene particles coated with antibodies to human SAA are agglutinated when mixed with samples containing SAA. The intensity of the scattered light in the nephelometer depends on the concentration of the analyte in the sample and consequently its concentration can be determined by comparison with dilutions of a standard of known concentration.

| IMPRECISION: | CV 4.7% @ 192 mg/L | N = 404 |
|---|---|---|
|  | CV 2.8% @ 7.0 mg/L | N = 40 |

REFERENCE RANGE: In a population with normal serum CRP levels ($95^{th}$ percentile=5.0 mg/L N=483) the $95^{th}$ percentile for N Latex SAA was found to be at 6.4 mg/L
ANALYTICAL RANGE: 3.0-200 mg/L Complement C3

The automated method used to measure complement C3 concentration in serum samples by nephelometric analysis using a Dade Behring ProSpect analyzer with reagents and calibrators supplied by Dade Behring Diagnostics (Sydney, Australia).

Soluble antigen solution (sample) and specific antibodies (antiserum Cat No. OSAP15) are mixed in the reaction cuvettes. Insoluble antigen-antibody complexes form immediately, producing turbidity in the mixture and increasing the amount of light scattered by the solution. Following an incubation period the absorbance of the solution is measured at the analytical wavelength.

| IMPRECISION: | CV 5.5% @ 1.05 g/L | N = 61 |
|---|---|---|
|  | CV 3.2% @ 2.70 g/L | N = 61 |

REFERENCE RANGE: 0.81-1.85 g/L
ANALYTICAL RANGE: 0.10-3.50 g/L

Complement C4

The automated method used to measure complement C4 concentration in serum samples by nephelometric analysis using a Dade Behring ProSpect analyzer with reagents and calibrators supplied by Dade Behring Diagnostics (Sydney, Australia).

Soluble antigen solution (sample) and specific antibodies (antiserum Cat No. OSAO15) are mixed in the reaction cuvettes. Insoluble antigen-antibody complexes form immediately, producing turbidity in the mixture and increasing the amount of light scattered by the solution. Following an incubation period the absorbance of the solution is measured at the analytical wavelength.

| IMPRECISION: | CV 4.7% @ 0.20 g/L | N = 61 |
| --- | --- | --- |
| | CV 3.8% @ 0.53 g/L | N = 61 |

REFERENCE RANGE: 0.10-0.40 g/L
ANALYTICAL RANGE: 0.03-1.50 g/L

Example 2

An elderly female ovarian cancer patient was monitored for about 12 days for fluctuations in the levels of c-reactive protein, serum amyloid A and the tumour marker CA125. Monitoring was performed using standard laboratory tests on blood samples collected every other day. The patient had not recently been exposed to any anti-cancer therapy. Furthermore, there was no evidence that the patient was suffering from any diseases other than cancer. The CA125 (an ovarian cancer marker) was monitored as an indicator of disease burden.

Figure 1B:
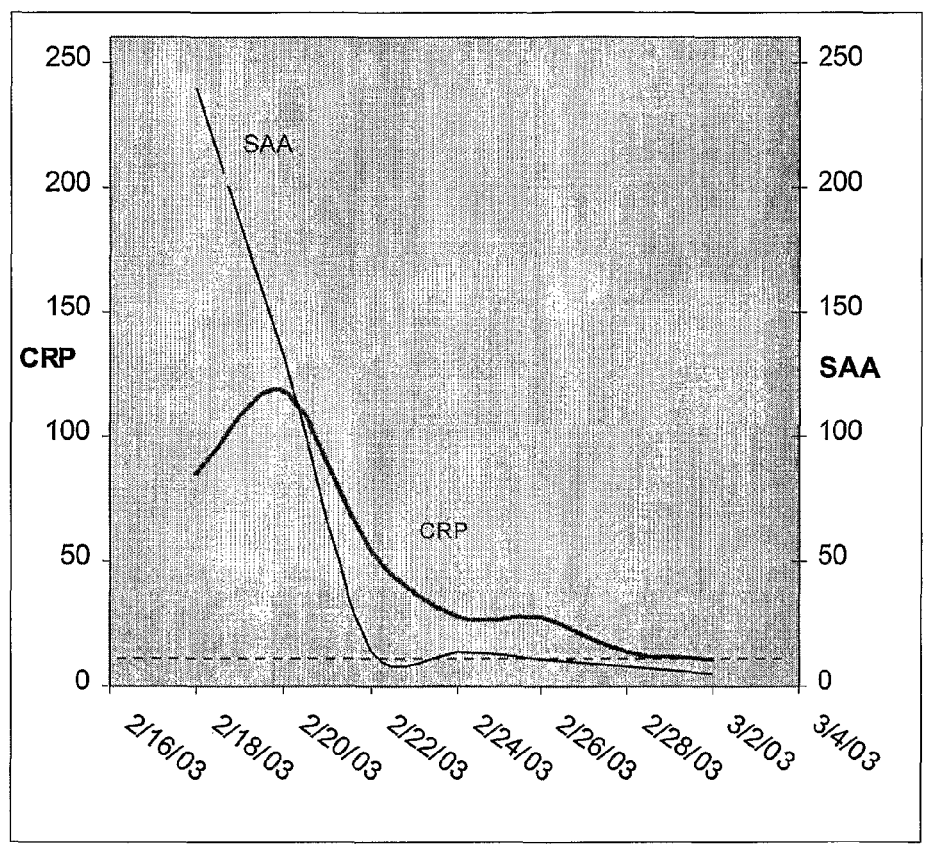

As shown in FIG. 1A, c-reactive protein (CRP) levels peaked at the beginning of the monitoring period. Furthermore, as shown in FIG. 1B serum amyloid A levels were elevated at the same time of the CRP peak.

These results indicate that;

i) the levels of acute phase inflammatory proteins are fluctuating in a cancer patient in the absence of any other known factors which might cause these fluctuations such as viral infection or chemotherapy, ii) elevated levels of acute phase inflammatory proteins was associated with lower levels of tumour antigens suggesting the presence of effector cells, and iii) increased levels of tumour antigen is associated with lower levels of acute phase inflammatory proteins suggesting that regulator cells have counteracted the beneficial activity of the effector cells such that these cells are no longer active against the tumour cells.

Example 3

A human subject suffering from a HIV infection was subjected to highly active antiretroviral therapy (HAART) for at least 6 months and then taken off the treatment. C-reactive protein levels were determined using standard techniques on samples obtained during and after the completion of HAART.

As can be seen in FIG. 2, the results show that upon conclusion of HAART c-reactive protein levels began to cycle, peaking approximately every 14 days.

Example 4

Serum CRP was used to monitor the immune response in HIV patient who had stopped their anti-retroviral therapy (FIG. 3). In this study CRP levels mimicked viral load fluctuations as the immune response switched on and off (FIG. 3). It is interesting to note that these CRP fluctuations have an approximate 14 day cycle.

Example 5

The "Pubmed" database was searched for the abstracts of journal articles which described the results of Phase II or Phase III clinical trials using anti-cancer agents (such as vinblastine and taxol) for the treatment of cancer. Other criteria that were used to select the "abstracts" were that the cancer was at a late stage (stage III or stage IV) and the disease had disseminated. Some studies used a single drug whereas others used combinations. No other criteria were used and studies with an atypical complete response rate were not disregarded.

The complete response rate (as indicated in the abstracts) for each trial was used to determine the average complete response rate of each type of cancer. The results are provided as Table 1. Notably, the average complete response rate varied only a small degree, namely between 5.1 to 8.2% for all cancers analysed. The results provided in Table 1 were used to determine the overall average complete response rate. This average complete response rate was 6.6% over at least 10 different types of cancers when considering the 144 trials analysed.

With specific regard to the data provided for ovarian cancer it should be noted that one study (Adachi et al., 2001) observed a complete response rate of 25% which was very large compared to the other 143 trials. This study looked at eight patients, with two patients providing a complete response rate. Whilst this is well within the realms of possibility, if the study is ignored the overall complete response rate for the remaining ovarian cancer studies is 7.1%.

The complete response rates are remarkably consistent between the different cancers, and treatment regimes thereof, suggesting an underlying factor relevant to all cancers and treatments thereof. As described herein, this factor is that the immune system is cycling. Accordingly, it can be argued that the complete response rates provided in Table 1 are the result of the anti-cancer agent being administered at an appropriate time such that effector cell numbers are maximized whilst regulator cell numbers are reduced or removed, or activity is down-regulated or compromised, by the anti-cancer agent sufficient to elicit a complete response.

TABLE 1

Complete Response Rates Resulting from Clinical Trails with Anti-Cancer Drugs against Various Cancers.

| Cancer Type | Complete Response Rate (%) | Number of Trials |
| --- | --- | --- |
| Mesothelioma[a] | 5.1 | 10 |
| Gastric[b] | 7.33 | 15 |
| Hepatocellular[c] | 6.6 | 8 |
| Pancreatic[d] | 7.35 | 4 |
| Melanoma[e] | 7.5 | 15 |
| Prostate[f] | 5.15 | 7 |
| NSC Lung[g] | 5.85 | 6 |
| Breast[h] | 7.36 | 19 |

TABLE 1-continued

Complete Response Rates Resulting from Clinical Trails with Anti-Cancer Drugs against Various Cancers.

| Cancer Type | Complete Response Rate (%) | Number of Trials |
|---|---|---|
| Ovarian[i] | 8.2 | 15 |
| Colorectal[j] | 6.85 | 28 |
| Miscellaneous[k] | 6.0 | 17 |

[a]Tsavaris et al (1997), Monnet et al (2002), Pinto et al (2001), Kindler et al (1999), Yogelzang et al (1997), Planting et al (1995), Chahinian et al (1993), Raghavan et al (1990), Henss et al (1988) and Mbidde et al (1986).
[b]Kollmannsberger et al (2000), Sugimachi et al (2000), Jeen et al (2001), Yamada et al (2001), Aitini et al (2001), Cho et al (2002), Kornek et al (2002), Hofheinz et al (2002), Constenla et al (2002), Kim et al (2002), Louvet et al (2002), Kikuyama et al (2002), Bar Sela et al (2002), Murad et al (1999) and Sakata et al (1998).
[c]Porta et al (1995), Pohl et al (2001), Oon et al (1980), Choi et al (1984), Zeng et al (1998), Carr et al (1997), Patt et al (2003) and Leung et al (1999).
[d]Murad et al (2003), Ashamalla et al (2003), Safran et al (2002) and Sherman et al (2001).
[e]Retsas et al (1996), Nathan et al (2000), Bafaloukos et al (2002), Bafaloukos et al (2002), Buzaid et al (1998), Gibbs et al (2000), Atkins et al (2002), Gundersen et al (1989), Johnson et al (1985), Nystrom et al (2003), Einzig et al (1991), Bedikian et al (1995), Einzig et al (1996), Nathan et al (2000) and Chapman et al (2002).
[f]Hudes et al (1997), Kelly et al (2001), Savarese et al (1999), Small et al (2001), Savarese et al (2001), Trivedi et al (2000) and Picus et al (1999).
[g]Mariotta et al (2002), Recchia et al (2002), Perng et al (2000), Ginopoulos et al (1999), Paccagnella et al (1996) and Agelaki et al (2001).
[h]Freyer et al (2003), Morabito et al (2003), Kosmas et al (2003), Gebbia et al (2003), Thomas et al (1994), Romero et al (1994), Pectasides et al (2001), Frasci et al (2002), Stathopoulos et al (2002), Gomez-Bernal et al (2003), Freyer et al (2003), Kornek et al (2002), Michelotti et al (1996), Kakolyris et al (1999), Twelves et al (1994), Fumoleau et al (1993) and Ibrahim et al (1999).
[i]Li et al (2002), Sehouli et al (2002), Rose et al (2003), Faivre et al (2002), Dieras et al (2002), Adachi et al (2001), Sutton et al (1994), McClay et al (1995), Manetta et al (1994), Guastalla et al (1994), Covens et al (1992), Einzig AI. (1994), Kjorstad et al (1992), Ozols et al (1984), Planner et al (1996) and Amadori et al (1997).
[j]Cassinello et al (2003), Glimelius et al (2002), Calvo et al (2002), Scheithauer et al (2002), Neri et al (2002), Falcone et al (2001), Kouroussis et al (2001), Meropol et al (2001), Comella et al (2000), Cascinu et al (1999), Sobrero et al (1995), Gamelin et al (1998), Romero et al (1998), Beerblock et al (1997), Blanke et al (1997), Grem et al (1993), Jeremic et al (1993), Posner et al (1992), Sinnige et al (1990), LoRusso et al (1989), Petrelli et al (1989), Valdivieso et al (1981), Cassinello et al (2003), Reina et al (2003), Comella et al (1999), Neri et al (1998), Pyrhonen et al (1992) and Beck et al (1984).
[k]Cancers included renal cell carcinoma, adenocarcinoma, squamous cell carcinoma, uterine cervical cancer, glioblastoma multiforme, metastatic osteosarcoma, urothelial cancer and endometrial cancer. Described by Schornagel et al (1989), Liu et al (2001), Forastiere et al (1987), Okuno et al (2002), Takasugi et al (1984), Hurteloup et al (1986), Kakolyris et al (2002), Morris et al (1998), Takeuchi et al (1991), Fountzilas et al (1999), Rosenthal et al (2000), Goorin et al (2002), Rodriguez-Galindo et al (2002), Ahmad et al (2002), DiPaola et al (2003) and Lissoni et al (1996).

If the typical cycle of effector/regulator cell numbers is considered as about 15 days, the data in Table 1 suggest a one day window to administer the anti-cancer therapy to achieve a complete response rate. Partial response rates in the order of 30% are typically noted suggesting that if the agent is administered at a 24 to 36 hour period either side of this "one day window" a beneficial effect can also be achieved.

Example 6

Patient

The patient was a 75 year old female designated herein "Mrs OM".

History

Liver cirrhosis, ischaemic heart disease, insulin dependent diabetic. Diagnosed with squamous cell carcinoma of lower oesophagus by endoscopy and biopsy/histology May 2004. The cancer resulted in the patient finding it difficulty to swallow.

Tumour Description

Five centimeter circumferential mass at the base of the oesophagus, partially occluding the lumen. Unknown epithelial/mural penetration.

Therapy Regimen

Radiotherapy approx 33 courses of 15 minutes duration every week day over 6-8 weeks. Plus limited chemotherapy due to underlying other medical conditions.

The oncologist agreed to give two application of chemotherapy (~8 hr infusion of 5 Fluorouracil and Carboplatin). The application would be coordinated with the patient's immune response cycle/oscillation to attempt timed downregulation of cycling tumour specific regulator cells.

Monitoring and Therapeutic Intervention

To detect the immune response oscillation, monitoring of the patient's immune response started on the May 28, 2004, day 1, using the following assays; CRP, SAA, C3, C4 & CA125. CA125 was used to monitor disease progression as this has been reported in the literature in the case of squamous cell carcinoma of the oesophagus.

During the initial stages of monitoring, the patient reported increased difficulty in swallowing, most likely due to the tumour growing. This was corroborated by a consistent rise in all the measured parameters (see FIGS. 4 to 7).

Interestingly the climbing CA125 briefly plateaued over an approximate 24 hr period, (FIG. 6 day 12-14) only to rise at a steeper gradient beyond that point. This was interpreted as the patient's immune response switching on and modulating the tumour growth and marker (CA125), only to switch off due to immune regulation at the end of the approximate 24 hr period.

This approximate 24 hr period established the end of one about 14 day cycle and the beginning of the next, and therefore a potential intervention point or a reference point for projecting ahead to further intervention points.

Having defined the beginning and end of the ~14 day cycle it was now possible to anticipate and project forward a number of days to best estimate two potential chemotherapeutic intervention points approximately 2 weeks apart.

It was decided to take blood/measurements from the patient on the Tuesday, Wednesday and Thursday (FIG. 7, 13, 14 & 15 July, days 46, 47 & 48, arrowed as B) to accurately define the therapeutic intervention point or window. If the cycle had been accurately determined, a peak followed by a down turn in the CRP should be seen over those days on which analysis was carried out. (FIG. 7). This pattern in the CRP should be repeated approximately 14 days later and in keeping with the persistent periodicity of the immune response oscillation. This was found to be the case (FIG. 7).

Based on the CRP results, the inventor recommended to the oncologist to administer the first application of chemotherapy about Wednesday Jul. 7, 2004 or Thursday Jul. 7, 2004. However, Mrs OM had already been booked for chemotherapy on Friday Jul. 7, 2004, and the oncologist decided not to change this appointment. Since this date was just after the peak in the CRP (FIG. 7, arrowed as C) it was felt by the inventor that the window of opportunity may have been missed because the application of therapy may be 24 hrs too late. The inventor expected that at the time the therapy was administered CRP would have begun to rise again. This prediction proved correct as no effect was apparent on the tumour after administration of the chemotherapy.

A second intervention point was determined/predicted and blood was taken on the Wednesday and Thursday (FIG. 7, 28th & 29th July, days 63 and 64 arrowed as D). The prediction was confirmed by a peak in the CRP analysis indicating Friday Jul. 7, 2004, day 65 (FIG. 7, arrowed as E) as the optimal intervention point for application of chemotherapy. Chemotherapy was administered as an 8 hr infusion on the Friday. On this occasion the inventor predicted that this would be appropriate time to administer the therapy as the CRP would still be decreasing.

On the Saturday the patient developed a mild fever and felt generally unwell. Early afternoon on the Sunday 1st August, day 67, (FIG. 7, arrowed as F), the patient haemorrhaged from the tumour site and consequently was admitted to hospital. The patient lost about 150 mls of blood and received 2 units of blood that day and intravenous fluids/nourishment for the next 9 days.

CRP was measured on Apr. 8, 2004, day 69 (FIG. 7, arrowed as G), and was found to have dropped significantly.

On the last day of hospitalisation the patient's oesophagus was examined endoscopically. No tumour was evident (FIG. 7, arrowed as H).

Interpretation

The patient's oscillating antitumour immune response was released from regulation by the timed targeting of tumour specific regulator cells by the single administration of the chemotherapeutic agents at the right designated time. This is when immune regulatory cells are clonally active, in mitosis and thus vulnerable to down-regulation. Once released from regulation the anti-tumour immune response resulted in a febrile episode as reported by the patient on day 66 and subsequent tumour destruction. The immune mediated tumour destruction resulted in haemorrhage due to the tumour's potential invasive involvement in the epithelium/wall of the oesophagus.

The above actions and observations demonstrates the following:
- It is possible to detect a persistent regular oscillation in the cancer patient.
- This oscillation is associated with the tumour burden.
- The oscillation has an approximate 14 day periodicity with a 7 day sub cycle.
- The beginning and end of the cycle can be determined by different parameters such as but not limited to CRP, SAA, C3, C4 and tumour antigen levels.
- The narrow window of opportunity for the application of a single. administration of chemotherapy can be determined.
- A single chemotherapeutic administration at the correct time directed against the cancer patient's immune system can lead to a successful therapeutic outcome.

Example 7

The patient was a 71 year old female designated herein "Mrs FO". Previously Mrs FO was diagnosed with ovarian cancer, received surgery and several rounds of standard chemotherapy. Patient represented with elevated CA125 at 200 U/ml prior to monitoring.

Patient was monitored (bled) every Monday, Wednesday & Friday for 4 weeks. A well described near synchronous and regular oscillation with a 7/14 day periodicity showing a close correlation between CRP, SAA & IL-2 serum measurements (see FIGS. 8 and 9). More interestingly, FIG. 10 which shows CRP & CA125 versus time, the CRP and CA125 oscillations are out of phase, indicating an inverse relationship between the immune system and the cancer marker.

FIG. 11 shows the relationship over time between SAA and complement factor C3. Note that the two major C3 peaks are approximately 14 days apart and coincide with alternating SAA peaks which are also approximately 14 days apart. This supports a hypothesis that the 7 day peaks represent alternating T and B cell clonal expansions and the major C3 peaks are B cell associated as complement is associated with antibody mediated lysis. This observation can assist in establishing the beginning and end of a cycle and therefore can also assist in determining the therapeutic intervention point.

Example 8

The patient was a 64 year old male designated herein "Mr GA". Bowel cancer was first diagnosed 1997, following which the patient was exposed to surgery, chemotherapy and radiotherapy. Lung recurrence was diagnosed by needle biopsy in February 2004. The patient was determined to possess multiple lesions and was subjected to 12 rounds of chemotherapy. The last chemotherapy was in September 2004. The most recent scan identified at least one 2 cm lesion upper left lung. Currently, relatively well/active (mid October 2004).

Blood was taken every other day (Monday, Wednesday, Friday) for 15 days. CRP was measured, with the resulting showing an approximate and regular 7/14 day CRP oscillation.

Example 9

A post menopausal opherectomised patient (WB) with re-emerging tumour and elevated CA125 levels was ask to record the frequency of hot flushes or febrile episodes and grade them as mild, moderate or severe. The intensity of these episodes were matched to the immune response CRP oscillation. The more intense episodes and their increased frequency were coincident with the large peaks. Thus recording body temperature may be used as an adjunct to define the beginning and or end of the immune response oscillation for the purposes of timing the application of therapy.

CROSS-REFERENCE TO RELATED APPLICATIONS

The present application claims priority from Provisional Patent Application No 2003905858 filed on 24 Oct. 2003, the contents of which is incorporated herein by reference.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Adachi, S., Ogasawara, T., Ito, K., Koyama, M., et al (2001) Oncol. Rep. 8:285-288.
Agelaki, S., Bania, H., Kouroussis, C., Blazoyiannakis, G., et al (2001) Lung Cancer 4:S77-80.
Ahmad, S. A., Patel, S. R., Ballo, M. T., Baker, T. P., et al (2002) J. Clin. Oncol. 20:521-527.
Aitini, E., Rabbi, C., Mambrini, A., Cavazzini, G., et al (2001) Tumori 87:20-24.
Amadori, D., Sansoni, E. and Amadori, A. (1997) Frontiers in Bioscience 2:20-26.
Ashamalla, H., Zaki, B., Mokhtar, B., Colella, F., et al (2003) Int. J. Radiat. Oncol. Biol. Phys. 55:679-687.
Atkins, M. B., Gollob, J. A., Sosman, J. A., McDermott, D. F., et al (2002) Clin. Cancer Res. 8:3075-3081.
Aziz, M., Akhtar, S, and Malik, A. (1998) Cancer Detect. Prey. 22:87-99.
Bafaloukos, D., Aravantinos, G., Fountzilas, G., Stathopoulos, G., et al (2002) Oncology 63:333-337.
Bafaloukos, D., Gogas, H., Georgoulias, V., Briassoulis, E., et al (2002) J. Clin. Oncol. 20:420-425.

Bar Sela, G., Tsalic, M., Gaitini, D., Steiner, M., et al (2002) J. Chemother. 14:623-626.
Beck, T. M., Curtis, P. W., Woodard, D. A., Hart, N. E., et al (1984) Cancer Treat. Rep. 68:647-650.
Bedikian, A. Y., Weiss, G. R., Legha, S. S., Burris, H. A., et al (1995) J. Clin. Oncol. 13:2895-2899.
Beerblock, K., Rinaldi, Y., Andre, T., Louvet, C., et al (1997) Cancer 79:1100-1105.
Belli F, Testori A, Rivoltini L, Maio M, et al. (2002) J Clin Oncol. 20:4169-4180.
Berd D, Sato T, Cohn H, Maguire H C Jr, Mastrangelo M J. (2001) Int J. Cancer. 94:531-539.
Blanke, C. D., Kasimis, B., Schein, P., Capizzi, R., et al (1997) J. Clin. Oncol. 15:915-920.
Buzaid, A. C., Colome, M., Bedikian, A., Eton, O., et al (1998) Melanoma Res. 8:549-556.
Calvo, E., Cortes, J., Rodriguez, J., Fernandez-Hidalgo, O., et al (2002) Clin. Colorectal Cancer 2:104-110.
Carr, B. I., Zajko, A., Bron, K., Orons, P., et al (1997) Semin. Oncol. 24:S6-97-S6-99.
Cascinu, S., Silva, R. R., Labianca, R., Barni, S., et al (1999) Ann. Oncol. 10:985-987.
Cassinello, J., Escudero, P., Salud, A., Marcos, F., et al (2003) Clin. Colorectal Cancer 3:108-112.
Cassinello, J., Lopez-Alvarez, P., Martinez-Guisado, A., Valladares, M., et al (2003) Med. Oncol. 20:37-43.
Chahinian, A. P., Antman, K., Goutsou, M., Corson, J. M., et al (1993) J. Clin. Oncol. 11:1559-1165.
Chapman, P. B., Panageas, K. S., Williams, L., Wolchok, J. D., et al (2002) Melanoma Res. 12:381-387.
Cho, E. K., Lee, W. K., Lim do, Y., Bang, S. M., et al (2002) J. Korean Med. Sci. 17:348-352.
Choi, T. K., Lee, N. W. and Wong, J. (1984) Cancer 53:401-405.
Comella, P., De Vita, F., Mancarella, S., De Lucia, L., et al (2000) Ann. Oncol. 11:1323-1333.
Comella, P., Lorusso, V., Casaretti, R., De Lucia, L., et al (1999) Tumori. 85:465-472.
Constenla, M., Garcia-Arroyo, R., Lorenzo, I., Carrete, N., et al (2002) Gastric Cancer 5:142-147.
Covens, A., O'Connell, G., Rusthoven, J. and Mazurka, J. (1992) Eur. J. Gynaecol. Oncol. 13:125-130.
Dieras, V., Bougnoux, P., Petit, T., Chollet, P., et al (2002) Ann. Oncol. 13:258-266.
DiPaola, R. S., Rubin, E., Toppmeyer, D., Eid, J., et al (2003) Med. Sci. Monit. 9:P15-11.
Eda, S., Kaufmann, J., Roos, W. and Phol, S. (1998) J. Clin. Lab. Analysis 12:137-144.
Einzig, A. I. (1994) Ann. Oncol. 6:S29-32.
Einzig, A. I., Hochster, H., Wiernik, P. H., Trump, D. L., et al (1991) Invest New Drugs 9:59-64.
Einzig, A. I., Schuchter, L. M., Recio, A., Coatsworth, S., et al (1996) Med. Oncol. 13:111-117.
Faivre, S., Le Chevalier, T., Monnerat, C., Lokiec, F., et al (2002) Ann. Oncol. 13:1479-1489.
Falcone, A., Allegrini, G., Masi, G., Lencioni, M., et al (2001) Oncology 61:28-35.
Forastiere, A. A., Gennis, M., Orringer, M. B. and Agha, F. P. (1987) J. Clin. Oncol. 5:1143-1149.
Fountzilas, G., Karavelis, A., Capizzello, A., Kalogera-Fountzila, A., et al (1999) J. Neurooncol. 45:159-165.
Frasci, G., D'Aiuto, G., Comella, P., Thomas, R., et al (2002) Oncology 62:25-32.
Freyer, G., Delozier, T., Lichinister, M., Gedouin, D., et al (2003) J. Clin. Oncol. 21:35-40.
Fumoleau, P., Delgado, F. M., Delozier, T., Monnier, A., et al (1993) J. Clin. Oncol. 11:1245-1252.
Gamelin, E., Boisdron-Celle, M., Delva, R., Regimbeau, C., et al (1998) J. Clin. Oncol. 16:1470-1478.
Gebbia, V., Blasi, L., Borsellino, N., Caruso, M., et al (2003) Anticancer Res. 23:765-771.
Gibbs, P., Iannucci, A., Becker, M., Allen, J., et al (2000) Melanoma Res. 10:171-179.
Ginopoulos, P., Mastronikolis, N. S., Giannios, J., Karana, A., et al (1999) Lung Cancer 23:31-37.
Glimelius, B., Ristamaki, R., Kjaer, M., Pfeiffer, P., et al (2002) Ann. Oncol. 13:1868-1873.
Gomez-Bernal, A., Cruz, J. J., Garcia-Palomo, A., Arizcun, A., et al (2003) Am. J. Clin. Oncol. 26:127-131.
Goorin, A. M., Harris, M. B., Bernstein, M., Ferguson, W., et al (2002) J. Clin. Oncol. 20:426-433.
Grem, J. L., Jordan, E., Robson, M. E., Binder, R. A., et al (1993) J. Clin. Oncol. 11:1737-1745.
Guastalla, J. P., Vermorken, J. B., Wils, J. A., George, M., et al (1994) Eur. J. Cancer 30A:45-49.
Gundersen, S, and Flokkmann, A. (1989) Cancer 64:1617-1619.
Henss, H., Fiebig, H. H., Schildge, J., Arnold, H., et al (1988) Onkologie 11:118-120.
Hofheinz, R. D., Hartung, G., Samel, S., Hochhaus, A., et al (2002) Onkologie 25:255-260.
Horvath, M., Fekete, B. and Rahoty, P. (1982) Oncology 39:20-22.
Hudes, G. R., Nathan, F., Khater, C., Haas, N., et al (1997) J. Clin. Oncol. 15:3156-3163.
Hurteloup, P., Armand, J. P., Cappelaere, P., Metz, R., et al (1986) Cancer Treat. Rep. 70:731-737.
Ibrahim, N. K., Rahman, Z., Valero, V., Willey, J., et al (1999) Cancer 86:1251-1257.
Jeen, Y. T., Yoon, S. Y., Shin, S. W., Kim, B. S., et al (2001) Cancer 91:2288-2293.
Jeremic, B., Acimovic, L. and Mijatovic, L. (1993) Cancer 71:2706-2708.
Johnson, D. H., Presant, C., Einhorn, L., Bartolucci, A. A., et al (1985) Cancer Treat. Rep. 69:821-824.
Kakolyris, S., Kourousis, C., Koukourakis, M., Androulakis, N., et al (1999) Am. J. Clin. Oncol. 22:568-572.
Kakolyris, S., Kouroussis, C., Koukourakis, M., Marvroudis, D., et al (2002) Oncology 63:213-218.
Kelly, W. K., Curley, T., Slovin, S., Heller, G., et al (2001) J. Clin. Oncol. 19:44-53.
Kikuyama, S., Inada, T., Oyama, R. and Ogata, Y. (2002) Anticancer Res. 22:3633-3636.
Kim, T. W., Kang, Y. K., Ahn, J. H., Chang, H. M., et al (2002) Ann. Oncol. 13:1893-1898.
Kimura, M., Tomita, Y., Imai, T., Saito, T. et al. (2001) Cancer 92:2072-2075.
Kindler, H. L., Belani, C. P., Herndon, J. E., Vogelzang, N. J., et al (1999) Cancer 86:1985-1991.
Kjorstad, K., Harris, A., Bertelsen, K., Slevin, M., et al (1992) Ann. Oncol. 3:217-222.
Kollmannsberger, C., Quietzsch, D., Haag, C., Lingenfelser, T., et al (2000) Br. J. Cancer 83:458-462.
Kornek, G. V., Haider, K., Kwasny, W., Lang, F., et al (1998) Br. J. Cancer 78:673-678.
Kornek, G. V., Raderer, M., Schull, B., Fiebiger, W., et al (2002) Br. J. Cancer 86:1858-1863.
Kosmas, C., Tsavaris, N., Malamos, N., Stavroyianni, N., et al (2003) Br. J. Cancer 88:1168-1174.
Kouroussis, C., Souglakos, J., Kakolyris, S., Mavroudis, D., et al (2001) Oncology 61:36-41.
Leung, T. W., Patt, Y. Z., Lau, W. Y., Ho, S. K., et al (1999) Clin. Cancer Res. 5:1676-1681.

Li, J. D., Guan, Z. Z., Liu, J. H., Xin, X. Y., et al (2002) Ai Zheng 21:416-420.

Lissoni, A., Zanetta, G., Losa, G., Gabriele, A., et al (1996) Ann. Oncol. 7:861-863.

Liu, J. H., Yang, M. H., Fan, F. S., Yen, C. C., et al (2001) Urology 57:650-654.

Liuzzo, G., Biasucci, L. M., Gallimore, J. R., Grillo, R. L. et al. (1994) New Engl. J. Med. 331:417-424.

LoRusso, P., Pazdur, R., Redman, B. G., Kinzie, J., et al (1989) Am. J. Clin. Oncol. 12:486-490.

Lotem M, Shiloni E, Pappo I, Drize O, et al. (2004) Br J Cancer 90:773-780.

Louvet, C., Andre, T., Tigaud, J. M., Gamelin, E., et al (2002) J. Clin. Oncol. 20:4543-4548.

Manetta, A., Boyle, J., Berman, M. L., DiSaia, P. J., et al (1994) Cancer 73:196-199.

Mariotta, S., Sposato, B., Li Bianchi, E., Fiorucci, F., et al (2002) Eur. Rev. Med. Pharmacol, Sci. 6:49-54.

Mbidde, E. K., Harland, S. J., Calvert, A. H. and Smith, I. E. (1986) Cancer Chemother. Pharmacol. 18:284-285.

McClay, E. F., Braly, P. D., Kirmani, S., Plaxe, S. C., et al (1995) Am. J. Clin. Oncol. 18:23-26.

Meropol, N. J., Niedzwiecki, D., Hollis, D., Schilsky, R. L., et al (2001) Cancer 91:1256-1263.

Michelotti, A., Gennari, A., Salvadori, B., Giannessi, P. G., et al (1996) Semin. Oncol. 23:38-40.

Monnet, I., Breau, J. L., Moro, D., Lena, H., et al (2002) Chest 121:1921-1927.

Morabito, A., Filippelli, G., Palmeri, S., Cascinu, S., et al (2003) Breast Cancer Res. Treat. 78:29-36.

Morris, M., Brader, K. R., Levenback, C., Burke, T. W., et al (1998) J. Clin. Oncol. 16:1094-1098.

Murad, A. M., Guimaraes, R. C., Aragao, B. C., Rodrigues, V. H., et al (2003) Am. J. Clin. Oncol. 26:151-154.

Murad, A. M., Petrioanu, A., Guimaraes, R. C., Aragao, B. C., et al (1999) Am. J. Clin. Oncol. 22:580-586.

Nathan, F. E., Berd, D., Sato, T. and Mastrangelo, M. J. (2000) Cancer 88:79-87.

Neri, B., Doni, L., Fulignati, C., Perfetto, F., et al (2002) Anticancer Drugs 13:719-724.

Neri, B., Gemelli, M. T., Pantalone, D., Pernice, M. L., et al (1998) Anticancer Drugs 9:599-602.

North, R. J. and Awwad, M. (1990) Immunology 71:90-95.

Nystrom, M. L., Steele, J. P., Shamash, J., Neville, F., et al (2003) Melanoma Res. 13:197-199.

O'Hanlon, D. M., Lynch, J., Cormican, M. and Given, H. F. (2002) Anticancer Res. 22:1289-1294.

O'Hara, R., Murphy, E. P., Whitehead, A. S., Fitzgearld, O. and Bresnihan, B. (2000) Arthritis Research 2:142-144.

Okuno, S. H., Mailliard, J. A., Suman, V. J., Edmonson, J. H., et al (2002) Cancer 94:2224-2231.

Onizuka, S., Tawara, I., Shimizu, J., Sakaguchi, S., et al (1999) Cancer Res. 59:3128-3133.

Oon, C. J., Chua, E. J., Foong, W. C., Tan, L. K., et al (1980) Ann. Acad. Med. Singapore 9:256-259.

Ozols, R. F., Speyer, J. L., Jenkins, J. and Myers, C. E. (1984) Cancer Treat. Rep. 68:1229-1232.

Paccagnella, A., Favaretto, A., Oniga, F., Festi, G., et al (1996) Cancer 78:1701-1707.

Patt, Y. Z., Hassan, M. M., Lozano, R. D., Brown, T. D., et al (2003) J. Clin. Oncol. 21:421-427.

Pectasides, D., Dimopoulos, M. A., Aravantinos, G., Kalophonos, H. P., et al (2001) Anticancer Res. 21:3575-3580.

Perng, R. P., Shih, J. F., Chen, Y. M., Delgado, F. M., et al (2000) Am. J. Clin. Oncol. 23:60-64.

Peterson, K. E., Strommes, I., Messer, R., Hasenkrug, K. and Chesebro, B. (2002) J. Viriol. 76:7942-7948.

Petrelli, N. J., Madejewicz, S., Rustum, Y., Herrera, L., et al (1989) Cancer Chemother. Pharmacol. 23:57-60.

Picus, J. and Schultz, M. (1999) Semin. Oncol. 26:14-18.

Pinto, C., Marino, A., Guaraldi, M., Melotti, B., et al (2001) Am. J. Clin. Oncol. 24:143-147.

Planner, R. S., Allen, D. G., Brand, A. H., Grant, P. T., et al (1996) Aust N.Z. J. Obstet. Gynaecol. 36:168-170.

Planting, A. S., van der Burg, M. E., Goey, S. H., Schellens, J. H., et al (1995) Ann. Oncol. 6:613-615.

Pohl, J., Zuna, I., Stremmel, W. and Rudi, J. (2001) Chemotherapy 47:359-365.

Porta, C., Moroni, M., Nastasi, G. and Arcangeli, G. (1995) Oncology 52:487-491.

Posner, M., Martin, A., Slapak, C. A., Clark, J. W., et al (1992) Am. J. Clin. Oncol. 15:239-241.

Price, C. P., Trull, A. K., Berry, D. and Gorman, E. G. (1987) J. Immunol. Methods 99:205-211.

Pyrhonen, S. O. and Kouri, M. O. (1992) Eur. J. Cancer 28A:1828-1832.

Raghavan, D., Gianoutsos, P., Bishop, J., Lee, J., et al (1990) J. Clin. Oncol. 8:151-154.

Read, S., Malmstrom, V. and Powrie, F. (2000) J. Exp. Med. 192:295-302.

Recchia, F., Lombardo, M., De Filippis, S., Rosselli, M., et al (2002) Anticancer Res. 22:1321-1328.

Reina, J. J., Aparicio, J., Salvador, J., Pica, J. M., et al (2003 in press) Cancer Chemother. Pharmacol.

Retsas, S., Mohith, A. and Mackenzie, H. (1996) Anticancer Drugs 7:161-165.

Rodriguez-Galindo, C., Daw, N. C., Kaste, S. C., Meyer, W. H., et al (2002) J. Pediatr. Hematol. Oncol. 24:250-255.

Romero, A., Rabinovich, M. G., Vallejo, C. T., Perez, J. E., et al (1994) J. Clin. Oncol. 12:336-341.

Romero, A. O., Perez, J. E., Cuevas, M. A., Lacava, J. A., et al (1998) Am. J. Clin. Oncol. 21:94-98.

Rose, P. G., Blessing, J. A., Ball, H. G., Hoffman, J., et al (2003) Gynecol. Oncol. 88:130-135.

Rosenthal, M. A., Gruber, M. L., Glass, J., Nirenberg, A., et al (2000) J. Neurooncol. 47:59-63.

Safran, H., Dipetrillo, T., Iannitti, D., Quirk, D., et al (2002) Int. J. Radiat. Oncol. Biol. Phys. 54:137-141.

Sakata, Y., Ohtsu, A., Horikoshi, N., Sugimachi, K., et al (1998) Eur. J. Cancer 34:1715-1720.

Salomon, B., Lenschow, D. J., Rhee, L., Ashourian, N., et al (2000) Immunity 12:431-440.

Savarese, D., Taplin, M. E., Halabi, S., Hars, V., et al (1999) Semin. Oncol. 26:39-44.

Savarese, D. M., Halabi, S., Hars, V., Akerley, W. L., et al (2001) J. Clin. Oncol. 19:2509-2516.

Scheithauer, W., Kornek, G. V., Raderer, M., Schull, B., et al (2002) Ann. Oncol. 13:1583-1589.

Schornagel, J. H., Verweij, J., ten Bokkel Huinink, W. W., Klijn, J. G., et al (1989) J. Urol. 142:253-256.

Sehouli, J., Stengel, D., Oskay, G., Camara, O., et al (2002) Ann. Oncol. 13:1749-1755.

Senju, O., Takagi, Y., Gomi, K., Ishii, N., et al (1983) Jap. J. Clin. Lab. Automation 8:161-165.

Sherman, W. H. and Fine, R. L. (2001) Oncology 60:316-321.

Shimizu, J., Yamazaki, S. and Sakaguchi, S. (1999) J. Immunol. 163:5211-5218.

Shimizu, J., Yamazaki, S., Takahashi, T., Ishida, Y. and Sakaguchi, S. (2002) Nature Immunol. 3:135-142.

Sinnige, H. A., Sleijfer, D. T., de Vries, E. G., Willemse, P. H., et al (1990) Eur. J. Cancer 26:625-628.

Small, E. J., Bok, R., Reese, D. M., Sudilovsky, D., et al (2001) Semin. Oncol. 28:71-76.
Smithers M, O'Connell K, MacFadyen S, Chambers M, et al. (2003) Cancer Immunol Immunother. 52:41-52.
Sobrero, A. F., Aschele, C., Guglielmi, A. P., Mori, A. M., et al (1995) Clin. Cancer Res. 1:955-960.
Stathopoulos, G. P., Rigatos, S. K., Pergantas, N., Tsavdarides, D., et al (2002) J. Clin. Oncol. 20:37-41.
Sugimachi, K. and Maehara, Y. (2000) Surg. Today 30:1067-1072.
Suri-Payer, E. and Cantor, H. (2001) J. Autoimmunity 16:115-23.
Sutmuller, R. P., van Duivenvoorde, L. M., van Elsas, A., Schumacher, T. N. et al (2001) J. Exp. Med. 194:823-832.
Sutton, G. P., Blessing, J. A., Homesley, H. D. and Malfetano, J. H. (1994) Gynecol. Oncol. 53:24-26.
Takahashi, T., Tagami, T., Yamazaki, S., Uede, T. et al (2000) J. Exp. Med. 192:303-310.
Takasugi, B. J., Robertone, A. B., Salmon, S. E., Jones, S. E., et al (1984) Invest New Drugs 2:387-390.
Takeuchi, S., Dobashi, K., Fujimoto, S., Tanaka, K., et al (1991) Gan to Kagaku Ryoho 18:1681-1689.
Thomas, G. W., Muss, H. B., Jackson, D. V., McCulloch, J., et al (1994) Cancer Chemother. Pharmacol. 35:165-168.
Trefzer U, Herberth G, Wohlan K, Milling A, et al. (2004) Int J Cancer 110:730-740.
Trivedi, C., Redman, B., Flaherty, L. E., Kucuk, O., et al (2000) Cancer 89:431-436.
Tsavaris, N., Primikirios, N., Mylonakis, N., Varouchakis, G., et al (1997) Anticancer Res. 17:3799-3802.
Twelves, C. J., Dobbs, N. A., Curnow, A., Coleman, R. E., et al (1994) Br. J. Cancer 70:990-993.
Valdivieso, M., Bedikian, A. Y., Bodey, G. P. and Freireich, E. J. (1981) Cancer Treat. Rep. 65:877-879.
Weinstein, P. S., Skinner, M., Sipe, J. D., Lokich, J. J. et al. (1984) Scand. J. Immunol. 19:193-198.
Wittig B, Marten A, Dorbic T, Weineck S, et al. (2001) Hum Gene Ther. 12:267-278.
Yamada, Y., Shirao, K., Ohtsu, A., Boku, N., et al (2001) Ann. Oncol. 12:1133-1137.
Yogelzang, N. J., Herndon, J. E., Cirrincione, C., Harmon, D. C., et al (1997) Cancer 79:2237-2242.
Zeng, Z. C., Tang, Z. Y., Liu, K. D., Lu, J. Z., et al (1998) J. Cancer Res. Clin. Oncol. 124:275-280.

The invention claimed is:

1. A method of treating squamous cell carcinoma in a patient, the method comprising:
   i) measuring c-reactive protein (CRP) in a patient suffering from squamous cell carcinoma, or samples obtained therefrom, wherein the measuring is conducted for a period of time that represents at least one cycle of persistent CRP cycling;
   ii) analysing the results from step i) to understand the dynamics of the persistent CRP cycling and to determine or predict a peak in the CRP cycling; and
   iii) administering an agent to the patient in a one day window beginning at the determined or predicted peak in the CRP cycling, wherein the agent is an anti-proliferative drug selected from the group consisting of antimetabolites and alkylating agents.

2. The method of claim 1, wherein the patient is monitored for a period of at least 21 days.

3. The method of claim 1, wherein the patient is monitored at least about every 3 days.

4. The method of claim 1, wherein the patient has not been exposed to a treatment for the squamous cell carcinoma for at least 21 days.

5. The method of claim 1, wherein the patient is a human.

6. The method of claim 1, wherein the anti-metabolite is selected from the group consisting of methotrexate, fluorouracil, floxuridine, cytarabine, mercaptopurine, thioguanine, pentostatin and hydroxyurea.

7. The method of claim 1, wherein the alkylating agent is selected from the group consisting of carboplatin, mechlorethamine, cyclophosphamide, ifosfamide, melphalan, chlorambucil, hexamethyl-melamine, thiotepa, busulfan, carmustine, lomustine, semustine, streptozocin, dacarbazine, cisplatin and procarbazine.

8. The method of claim 1, wherein the anti-proliferative drug is selected from the group consisting of 5-fluorouracil, carboplatin and combinations thereof.

9. The method of claim 1, wherein the squamous cell carcinoma is squamous cell carcinoma of oesophagus.

* * * * *